United States Patent
Liu

(10) Patent No.: US 8,362,218 B2
(45) Date of Patent: Jan. 29, 2013

(54) PEPTIDES TARGETING TNF FAMILY RECEPTORS AND ANTAGONIZING TNF ACTION, COMPOSITIONS, METHODS AND USES THEREOF

(75) Inventor: Chuanju Liu, Orange, CT (US)

(73) Assignee: New York University School of Medicine, New York, NY (US)

( * ) Notice: Subject to any disclaimer, the term of this patent is extended or adjusted under 35 U.S.C. 154(b) by 131 days.

(21) Appl. No.: 12/799,024

(22) Filed: Apr. 16, 2010

(65) Prior Publication Data

US 2010/0298232 A1    Nov. 25, 2010

Related U.S. Application Data

(60) Provisional application No. 61/212,971, filed on Apr. 17, 2009.

(51) Int. Cl.
  C07K 14/475    (2006.01)
  A61K 38/18     (2006.01)
  A61P 29/00     (2006.01)
(52) U.S. Cl. ........ 530/399; 514/7.6; 514/16.6; 514/12.2
(58) Field of Classification Search .................. None
  See application file for complete search history.

(56) References Cited

U.S. PATENT DOCUMENTS 7,427,595 B1 * 9/2008 Zhu et al. ................... 514/1.1

FOREIGN PATENT DOCUMENTS

WO    WO 2008/019187 A2 *  2/2008
WO    2008/094687         8/2008

OTHER PUBLICATIONS

Bowie et al. Deciphering the message in protein sequences: tolerance to amino acid substitutions. Science, (Mar. 16, 1990) 247 (4948) 1306-10.*
Guo et al. Protein tolerance to random amino acid change. Proc Natl Acad Sci U S A. Jun. 22, 2004;101(25):9205-10. Epub Jun. 14, 2004.*
MacEwan DJ. TNF ligands and receptors—a matter of life and death. Br J Pharmacol. Feb. 2002;135(4):855-75.*
Mackowiak PA. Brief history of antipyretic therapy. Clin Infect Dis. Oct. 2000;31 Suppl 5:S154-6.*
Ngo et al., in The Protein Folding Problem and Tertiary Structure Prediction, Merz and Le Grand (Eds), Aug. 1994, Springer Verlag, pp. 433 and 492-495.*
Ahmed, Z. et al (2007) Carilage oliomeric matrix protein associates with granulin-epithelin precursor (GEP) and potentiates GEP-stimulated chondrocyte proliferation J. Neuroinflammation 4(7):1-13.
Anakwe, O.O. et al (1990) Acrosome biogenesis begins during meiosis: evidence from the synthesis and distribution of an acrosomal glycoprotein, acrogranin, during guinea pig spermatogenesis Biol Reprod 42(2):317-328.
Attur, M.G. et al (2002) "A system biology" approach to bioinformatics and functional genomics in complex human diseases: arthritis Curr Issues Mol Biol 4(4):129-146.
Baba,T. et al (1993) Acrogranin, an acrosomal cysteine-rich glycoprotein, is the precursor of the growth-modulating peptides, granulins, and epithelins, and is expressed in somatic as well as male germ cells Mol Reprod Dev 34 (3):233-243.
Barreda, D.R. et al (2004) Differentially expressed genes that encode potential markers of goldfish macrophage development in vitro Dev Comp Immunol 28(7-8):727-746.
Bateman, A. et al (1990) Granulins, a novel class of peptide from leukocytes Biochem Biophys Res Commun 173 (3):1161-1168.
Bateman, A. et al (1998) Granulins: the structure and function of an emerging family of growth factors J. Endocrinol 158(2):145-151.
Bhandari, V. et al (1992) Isolation and sequence of the granulin precursor cDNA from human bone marrow reveals tandem cysteine-rich granulin domains Proc. Natl. Acad. Sci. USA 89(5): 1415-1719.
Daniel, R. et al (2000) Cellular localization of gene expression for progranulin J Histochem Cytochem 48(7):999-1009.
Davidson, B. et al (2004) Granulin-Epithelin Precursor Is a Novel Prognostic Marker in Epithelial Ovarian Carcinoma Cancer 100(10):2139-2147.
Gonzalez, E.M. et al (2003) A Novel Interaction between Perlecan Protein Core and Progranulin J Biol Chem 278 (40):38113-38116.
He, Z. et al (1999) Progranulin Gene Expression Regulates Epithelial Cell Growth and Promotes Tumor Growth in Vivol Cancer Res 59:3222.
He, Z. et al (2003) Progranulin is a mediator of the wound response Nat Med 9(2):225-229.
He, Z. et al (2003) Progranulin is a mediator of the wound response J Mol Med 81(10):600-612.
Hogue, M. et al (2003) The growth factor granulin interacts with cyclin T1 and modulates P-TEFb-dependent transcription Mol Cell Biol 23(5):1688-1702.
Hogue, M. et al (2005) Granulin and Granulin Repeats Interact with the TatP-TEFb Complex and Inhibit Tat Transactivation J Biol Chem 280(14):13648-13657.
Hrabal, R. et al (1996) The hairpin stack fold, a novel protein architecture for a new family of protein growth factors Nat Struct Biol 3(9):747-752.
Jones, M.B. et al (2003) The granulin-epithelin precursor: a putative new growth factor for ovarian cancer Gynecol Oncol 88(1 pt. 2):S136-139.

(Continued)

*Primary Examiner* — David Romeo
(74) *Attorney, Agent, or Firm* — Foley & Lardner LLP

(57) ABSTRACT

The present invention provides modulators of TNF, particularly peptides and their derivatives, particularly GEP peptides, which antagonize TNF and TNF-mediated responses, activity or signaling. The invention provides methods of antagonizing TNF and the modulation of TNF-mediated diseases or responses, including inflammatory diseases and conditions. Compositions of GEP peptides, including in combination with other inflammatory mediators, are provided. Methods of treatment, alleviation, or prevention of TNF-mediated diseases and inflammatory conditions, including rheumatoid arthritis, osteoarthritis, ankylosing spondylitis, psoriasis, inflammatory bowel diseases, Chrohn's disease, ulcerative colitis, uveitis, inflammatory lung diseases, chronic obstructive pulmonary disease, are provided.

11 Claims, 38 Drawing Sheets

OTHER PUBLICATIONS

Justen, H.P. et al (2000) Differential gene expression in synovium of rheumatoid arthritis and osteoarthritis Mol Cell Biol Res Commun 3(3):165-172.

Lu, R. et al (2000) Inhibition of PC cell-derived growth factor (PCDGF, epithelin/granulin precursor) expression by antisense PCDGF cDNA transfection inhibits tumorigenicity of the human breast carcinoma cell line MDA-MB-468 Proc Natl Acad Sci 97(8):3993-3998.

MacRae V.E. et al (2006) The pathophysiology of the growth plate in juvenile idiopathic arthritis Rheumatology (Oxford) 45(1):11-19.

Martel-Pelletier, J. (1999) Pathophysiology of osteoarthritis Osteoarthritis Cartilage 7(4):371-373.

Ong, C.H. et al (2003) Progranulin (granulin-epithelin precursor, PC-cell derived growth factor, acrogranin) in proliferation and tumorigenesis Histol Histophathol 18(4):1275-1288.

Petersson, I.F. et al.(1998) Changes in cartilage and bone metabolism identified by serum markers in early osteoarthritis of the knee joint Br J Rheumatol 37(1):46-50.

Sun, X. et al (2004) Mesothelial Differentiation as Reflected by Differential Gene Expression Am J Respir Cell Mol Biol 30(4):510-518.

Suzuki, M. et al (2002) Granulin precursor gene: a sex steroid-inducible gene involved in sexual differentiation of the rat brain Mol Genet Metab 75(1):31-37.

Thornburg, N. J. et al (2004) Identification of Epstein-Barr virus RK-BARF0-interacting proteins and characterization of expression pattern J Virol 78(23):12848-12856.

Wang, W. et al (2003) PC cell-derived growth factor (granulin precursor) expression and action in human multiple myeloma Clin Cancer Res 9(6):2221-2228.

Wright, W.E. et al (1989) Myogenin, a factor regulating myogenesis, has a domain homologous to MyoD Cell 56 (4):607-617.

Xu, S.Q. et al (1998) The granulin/epithelin precursor abrogates the requirement for the insulin-like growth factor 1 receptor for growth in vitro J Biol Chem 273(32):20078-20083.

Xu, K. et al (2007) Cartilage oligomeric matrix protein associates with granulin-epithelin precursor (GEP) and potentiates GEP-stimulated chendrocyte-proliferation J Biol Chem 282(15):11347-11355.

Zanocco-Marani, T. et al (1999) Biological activities and signaling pathways of the granulin/epithelin precursor Cancer Res 59(20):5331-5340.

Zhang, H. et al (1998) Inhibition of tumorigenicity of the teratoma PC cell line by transfection with antisense cDNA for PC cell-derived growth factor (PCDGF, epithelin/granulin precursor) Proc Natl Acad Sci 95(24):14202-14207.

Zhou, J. et al (1993) Purification of an autocrine growth factor homologous with mouse epithelin precursor from a highly tumorigenic cell line J. Biol Chem 268(15):10863-10869.

Zhu, J. et al (2002) Conversion of proepithelin to epithelins: roles of SLPI and elastase in host defense and wound repair Cell 111(6):867-878.

\* cited by examiner

FIGURE 23

```
Met Trp Thr Leu Val Ser Trp Val Ala Leu Thr Ala Gly Leu Val Ala
 1           5                   10                  15
Gly Thr Arg Cys Pro Asp Gly Gln Phe Cys Pro Val Ala Cys Cys Leu
             20                  25              30
Asp Pro Gly Gly Ala Ser Tyr Ser Cys Cys Arg Pro Leu Leu Asp Lys
         35              40              45
Trp Pro Thr Thr Leu Ser Arg His Leu Gly Gly Pro Cys Gln Val Asp
     50              55              60
Ala His Cys Ser Ala Gly His Ser Cys Ile Phe Thr Val Ser Gly Thr
65              70              75                      80
Ser Ser Cys Cys Pro Phe Pro Glu Ala Val Ala Cys Gly Asp Gly His
                 85              90                      95
His Cys Cys Pro Arg Gly Phe His Cys Ser Ala Asp Gly Arg Ser Cys
             100             105             110
Phe Gln Arg Ser Gly Asn Asn Ser Val Gly Ala Ile Gln Cys Pro Asp
         115             120             125
Ser Gln Phe Glu Cys Pro Asp Phe Ser Thr Cys Cys Val Met Val Asp
     130             135             140
Gly Ser Trp Gly Cys Cys Pro Met Pro Gln Ala Ser Cys Cys Glu Asp
145             150             155                     160
Arg Val His Cys Cys Pro His Gly Ala Phe Cys Asp Leu Val His Thr
             165             170             175
Arg Cys Ile Thr Pro Thr Gly Thr His Pro Leu Ala Lys Lys Leu Pro
             180             185             190
Ala Gln Arg Thr Asn Arg Ala Val Ala Leu Ser Ser Ser Val Met Cys
         195             200             205
Pro Asp Ala Arg Ser Arg Cys Pro Asp Gly Ser Thr Cys Cys Glu Leu
         210             215             220
Pro Ser Gly Lys Tyr Gly Cys Cys Pro Met Pro Asn Ala Thr Cys Cys
225             230             235                     240
Ser Asp His Leu His Cys Cys Pro Gln Asp Thr Val Cys Asp Leu Ile
             245             250             255
Gln Ser Lys Cys Leu Ser Lys Glu Asn Ala Thr Thr Asp Leu Leu Thr
         260             265             270
Lys Leu Pro Ala His Thr Val Gly Asp Val Lys Cys Asp Met Glu Val
         275             280             285
Ser Cys Pro Asp Gly Tyr Thr Cys Cys Arg Leu Gln Ser Gly Ala Trp
     290             295             300
Gly Cys Cys Pro Phe Thr Gln Ala Val Cys Cys Glu Asp His Ile His
305             310             315                     320
Cys Cys Pro Ala Gly Phe Thr Cys Asp Thr Gln Lys Gly Thr Cys Glu
             325             330             335
Gln Gly Pro His Gln Val Pro Trp Met Glu Lys Ala Pro Ala His Leu
             340             345             350
Ser Leu Pro Asp Pro Gln Ala Leu Lys Arg Asp Val Pro Cys Asp Asn
         355             360             365
Val Ser Ser Cys Pro Ser Ser Asp Thr Cys Cys Gln Leu Thr Ser Gly
     370             375             380
Glu Trp Gly Cys Cys Pro Ile Pro Glu Ala Val Cys Cys Ser Asp His
385             390             395                     400
Gln His Cys Cys Pro Gln Arg Tyr Thr Cys Val Ala Glu Gly Gln Cys
             405             410             415
Gln Arg Gly Ser Glu Ile Val Ala Gly Leu Glu Lys Met Pro Ala Arg
             420             425             430
Arg Gly Ser Leu Ser His Pro Arg Asp Ile Gly Cys Asp Gln His Thr
         435             440             445
Ser Cys Pro Val Gly Gly Thr Cys Cys Pro Ser Gln Gly Gly Ser Trp
     450             455             460
Ala Cys Cys Gln Leu Pro His Ala Val Cys Cys Glu Asp Arg Gln His
465             470             475                     480
Cys Cys Pro Ala Gly Tyr Thr Cys Asn Val Lys Ala Arg Ser Cys Glu
             485             490             495
Lys Glu Val Val Ser Ala Gln Pro Ala Thr Phe Leu Ala Arg Ser Pro
             500             505             510
His Val Gly Val Lys Asp Val Glu Cys Gly Glu Gly His Phe Cys His
             515             520             525
Asp Asn Gln Thr Cys Cys Arg Asp Asn Arg Gln Gly Trp Ala Cys Cys
         530             535             540
Pro Tyr Ala Gln Gly Val Cys Cys Ala Asp Arg Arg His Cys Cys Pro
545             550             555                     560
Ala Gly Phe Arg Cys Ala Arg Arg Gly Thr Lys Cys Leu Arg Arg Glu
             565             570             575
Ala Pro Arg Trp Asp Ala Pro Leu Arg Asp Pro Ala Leu Arg Gln Leu
             580             585             590
Leu
```

FIGURE 24

Atsttrin peptide sequence (1/2F+P3+P4+1/2A+P5+1/2C):

PQASCCEDRVHCCPHGAFCDLVHTRCITPTGTHPLAKKLPAQRTNRAVALSSSASSKENATTDLLTKLPAHTVGDVKCD
MEVSCPDGYTCCRLQSGAWPWCEQGPHQVPWMEKAPAHLSLPDPQALKRDVPCDNVSSCPSSDTCCQLTSGEWGCCPIP

Other peptide Sequences:
F + P3:

IQCPDSQFECPDFSTCCVMVDGSWGCCPMPQASCCEDRVHCCPHGAFCDLVHTRCITPTGTHP

P4 + A:

SKENATTDLLTKLPAHTVGDVKCDMEVSCPDGYTCCRLQSGAWGCCPFTQAVCCEDHIHCCPAGFTCDTQKGTCE

P5 + C:

QGPHQVPWMEKAPAHLSLPDPQALKRDVPCDNVSSCPSSDTCCQLTSGEWGCCPIPEAVCCSDHQHCCPQGYTCVAEGQCQ

1/2F+P3+P4+1/2A:

PQASCCEDRVHCCPHGAFCDLVHTRCITPTGTHPLAKKLPAQRTNRAVALSSSASSKENATTDLLTKLPAHTVGDVKCDME
VSCPDGYTCCRLQSGAW

P4+1/2A+P5+1/2C:

SKENATTDLLTKLPAHTVGDVKCDMEVSCPDGYTCCRLQSGAWPWCEQGPHQVPWMEKAPAHLSLPDPQALKRDVPCDNVS
SCPSSDTCCQLTSGEWGCCPIP

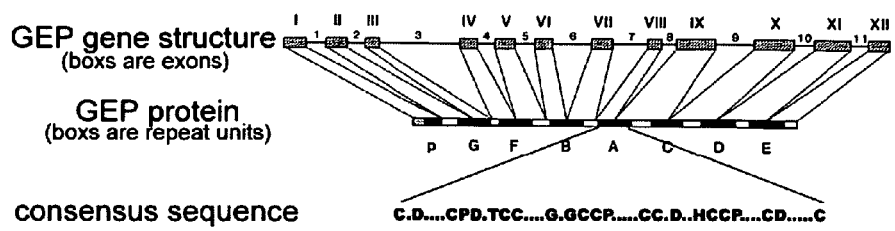

GEP gene structure (boxs are exons)

GEP protein (boxs are repeat units)

consensus sequence    C.D....CPD.TCC....G.GCCP.....CC.D..HCCP....CD.....C

B

```
  1  MWILVSWLAL  VARLVAGTQC  PDGQFCPVAC  CLDQGGANYS  CCNPLLDTWP  IITSRRLDGS

61  CQIRDHCPDG  YSCLLTVSGT  SSCCPFSEGV  SCDDGQHCCP  RGFHCSADGK  SCSQISDSLL

121  GAVQCPGSQF  ECPDSATCCI  MIDGSWGCCP  MPQASCCEDR  VHCCPHGASC  DLVHTRCISP

181  TGTHPLLKKF  PAQRTNRAVA  SFSVVCPDAK  TQCPDDSTCC  ELPTGKYGCC  PMPNAICCSD

241  HLHCCPQDTV  CDLIQSKCIS  KDYTTDLMTK  LPGYPVNEVK  CDLEVSCPDG  YTCCRLNTGA
                                                              GrnA
301  WGCCPFTKAV  CCEDHIHCCP  AGFQCHTETG  TCELGVLQVP  WMKKVTASLS  LPDPQILKND

361  VPCDDFSSCP  SNNTCCRLSS  GDWGCCPMPE  AVCCLDHQHC  CPQGFKCMDE  GYCQKGDRMV
     GrnC
421  AGLEKMPVRQ  TTLLQHGDIG  CDQHTSCPVG  QTCCPSLKGS  WACCQLPHAV  CCEDRQHCCP
                        GrnD
481  AGYTCNVKAR  TCEKDAGSVQ  PSMDLTFGSK  VGNVECGAGH  FCHDNQSCCK  DSQGGWACCP
                                          GrnE
541  YVKGVCCRDG  RHCCPIGFHC  SAKGTKCLRK  KTPRWDILLR  DPAPRPLL
```

FIGURE 30
A
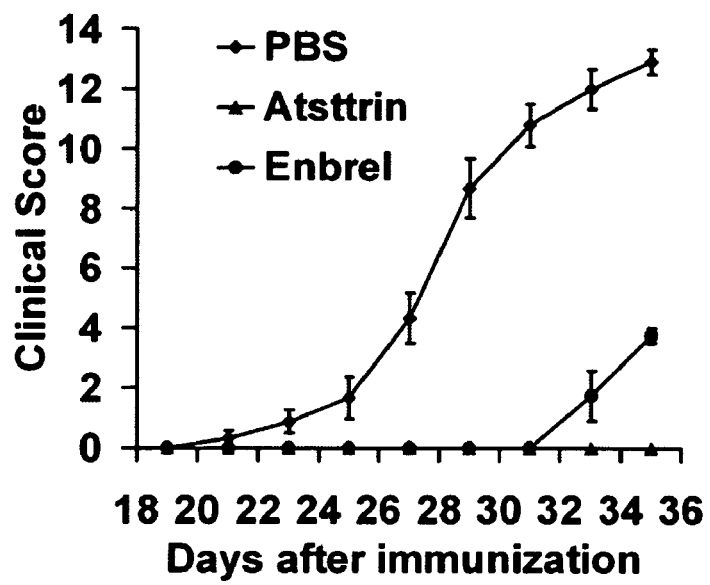
B
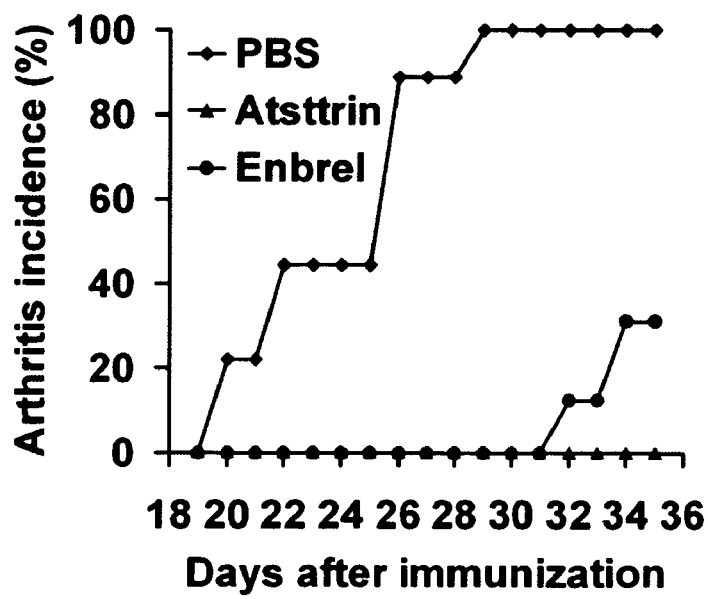

FIGURE 32
A
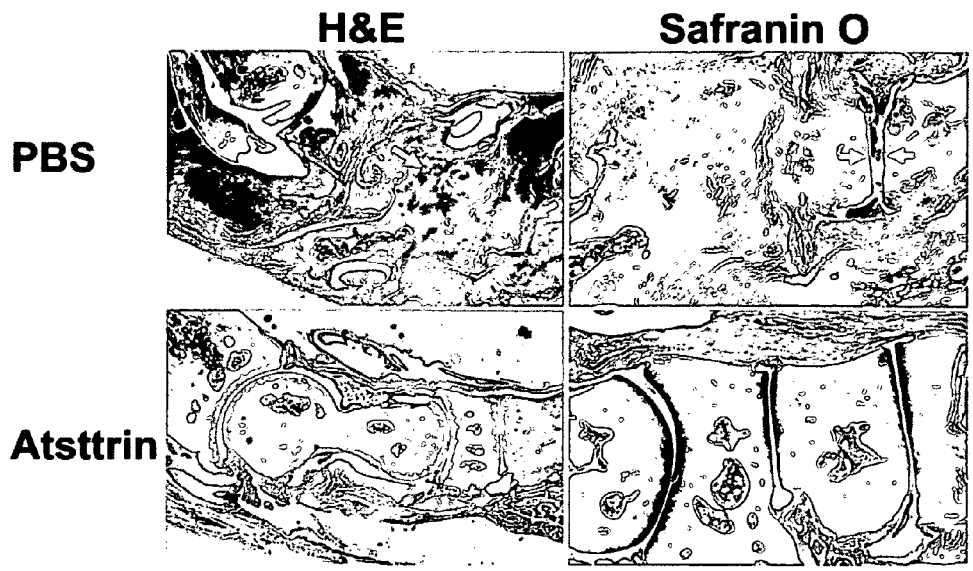
B
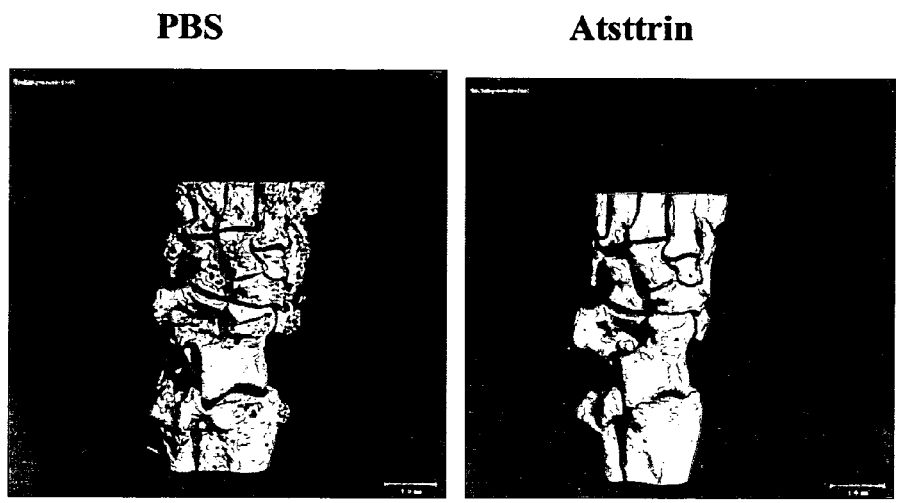

FIGURE 33

PBS　　Atsttrin

SEQUENCE LISTING

```
<160> NUMBER OF SEQ ID NOS: 10

<210> SEQ ID NO 1
<211> LENGTH: 593
<212> TYPE: PRT
<213> ORGANISM: Homo sapiens

<400> SEQUENCE: 1

Met Trp Thr Leu Val Ser Trp Val Ala Leu Thr Ala Gly Leu Val Ala
 1               5                  10                  15

Gly Thr Arg Cys Pro Asp Gly Gln Phe Cys Pro Val Ala Cys Cys Leu
                20                  25                  30

Asp Pro Gly Gly Ala Ser Tyr Ser Cys Cys Arg Pro Leu Leu Asp Lys
            35                  40                  45

Trp Pro Thr Thr Leu Ser Arg His Leu Gly Gly Pro Cys Gln Val Asp
        50                  55                  60

Ala His Cys Ser Ala Gly His Ser Cys Ile Phe Thr Val Ser Gly Thr
    65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
                100                 105                 110

Phe Gln Arg Ser Gly Asn Asn Ser Val Gly Ala Ile Gln Cys Pro Asp
            115                 120                 125

Ser Gln Phe Glu Cys Pro Asp Phe Ser Thr Cys Cys Val Met Val Asp
        130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220
```

```
Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
370                 375                 380

Glu Trp Gly Cys Cys Pro Ile Pro Glu Ala Val Cys Cys Ser Asp His
385                 390                 395                 400

Gln His Cys Cys Pro Gln Arg Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Gly Ser Leu Ser His Pro Arg Asp Ile Gly Cys Asp Gln His Thr
        435                 440                 445

Ser Cys Pro Val Gly Gly Thr Cys Cys Pro Ser Gln Gly Gly Ser Trp
450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
530                 535                 540

Pro Tyr Ala Gln Gly Val Cys Cys Ala Asp Arg Arg His Cys Cys Pro
545                 550                 555                 560

Ala Gly Phe Arg Cys Ala Arg Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu

<210> SEQ ID NO 2
<211> LENGTH: 158
<212> TYPE: PRT
<213> ORGANISM: Artificial Sequence
<220> FEATURE:
<223> OTHER INFORMATION: atsttrin peptide derived from human GEP
```

```
<400> SEQUENCE: 2

Pro Gln Ala Ser Cys Cys Glu Asp Arg Val His Cys Cys Pro His Gly
 1               5                  10                  15

Ala Phe Cys Asp Leu Val His Thr Arg Cys Ile Thr Pro Thr Gly Thr
                20                  25                  30

His Pro Leu Ala Lys Lys Leu Pro Ala Gln Arg Thr Asn Arg Ala Val
            35                  40                  45

Ala Leu Ser Ser Ser Ala Ser Ser Lys Glu Asn Ala Thr Thr Asp Leu
        50                  55                  60

Leu Thr Lys Leu Pro Ala His Thr Val Gly Asp Val Lys Cys Asp Met
 65                 70                  75                  80

Glu Val Ser Cys Pro Asp Gly Tyr Thr Cys Cys Arg Leu Gln Ser Gly
                85                  90                  95

Ala Trp Pro Trp Cys Glu Gln Gly Pro His Gln Val Pro Trp Met Glu
                100                 105                 110

Lys Ala Pro Ala His Leu Ser Leu Pro Asp Pro Gln Ala Leu Lys Arg
            115                 120                 125

Asp Val Pro Cys Asp Asn Val Ser Ser Cys Pro Ser Ser Asp Thr Cys
        130                 135                 140

Cys Gln Leu Thr Ser Gly Glu Trp Gly Cys Cys Pro Ile Pro
145                 150                 155

<210> SEQ ID NO 3
<211> LENGTH: 63
<212> TYPE: PRT
<213> ORGANISM: Artificial Sequence
<220> FEATURE:
<223> OTHER INFORMATION: peptide derived from human GEP

<400> SEQUENCE: 3

Ile Gln Cys Pro Asp Ser Gln Phe Glu Cys Pro Asp Phe Ser Thr Cys
 1               5                  10                  15

Cys Val Met Val Asp Gly Ser Trp Gly Cys Cys Pro Met Pro Gln Ala
                20                  25                  30

Ser Cys Cys Glu Asp Arg Val His Cys Cys Pro His Gly Ala Phe Cys
            35                  40                  45

Asp Leu Val His Thr Arg Cys Ile Thr Pro Thr Gly Thr His Pro
        50                  55                  60

<210> SEQ ID NO 4
<211> LENGTH: 75
<212> TYPE: PRT
<213> ORGANISM: Artificial Sequence
<220> FEATURE:
<223> OTHER INFORMATION: peptide derived from human GEP

<400> SEQUENCE: 4

Ser Lys Glu Asn Ala Thr Thr Asp Leu Leu Thr Lys Leu Pro Ala His
 1               5                  10                  15

Thr Val Gly Asp Val Lys Cys Asp Met Glu Val Ser Cys Pro Asp Gly
                20                  25                  30

Tyr Thr Cys Cys Arg Leu Gln Ser Gly Ala Trp Gly Cys Cys Pro Phe
            35                  40                  45

Thr Gln Ala Val Cys Cys Glu Asp His Ile His Cys Cys Pro Ala Gly
        50                  55                  60

Phe Thr Cys Asp Thr Gln Lys Gly Thr Cys Glu
 65                 70                  75
```

```
<210> SEQ ID NO 5
<211> LENGTH: 81
<212> TYPE: PRT
<213> ORGANISM: Artificial Sequence
<220> FEATURE:
<223> OTHER INFORMATION: peptide derived from human GEP

<400> SEQUENCE: 5

Gln Gly Pro His Gln Val Pro Trp Met Glu Lys Ala Pro Ala His Leu
 1               5                  10                  15

Ser Leu Pro Asp Pro Gln Ala Leu Lys Arg Asp Val Pro Cys Asp Asn
            20                  25                  30

Val Ser Ser Cys Pro Ser Ser Asp Thr Cys Gln Leu Thr Ser Gly
         35                  40                  45

Glu Trp Gly Cys Cys Pro Ile Pro Glu Ala Val Cys Cys Ser Asp His
 50                  55                  60

Gln His Cys Cys Pro Gln Gly Tyr Thr Cys Val Ala Glu Gly Gln Cys
65                   70                  75                  80

Gln

<210> SEQ ID NO 6
<211> LENGTH: 98
<212> TYPE: PRT
<213> ORGANISM: Artificial Sequence
<220> FEATURE:
<223> OTHER INFORMATION: peptide derived from human GEP

<400> SEQUENCE: 6

Pro Gln Ala Ser Cys Cys Glu Asp Arg Val His Cys Cys Pro His Gly
 1               5                  10                  15

Ala Phe Cys Asp Leu Val His Thr Arg Cys Ile Thr Pro Thr Gly Thr
            20                  25                  30

His Pro Leu Ala Lys Lys Leu Pro Ala Gln Arg Thr Asn Arg Ala Val
         35                  40                  45

Ala Leu Ser Ser Ser Ala Ser Ser Lys Glu Asn Ala Thr Thr Asp Leu
 50                  55                  60

Leu Thr Lys Leu Pro Ala His Thr Val Gly Asp Val Lys Cys Asp Met
65                   70                  75                  80

Glu Val Ser Cys Pro Asp Gly Tyr Thr Cys Cys Arg Leu Gln Ser Gly
                 85                  90                  95

Ala Trp

<210> SEQ ID NO 7
<211> LENGTH: 103
<212> TYPE: PRT
<213> ORGANISM: Artificial Sequence
<220> FEATURE:
<223> OTHER INFORMATION: peptide derived from human GEP

<400> SEQUENCE: 7

Ser Lys Glu Asn Ala Thr Thr Asp Leu Leu Thr Lys Leu Pro Ala His
 1               5                  10                  15

Thr Val Gly Asp Val Lys Cys Asp Met Glu Val Ser Cys Pro Asp Gly
            20                  25                  30

Tyr Thr Cys Cys Arg Leu Gln Ser Gly Ala Trp Pro Trp Cys Glu Gln
         35                  40                  45

Gly Pro His Gln Val Pro Trp Met Glu Lys Ala Pro Ala His Leu Ser
 50                  55                  60

Leu Pro Asp Pro Gln Ala Leu Lys Arg Asp Val Pro Cys Asp Asn Val
65                   70                  75                  80
```

```
Ser Ser Cys Pro Ser Ser Asp Thr Cys Cys Gln Leu Thr Gly Glu
            85                  90                  95

Trp Gly Cys Cys Pro Ile Pro
            100
```

<210> SEQ ID NO 8
<211> LENGTH: 588
<212> TYPE: PRT
<213> ORGANISM: Mus musculus

<400> SEQUENCE: 8

```
Met Trp Ile Leu Val Ser Trp Leu Ala Leu Val Ala Arg Leu Val Ala
 1               5                  10                  15

Gly Thr Gln Cys Pro Asp Gly Gln Phe Cys Pro Val Ala Cys Cys Leu
             20                  25                  30

Asp Gln Gly Gly Ala Asn Tyr Ser Cys Cys Asn Pro Leu Leu Asp Thr
         35                  40                  45

Trp Pro Ile Ile Thr Ser Arg Arg Leu Asp Gly Ser Cys Gln Ile Arg
 50                  55                  60

Asp His Cys Pro Asp Gly Tyr Ser Cys Leu Leu Thr Val Ser Gly Thr
65                  70                  75                  80

Ser Ser Cys Cys Pro Phe Ser Glu Gly Val Ser Cys Asp Asp Gly Gln
                85                  90                  95

His Cys Cys Pro Arg Gly Phe His Cys Ser Ala Asp Gly Lys Ser Cys
            100                 105                 110

Ser Gln Ile Ser Asp Ser Leu Leu Gly Ala Val Gln Cys Pro Gly Ser
        115                 120                 125

Gln Phe Glu Cys Pro Asp Ser Ala Thr Cys Cys Ile Met Ile Asp Gly
    130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Ile Ser Pro Thr Gly Thr His Pro Leu Leu Lys Lys Phe Pro Ala
            180                 185                 190

Gln Arg Thr Asn Arg Ala Val Ala Ser Phe Ser Val Val Cys Pro Asp
        195                 200                 205

Ala Lys Thr Gln Cys Pro Asp Asp Ser Thr Cys Cys Glu Leu Pro Thr
    210                 215                 220

Gly Lys Tyr Gly Cys Cys Pro Met Pro Asn Ala Ile Cys Cys Ser Asp
225                 230                 235                 240

His Leu His Cys Cys Pro Gln Asp Thr Val Cys Asp Leu Ile Gln Ser
                245                 250                 255

Lys Cys Ile Ser Lys Asp Tyr Thr Thr Asp Leu Met Thr Lys Leu Pro
            260                 265                 270

Gly Tyr Pro Val Asn Glu Val Lys Cys Asp Leu Glu Val Ser Cys Pro
        275                 280                 285

Asp Gly Tyr Thr Cys Cys Arg Leu Asn Thr Gly Ala Trp Gly Cys Cys
    290                 295                 300

Pro Phe Thr Lys Ala Val Cys Cys Glu Asp His Ile His Cys Cys Pro
305                 310                 315                 320

Ala Gly Phe Gln Cys His Thr Glu Thr Gly Thr Cys Glu Leu Gly Val
                325                 330                 335

Leu Gln Val Pro Trp Met Lys Lys Val Thr Ala Ser Leu Ser Leu Pro
            340                 345                 350
```

```
Asp Pro Gln Ile Leu Lys Asn Asp Val Pro Cys Asp Phe Ser Ser
        355                 360                 365

Cys Pro Ser Asn Asn Thr Cys Cys Arg Leu Ser Ser Gly Asp Trp Gly
370                 375                 380

Cys Cys Pro Met Pro Glu Ala Val Cys Cys Leu Asp His Gln His Cys
385                 390                 395                 400

Cys Pro Gln Gly Phe Lys Cys Met Asp Glu Gly Tyr Cys Gln Lys Gly
                405                 410                 415

Asp Arg Met Val Ala Gly Leu Glu Lys Met Pro Val Arg Gln Thr Thr
            420                 425                 430

Leu Leu Gln His Gly Asp Ile Gly Cys Asp Gln His Thr Ser Cys Pro
        435                 440                 445

Val Gly Gln Thr Cys Cys Pro Ser Leu Lys Gly Ser Trp Ala Cys Cys
450                 455                 460

Gln Leu Pro His Ala Val Cys Cys Glu Asp Arg Gln His Cys Cys Pro
465                 470                 475                 480

Ala Gly Tyr Thr Cys Asn Val Lys Ala Arg Thr Cys Glu Lys Asp Ala
                485                 490                 495

Gly Ser Val Gln Pro Ser Met Asp Leu Thr Phe Gly Ser Lys Val Gly
            500                 505                 510

Asn Val Glu Cys Gly Ala Gly His Phe Cys His Asp Asn Gln Ser Cys
        515                 520                 525

Cys Lys Asp Ser Gln Gly Gly Trp Ala Cys Cys Pro Tyr Val Lys Gly
530                 535                 540

Val Cys Cys Arg Asp Gly Arg His Cys Cys Pro Ile Gly Phe His Cys
545                 550                 555                 560

Ser Ala Lys Gly Thr Lys Cys Leu Arg Lys Lys Thr Pro Arg Trp Asp
                565                 570                 575

Ile Leu Leu Arg Asp Pro Ala Pro Arg Pro Leu Leu
            580                 585
```

<210> SEQ ID NO 9
<211> LENGTH: 53
<212> TYPE: PRT
<213> ORGANISM: Artificial Sequence
<220> FEATURE:
<223> OTHER INFORMATION: consensus
<221> NAME/KEY: VARIANT
<222> LOCATION: (2)...(6)
<223> OTHER INFORMATION: Xaa can be any amiino acid
<221> NAME/KEY: VARIANT
<222> LOCATION: (7)...(7)
<223> OTHER INFORMATION: Xaa can be any amino acid or none
<221> NAME/KEY: VARIANT
<222> LOCATION: (9)...(13)
<223> OTHER INFORMATION: Xaa can be any amino acid
<221> NAME/KEY: VARIANT
<222> LOCATION: (16)...(23)
<223> OTHER INFORMATION: Xaa can be any amino acid
<221> NAME/KEY: VARIANT
<222> LOCATION: (26)...(31)
<223> OTHER INFORMATION: Xaa can be any amino acid
<221> NAME/KEY: VARIANT
<222> LOCATION: (34)...(34)
<223> OTHER INFORMATION: Xaa can be any amino acid
<221> NAME/KEY: VARIANT
<222> LOCATION: (36)...(37)
<223> OTHER INFORMATION: Xaa can be any amino acid
<221> NAME/KEY: VARIANT
<222> LOCATION: (42)...(45)
<223> OTHER INFORMATION: Xaa can be any amino acid
<221> NAME/KEY: VARIANT
<222> LOCATION: (47)...(51)
<223> OTHER INFORMATION: Xaa can be any amino acid

```
-continued

<221> NAME/KEY: VARIANT
<222> LOCATION: (52)...(52)
<223> OTHER INFORMATION: Xaa can be any amino acid or none

<400> SEQUENCE: 9

Cys Xaa Xaa Xaa Xaa Xaa Xaa Cys Xaa Xaa Xaa Xaa Xaa Cys Cys Xaa
  1               5                  10                  15

Xaa Xaa Xaa Xaa Xaa Xaa Xaa Cys Cys Xaa Xaa Xaa Xaa Xaa Xaa Cys
             20                  25                  30

Cys Xaa Asp Xaa Xaa His Cys Cys Pro Xaa Xaa Xaa Xaa Cys Xaa Xaa
         35                  40                  45

Xaa Xaa Xaa Xaa Cys
     50

<210> SEQ ID NO 10
<211> LENGTH: 10
<212> TYPE: PRT
<213> ORGANISM: Artificial Sequence
<220> FEATURE:
<223> OTHER INFORMATION: consensus
<221> NAME/KEY: VARIANT
<222> LOCATION: (3)...(3)
<223> OTHER INFORMATION: Xaa can be any amino acid
<221> NAME/KEY: VARIANT
<222> LOCATION: (5)...(6)
<223> OTHER INFORMATION: Xaa can be any amino acid

<400> SEQUENCE: 10

Cys Cys Xaa Asp Xaa Xaa His Cys Cys Pro
  1               5                  10
```

PEPTIDES TARGETING TNF FAMILY RECEPTORS AND ANTAGONIZING TNF ACTION, COMPOSITIONS, METHODS AND USES THEREOF

CROSS-REFERENCE TO RELATED APPLICATIONS

The present application is a non-provisional application claiming the priority of copending provisional application Ser. No. 61/212,971, filed Apr. 17, 2009, the disclosure of which is incorporated by reference herein in its entirety. Applicants claim the benefits of this application under 35 U.S.C. §119 (e).

GOVERNMENTAL SUPPORT

This invention was made with government support under NIH/NIAMS1 K01 AR053210 and NIH/NIA 1 R03 AG029388, awarded by the National Institute of Health, National Institute of Arthritis and Musculoskeletal and Skin Diseases. The government has certain rights in the invention.

FIELD OF THE INVENTION

The present invention relates generally to modulators of TNF/TNFR, particularly peptides and their derivatives which antagonize TNF and TNF/TNFR-mediated responses, activity or signaling. The invention also relates to methods of antagonizing TNF and the modulation of TNF-mediated diseases or responses, including inflammatory diseases and conditions.

BACKGROUND OF THE INVENTION

In the progress of arthritis, synovium, cartilage, and bone are all sites of increased production of growth factors, cytokines, and inflammatory mediators that are believed to contribute to pathogenesis [1, 2]. Although both bone and synovium have important roles in the pathogenesis of arthritis [1, 3], most efforts at developing disease-modifying treatments have focused on the molecular events within cartilage. Arthritic chondrocytes undergo a series of complex changes, including proliferation, catabolic alteration, and, ultimately, death. The regulation of these phenotypic changes at different stages of disease is under intensive study, with focus on the biomechanical and biochemical signals that regulate each of these discrete chondrocyte responses [2, 4]. Chondrocytes themselves are major protagonists in this regulatory cascade—not just the target of external biomechanical and biochemical stimuli, but themselves the source of cytokines, proteases, and inflammatory mediators that promote the deterioration of articular cartilage [1, 2]. Pathogenic molecules produced by arthritic chondrocytes include tumor necrosis factor (TNF), interleukin-1 (IL-1), IL-6, IL-8, matrix metalloproteinases (MMPs), ADAMTSs, nitric oxide, prostaglandins, and leukotrienes [2, 4]. There is also evidence that arthritic chondrocytes exhibit increased anabolic activity, including increased release of growth factors and synthesis of type II collagen, proteoglycan, and other extracellular matrix proteins, as well as the expression of genes associated with the chondroprogenitor hypertrophic phenotype [5-7].

A great deal of research in rheumatology over the past two decades has focused on identifying cytokines and mediators responsible for the inflammatory and degenerative processes in rheumatoid arthritis (RA), with the aim of developing specific antagonists of therapeutic value. Among all factors, TNF-a has received the greatest attention because of its position at the apex of the pro-inflammatory cytokine cascade, and its dominance in the pathogenesis of RA. Many lines of evidence support this theory including: (1) TNF-a is expressed at high levels in inflamed synovium and cartilage from RA patients; (2) anti-TNF-a inhibits the production of other pro-inflammatory cytokines including IL-1; and (3) TNF-a can induce joint inflammation, trigger cartilage destruction by inducing metalloproteinase, and stimulate osteoclastogenesis and bone resorption. Most importantly, anti-TNF therapies for RA have shown remarkable results by decreasing inflammation, improving patient function and vitality, and attenuating cartilage and bone erosions. There are now three anti-TNF treatments via targeting to TNF ligand, etanercept (Enbrel, a soluble TNFR2-IgG1 fusion protein), infliximab (Remicade, a chimeric monoclonal antibody against TNF-a), and adalimumab (a humaneric monoclonal antibody against TNF-a) that have been used clinically for treating various kinds of inflammatory diseases, including rheumatoid arthritis. Engineered proteins/peptides are now providing a new wave of therapeutic products. Indeed, designed protein/peptide therapeutic agents now outnumber and surpass the number of new small-molecule drugs approved annually by the FDA. Antibodies and immunoadhesins that directly target cytokines for their systemic removal (ligand ablation) have become an effective therapeutic strategy (e.g. etanercept, adalimumab and infliximab), and in some indications the selective targeting of cytokine receptors (e.g. anakinra) can deliver a highly effective clinical outcome.

Granulin/epithelin precursor (GEP), also known as PC-cell-derived growth factor (PCDGF), acrogranin, progranulin (PGRN), proepithelin (PEPI), or GP80, was first purified as a growth factor from conditioned tissue culture media [8, 9, 65, 66, 67]. GEP is a 593-amino-acid secreted glycoprotein with an apparent molecular weight of 80 kDa [10, 14], which acts as an autocrine growth factor. GEP contains seven and a half repeats of a cysteine-rich motif ($CX_{5-6}CX_5CCX_8CCX_6CCXDX_2HCCPX_4CX_{5-6}C$) (SEQ ID NO: 9) in the order P-G-F-B-A-C-D-E, where A-G are full repeats and P is the half motif (FIG. 1). The C-terminal region of the consensus sequence contains the conserved sequence $CCXDX_2HCCP$ (SEQ ID NO: 10) and is suggested to have a metal binding site and to be involved in regulatory function [15]. Notably, GEP undergoes proteolytic processing with the liberation of small, 6-kDa repeat units known as granulins (or epithelins), which retain biological activity [16]: peptides are active in cell growth assays [13] and may be related to inflammation [17].

GEP is abundantly expressed in rapidly cycling epithelial cells, in cells of the immune system, and in neurons [10-12, 17]. High levels of GEP expression are also found in several human cancers and contribute to tumorigenesis in diverse cancers, including breast cancer, clear cell renal carcinoma, invasive ovarian carcinoma, glioblastoma, adipocytic teratoma, and multiple myeloma [16, 18-24]. Although GEP mainly functions as a secreted growth factor, it was also found to be localized inside cells and to directly modulate intracellular activities [12, 25-27]. The role of GEP in the regulation of cellular proliferation has been well characterized using mouse embryo fibroblasts derived from mice with a targeted deletion of the insulin-like growth factor receptor (IGF-IR) gene (R-cells). These cells are unable to proliferate in response to IGF-1 and other growth factors (EGF and PDGF) necessary for progression through the cell cycle [28]. In contrast, GEP is the only known growth factor able to bypass the requirement for the IGF-IR, thus promoting cell growth of R-cells [13, 29]. Increasing evidence has also implicated GEP in the regulation of differentiation, development and pathological processes. It has been isolated as a differentially-expressed gene from mesothelial differentiation [30], sexual differentiation of the brain [31], macrophage development [32], and synovium of rheumatoid arthritis and osteoarthritis [33]. GEP was also shown to be a crucial mediator of wound response and tissue repair [21, 34]. It was reported that mutations in GEP cause tau-negative frontotemporal dementia linked to chromosome 17 [35-38]. The mode of action of GEP remains largely unknown. Several GEP-associated proteins have been reported to affect GEP action in various processes. One example is the secretory leukocyte protease inhibitor (SLPI). Elastase digests GEP exclusively in the intergranulin linkers, resulting in the generation of granulin peptides, suggesting that this protease may be an important GEP convertase. SLPI blocks this proteolysis either by directly binding to elastase or by sequestering granulin peptides from the enzyme [34]. GEP can modulate transcriptional activities by interacting with human cyclin T1 [26] and Tat-P-TEFb [25]. GEP was also found to interact with perlecan, a heparan sulfate proteoglycan; perlecan-null mice exhibit severe skeletal defects [19, 39-41].

The Tumor Necrosis Factor (TNF) family of cytokines plays an essential role in multiple biological functions including inflammation, organogenesis, host defense, autoimmunity, and apoptosis. The action of these potent biological mediators is achieved through a receptor-ligand interaction, leading to intracellular signaling and a change in cellular phenotype. The ligands exert their function by forming trimers and binding to their corresponding receptors. Subsequent receptor oligomerization results in conformational change of the receptor's intracellular domain, which then allows for members of the TNF receptor-associated factor (TRAF) family of adaptor proteins to bind and initiate a signaling cascade. TNFR2, TNFR1, TrkA, NGFR, CD 40, CD 30, OX-40, DR5, DR3, DR4 and RANK include some of the members of TNF receptor super-family that interact with different TRAF molecules (including 1-6) (Lewit-Bentley, A., et al., J. Mol. Biol. 199:389-392 (1988), Banner, D. W., et al., Cel. 73:431-445 (1993), Karpusas, M., et al., Structure. 3:1031-1039 (1995), Hymowitz, S. G., et al., Mol. Cell. 4:563-571 (1999), Mongkilsapaya, J., et al., Nat. Struc. Biol. 6:-1048-1053 (1999), Cha, S. S., et al., J. Biol. Chem. 275:31171-31177 (2000)).

Both TNF receptors (TNFR1 and TNFR2) are ubiquitously expressed in cells and interact with their cognate ligand: TNFα, a central proinflammatory cytokine [42-44]. It is widely accepted that TNFα serves very important functions in pathophysiology, being a factor that interferes strongly with the cell growth, differentiation and death. TNF appears not only to orchestrate acute responses to infection and immunological injury but also to act as a balancing factor required for the re-establishment of physiological homeostasis and regulation [45]. TNFα has been found to affect skeletal development: its level is increased in most inflammatory diseases known to affect longitudinal growth in children [46, 47] and catch-up growth was shown in children with refractory juvenile idiopathic arthritis treated with the TNF antagonist etanercept (Enbrel) [46, 47]; TNFα regulates growth plate chondrocytes and suppress longitudinal growth in metatarsal organ cultures [48].

Arthritis is a degenerative joint disease, occurring primarily in the senior population, that currently affects more than 46,000,000 individuals in the United States. Typical clinical symptoms are pain and stiffness, particularly after prolonged activity. In industrialized societies arthritis is the leading cause of physical disability, increased health care usage, and impaired quality of life. The impact of arthritic conditions is expected to grow as the population both increases and ages in the coming decades. Despite the prevalence of arthritic diseases, their precise etiology, pathogenesis, and progression remain beyond our understanding. Evidence is accumulating that demonstrates the significance of inflammatory cytokines and growth factors in the pathological processes of arthritis. The destruction of the extracellular matrices of articular cartilage and bone in arthritic joints is thought to be mediated by excessive cytokine activities and imbalance between inflammatory cytokines and their physiological antagonists. The isolation of the growth factors that regulates chondrocytes and arthritis, and the inhibitors that antagonize the actions of cytokines, are therefore of great importance from both a pathophysiological and a therapeutic standpoint. We have previously identified granulin/epithelin precursor (GEP) as a novel chondrogenic growth factor that plays an essential role in cartilage formation (Xu, K et al (2007) J Biol Chem 282 (15):11347-11355; WO 2008/094687 A2).

There still exists a need in the art for a better and more complete understanding of the process of and, thereby, intervention for, inflammatory diseases and conditions, particularly TNF family member mediated processes and conditions. Thus, the purpose of this invention is to extend our understanding of the molecular mechanisms by which growth factors and cytokines control cartilage development and arthritis, and to mediators thereof for development of new anti-TNF/TNFR therapeutic interventions for various kinds of TNF-related diseases, including inflammatory arthritis.

The citation of references herein shall not be construed as an admission that such is prior art to the present invention.

SUMMARY OF THE INVENTION

Taking into account the biological properties of GEP, it has been hypothesized that GEP could act through "classic" membrane receptor(s), as do other known growth factors. Thus far, a functional receptor has not been identified. Our functional genetic screen described herein led to the isolation of TNF receptors as novel GEP-binding receptors. Our studies demonstrate that GEP (Granulin/epithelin precursor) is the first growth factor that directly targets to TNF receptors (TNFR). Thus GEP and its derived peptide(s) represent a novel anti-TNF/TNFR signaling blocker by acting on the cytokine receptors.

The studies described herein demonstrate that GEP is a novel antagonist of TNF/TNFR signaling. The present findings reveal that: 1) GEP directly binds to TNF receptors in a dose-dependent manner; 2) Blocking TNF receptors by neutralizing antibodies or recombinant extracellular domains abolishes GEP function in stimulation of cell proliferation; 3) GEP potently activates Erk1/2 signaling, and moderately Akt pathway; 4) GEP activates genes known to be the downstream molecules of the TGFβ subfamily, including BMP2; in addition, GEP-mediated inductions of these gene expressions depend on TNF receptors; 5) GEP is an arthritis-responsive gene and its level was significantly elevated in patients with arthritis; 6) GEP, as an antagonist of TNFα, dramatically reduces inflammation response and apoptosis induced by TNFα; and 7) importantly, GEP exhibits better (at least as good as) inhibition of TNF-stimulated inflammation than Enbrel and Remicade that have been used clinically for treating various kinds of inflammatory diseases and conditions, including rheumatoid arthritis. These findings reveal that GEP is a novel naturally-occurring antagonist of TNF/TNFR signaling via directly targeting to TNF receptors.

The invention provides GEP and GEP peptides, particularly including the peptide(s) denoted atsttrin, as modulators of TNF/TNFR activity and signaling, particularly inhibiting or blocking TNF-mediated signaling or response, particularly as antagonists of TNF/TNFR.

The invention provides peptides which antagonize TNF family member receptors, particularly TNFR, and block, inhibit, reduce, or prevent TNF family member signaling, including TNF/TNFR signaling. The invention provides peptides which antagonize TNF family member receptors, particularly RANK, and block, inhibit, reduce, or prevent TNF family member signaling, including RANK/RANKL signaling.

In a particular embodiment, the present invention relates to all members of the herein disclosed family of GEP peptides and of atsttrin, which are capable of modulating, particularly antagonizing, TNF family/receptor signaling and response, particularly TNF/TNFR signaling and response. The family of peptides includes fragments or portions, including mixed portions of GEP sequence and half units, particularly comprising one or more granulin unit and one or more linker unit of GEP. In one aspect the peptide comprises two or more half units of granulin units and one or more linker unit of GEP.

In a particular aspect of the invention, the GEP peptide comprises the peptide atsttrin, comprising combinations of half units of granulin units A, C and F in combination with linker units P3, P4 and P5. In a particular aspect, the GEP peptide comprises a combination of half units of granulin units, wherein at least one half unit is ½F, and linker units, particularly at least two linker units. In a further particular aspect atsttrin has the amino acid sequence set out in FIG. 24 and comprises granulin units and linker units ½F-P3-P4-½A-P5-½C, including as set out in SEQ ID NO: 2.

The present invention naturally contemplates several means for preparation of the GEP peptides and/or atsttrin of the present invention, including as illustrated herein and/or using known recombinant techniques, and the invention is accordingly intended to cover such synthetic preparations within its scope. The determination of the antagonist amino acid sequences disclosed herein facilitates the reproduction of the peptides by any of various synthetic methods or any known recombinant techniques, and accordingly, the invention extends to expression vectors comprising nucleic acid encoding the peptides of the present invention for expression in host systems by recombinant DNA techniques, and to the resulting transformed hosts.

The present invention also relates to a recombinant DNA molecule, recombinant nucleic acid, or cloned gene, or a degenerate variant thereof, preferably a nucleic acid molecule, in particular a recombinant DNA molecule or cloned gene, encoding the amino acid of one or more GEP peptides shown in FIG. 24 or variants thereof. In a particular embodiment, the recombinant DNA molecule, recombinant nucleic acid, or a degenerate variant thereof, preferably a nucleic acid molecule, encodes a GEP peptide capable of antagonizing TNF/TNFR, which comprises one or more granulin unit and one or more linker unit of GEP as depicted in FIG. 1 and as set out in the sequence of GEP of FIG. 23. In a further particular embodiment, the recombinant DNA molecule, recombinant nucleic acid, or a degenerate variant thereof, preferably a nucleic acid molecule, encodes a GEP peptide atsttrin capable of antagonizing TNF/TNFR as set out in FIG. 24 and comprising granulin units and linker units ½F-P3-P4-½A-P5-½C (SEQ ID NO: 2).

It is an object of the present invention to provide pharmaceutical compositions for use in therapeutic methods which comprise or are based upon the GEP peptides and/or atsttrin.

The pharmaceutical compositions include combinations of one or more GEP peptides and/or atsttrin having TNF antagonistic activity. The pharmaceutical compositions include combinations of one or more GEP peptides and/or atsttrin having TNF antagonistic activity and one or more inflammatory mediator. Inflammatory mediators include and may be selected from non-steroidal anti-inflammatory agents (NSAIDs), steroids, corticosteroids, other TNF antagonists (e.g. etanercept, adalimumab and infliximab), and cytokine receptor antagonists (e.g. anakinra). The pharmaceutical compositions include combinations of one or more GEP peptides and/or atsttrin having TNF antagonistic activity and one or more inflammatory mediator, immunododulatory agent, or anti-cancer agent.

In a further embodiment, the present invention relates to certain therapeutic methods which would be based upon the TNF/TNFR antagonistic activity of GEP, GEP peptides and/or atsttrin, or active fragments thereof, or upon agents or other drugs determined to possess the same activity. Thus, the present invention provides methods of preventing and/or treating diseases mediated by TNF/TNFR activity and/or which are facilitated or induced by TNF family ligand/receptor activity and/or characterized by inflammation. The invention provides methods of treatment, alleviation, or prevention of TNF-mediated diseases and inflammatory conditions or immunological conditions, including rheumatoid arthritis, osteoarthritis, ankylosing spondylitis, psoriasis, inflammatory bowel diseases, Chrohn's disease, ulcerative colitis, uveitis, inflammatory lung diseases, chronic obstructive pulmonary disease.

In one aspect, the invention provides a method for treatment, alleviation or prevention of tumors or cancer which are mediated by GEP, TNF, GEP/TNFR and/or TNF/TNFR. Thus, it is contemplated that a tumor, cancerous or precancerous condition wherein the growth and/or proliferation of the tumor or cancerous/precancerous cells are dependent on or facilitated by GEP, TNF, GEP/TNFR and/or TNF/TNFR activity or signaling may be sensitive to the TNF/GEP antagonist peptide(s) of the present invention. The invention further contemplates use and application of GEP peptides, particularly including atsttrin to inhibit or block GEP-mediated cancer or cell proliferation.

More specifically, the therapeutic method provides for methods for the treatment, prevention or alleviation of diseases mediated by TNF/TNFR activity and/or which are facilitated or induced by TNF family ligand/receptor activity and/or characterized by inflammation by the administration of pharmaceutical compositions that comprise effective antagonists of TNF based on GEP, GEP peptides and/or atsttrin or its subunits, or other equally effective drugs developed for instance by a drug screening assay prepared and used in accordance with a further aspect of the present invention. In a particular aspect, GEP, GEP peptides, and/or atsttrin may be administered to treat, alleviate, or prevent a TNF/TNFR mediated disease or condition or an inflammatory disease or condition.

In a further aspect, GEP, GEP peptides and/or atsttrin or its subunits may be utilized in methods to modulate, prevent, treat or alleviate immunological injuries, including allergies, auto-immune diseases and other such immune conditions, particularly wherein TNF/TNFR is involved or implicated. Thus, immune and/or inflammatory responses in auto-immune, allergies or other such immunological conditions may be modulated by GEP, GEP peptides and/or atsttrin or its subunits. In one such aspect, auto-immune diseases, such as lupus and multiple sclerosis, may be modulated, alleviated or treated by GEP, GEP peptides and/or atsttrin or its subunits.

In particular, the GEP, GEP peptides, atsttrin peptides of the present invention, including as described herein and provided in FIGS. 23 and 24 herein, their antibodies, agonists, mimics, or active fragments thereof, could be prepared in pharmaceutical formulations for administration in instances wherein anti-TNF or TNF/TNFR family antagonist activity and/or therapy is appropriate, such as to treat or alleviate a TNF/TNFR mediated condition or inflammation. The GEP, GEP peptides and atsttrin peptides include exemplary GEP as set out in SEQ ID NO: 1 and 8, and GEP peptides or atsttrin peptides as set out in SEQ ID NO: 2 and 3-7, and variants or subunits thereof. The specificity of the GEP peptides and/or atsttrin hereof would make it possible to better manage the aftereffects of current anti-TNF and/or anti-inflammatory therapy, and would thereby make it possible to apply broadly as a general anti-TNF and/or anti-TNF family agent.

The invention includes an assay system for screening of potential drugs or compounds effective to modulate TNF/TNFR activity of target mammalian cells by mimicking the activity of the GEP peptides. This aspect includes assays to screen for additional active GEP fragments, granulin/linker unit combinations, derivatives, variants and amino acid modifications effective to modulate TNF/TNFR activity in a like manner to GEP and atsttrin peptide. In one instance, the test drug or compound is administered to a cellular sample with TNFα to activate TNF/TNFR activity, to determine the effect of the test drug or compound upon TNFα activity, by comparison with a control, including wherein the control is GEP, active GEP peptide(s), atsttrin.

In an assay, a control quantity of the GEP, GEP peptides, atsttrin, TNFα, TNFR, or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Other objects and advantages will become apparent to those skilled in the art from a review of the following description which proceeds with reference to the following illustrative drawings.

BRIEF DESCRIPTION OF THE DRAWINGS

FIG. 23 provides the amino acid sequence of human GEP (SEQ ID NO: 1) which is 593 amino acids.

FIG. 24 depicts the sequence of atsttrin peptide (SEQ ID NO: 2), and sequences of various other tested peptides (SEQ ID NOS: 3-7, respectively).

FIGS. 25A and 25B depicts the (A) structure and (B) amino acid sequence of mouse GEP (SEQ ID NO: 8). In (B), the granulin units GrnA, GrnC, GrnD and GrnE are underlined and indicated at each unit.

FIGS. 30A and 30B depicts Severity (A) (by clinical score) and Incidence (B) of arthritis in CIA mice treated with PBS (n=10), Atsttrin (n=10), or Enbrel (n=10).

FIGS. 32A and 32B depict (A) sections of each ankle of PBS-treated and Atsttrin-treated animals stained with H&E or Safranin-O as indicated. In the H&E panel, arrows indicate tissue destruction and cell infiltration, respectively. In the Sarfanin-O panel, arrows indicate loss of matrix staining. (B) shows MicroCT images of the ankle of PBS-treated and Atsttrin-treated animals.

FIG. 33 provides TRAP staining images in PBS-treated and Atsttrin-treated animals. TRAP+ osteoclasts are depicted in red staining in the PBS-treated animal but are hardly detectable in the Atsttrin-treated animal. Different magnifications are depicted for visual emphasis.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

Figure 15:
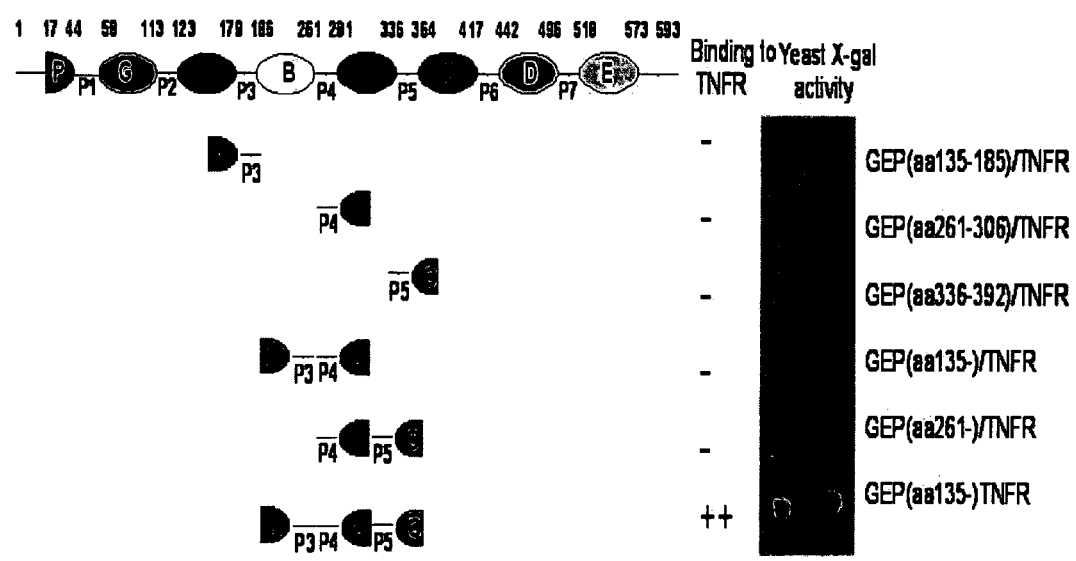
FIG. 15 (Left) Schematic diagram of GEP constructs used to map those of its fragments that bind to TNFR. (Right) β-Galactosidase assays.

The terms "Atsttrin", "Antagonist of TNF/TNFR Signaling via Targeting TNF Receptors", "atsttrin peptide", "TNF antagonist peptide" and any variants not specifically listed, may be used herein interchangeably, and as used throughout the present application and claims refer to peptides including single or multiple proteins, particularly which are derived from or fragments of GEP and extends to those proteins having the amino acid sequence data described herein and presented in FIG. 24 and also diagrammed in FIG. 15, and the profile of activities and capabilities described and set forth herein and provided in the Claims. Active GEP peptides having activity as antagonist of TNF/TNFR signaling and capable of binding one or more TNF receptors, such as TNFα, are included and provided herein. The full length sequence of human GEP is provided in FIG. 23. The full length sequence of mouse GEP is provided in FIG. 25. Thus, TNF antagonist peptides derived from GEP sequences(s) or comprising GEP sequence(s) and having TNF and/or TNF-family antagonist activity are encompassed herein. These atsttrin peptides include and encompass fragments, variants, and derivatives of the peptides. Accordingly, proteins displaying substantially equivalent activity, and which are modifications thereof, are likewise contemplated. These modifications may be deliberate, for example, such as modifications obtained through site-directed mutagenesis, or may be accidental, such as those obtained through mutations in hosts that are producers of the complex or its named subunits. Corresponding mouse or other species or ortholog GEP sequences to the human atsttrin and active GEP peptide sequences are further contemplated. Also, the terms "Atsttrin", "Antagonist of TNF/TNFR Signaling via Targeting TNF Receptors", "atsttrin peptide", "TNF antagonist peptide" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired fuctional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. It should be appreciated that also within the scope of the present invention are DNA sequences encoding which code for a having the same amino acid sequence as SEQ ID NO:, but which are degenerate to SEQ ID NO:. By "degenerate to" is meant that a different three-letter codon is used to specify a particular amino acid. It is well known in the art that certain codons can be used interchangeably to code for each specific amino acid. For example, and not by limitation, Leucine (Leu or L) may be encoded by any of UUA or UUG or CUU or CUC or CUA or CUG, and Serine (Ser or S) may be encoded by any of UCU or UCC or UCA or UCG or AGU or AGC. It should be understood that these exemplary codons specified are for RNA sequences. The corresponding codons for DNA have a T substituted for U.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^N$C below the predicted or determined $T_m$ with washes of higher stringency, if desired.

As used herein, "pg" means picogram, "ng" means nanogram, "ug" or "µg" mean microgram, "mg" means milligram, "ul" or "µl" mean microliter, "ml" means milliliter, "l" means liter.

Mutations can be made in GEP, GEP peptides, and/or atsttrin such an amino acid is substituted or modified or such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein or peptide. The present invention should be considered to include sequences containing conservative and/or non-conservative changes which do not significantly alter the activity or binding characteristics of the resulting protein or peptide.

The following is one example of various groupings of amino acids:

Amino acids with nonpolar R groups: Alanine, Valine, Leucine, Isoleucine, Proline, Phenylalanine, Tryptophan, Methionine Amino acids with uncharged polar R groups: Glycine, Serine, Threonine, Cysteine, Tyrosine, Asparagine, Glutamine Amino acids with charged polar R groups (negatively charged at Ph 6.0): Aspartic acid, Glutamic acid Basic amino acids (positively charged at pH 6.0): Lysine, Arginine. Histidine (at pH 6.0)

Another grouping may be those amino acids with phenyl groups: Phenylalanine, Tryptophan, Tyrosine.

Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces turns in the protein's structure.

Two amino acid sequences are "substantially homologous" when at least about 70% of the amino acid residues (preferably at least about 80%, and most preferably at least about 90 or 95%) are identical, or represent conservative substitutions.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The term "therapeutically effective amount" means that amount of a drug, compound, peptide, or pharmaceutical agent that will elicit the biological or medical response of a subject that is being sought by a medical doctor or other clinician. The phrase "therapeutically effective amount" is used herein to include an amount sufficient to prevent, and preferably reduce by at least about 30 percent, more preferably by at least 50 percent, most preferably by at least 90 percent, a clinically significant change in the S phase activity of a target cell or cellular mass, or other feature of pathology such as for example, elevated blood pressure, fever or white cell count as may attend its presence and activity.

The term "preventing" or "prevention" refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term "prophylaxis" is related to and encompassed in the term "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term "subject" includes humans and other mammals.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease.

The term "disease characterized by inflammation", "inflammatory disease" refers to a disease which involves, results at least in part from, or includes inflammation. The term includes, but is not limited to, exemplary diseases selected from rheumatoid arthritis, osteoarthritis, ankylosing spondylitis, juvenile idiopathic arthritis, psoriasis, inflammatory bowel diseases, Chrohn's disease, ulcerative colitis, uveitis, inflammatory lung diseases, chronic obstructive pulmonary disease.

The term "inflammatory mediators" refers to mediators which enhance, initiate or facilitate an inflammatory reaction or an inflammatory response, and may be selected from the following: Cytokines (e.g. TNFalpha, IL3, IL4, IL5, IL13, GM-CSF), chemokines (e.g. MDC, CCL19, CCL20, CCL21, MIP-1alpha), Prostaglandins (e.g. PGD2), Leukotrienes (e.g. LTB4, LTC4, LTD4), metalloproteases, chymase, tryptase, growth factors (e.g. VEGF).

Despite the prevalence of arthritic diseases, their precise etiology, pathogenesis, and progression remain beyond our understanding. Evidence is accumulating that demonstrates the significance of inflammatory cytokines and growth factors in the pathological processes of arthritis. The isolation of the growth factors that regulate chondrocytes and arthritis, and inhibitors that antagonize the actions of cytokines, are therefore of great importance from both a pathophysiological and a therapeutic standpoint. Granulin/epithelin precursor (GEP) has been previously recognized as a novel chondrogenic growth factor that plays an essential role in cartilage formation, including as described in WO 2008/094687 A2 and by Liu and colleagues (Xu, K et al (2007) J Biol Chem 282(15):11347-11355).

The present invention demonstrates that the growth factor GEP directly associates with TNF receptors and acts as a naturally-occurring antagonist of TNFα, the central inflammatory cytokine in arthritis. Thus, the purpose of this invention is to extend the understanding of the molecular mechanisms by which growth factors and cytokines control cartilage development and arthritis, and to provide GEP, particularly its derived and active peptide(s), particularly atsttrin, and/or derivatives or variants thereof as novel anti-TNF/TNFR modulators. Atsttrin is demonstrated herein to bind and antagonize TNF, and alter TNF/TNFR signaling. GEP is demonstrated herein to bind RANK a TNF family member. Thus, GEP, GEP peptides, and/or atsttrin are applicable and useful in therapeutic interventions for various kinds of TNF-related diseases, including inflammatory conditions such as arthritis, bone diseases, and cancer conditions, such as osteoarthritis, osteoporosis, and osteosarcoma.

In vivo animal models of TNF/TNFR family mediated diseases or conditions may be utilized by the skilled artisan to further or additionally evaluate, assess, screen and/or verify the GEP, GEP peptides and/or atsttrin of the invention or agents or compounds identified in or in accordance with the present invention, including further assessing TNF/TNFR modulation in vivo. Animal models are readily available to demonstrate the applicability of recombinant GEP and GEP-derived peptide(s), atsttrin in mediating, alleviating or controlling the development and progression of TNF/TNFR mediated diseases or conditions, inflammatory conditions, immune diseases or conditions (including allergies an auto-immune diseases), bone diseases or conditions, or other possible targeted conditions. Animal models or studies include those described and detailed herein and in the examples. TNFα transgenic mice develop arthritis and provide a useful tool for evaluating the efficacy of novel therapeutic strategies for rheumatoid arthritis. Animal models include, but are not limited to, ulcerative colitis models, multiple sclerosis models (including EAE, lysolecithin-induced), arthritis models, allergic asthma models, airway inflammation models, psoriasis models, and acute inflammation models. The EAE animal model of multiple sclerosis provides an acute or chronic-relapsing, acquired, inflammatory and demyelinating autoimmune disease. Allergy models may be utilized as models of immunological injury and conditions. Osteoarthritis models include for example experimental osteoarthritis induced in rabbits after sectioning of the knee anterior cruciate ligament and in rats after tear of the medial collateral ligament. Appropriate bone disease, bone injury, and/or osteoporosis models are also known and available to one of skill in the art.

The invention includes use and applications of GEP, GEP peptides, atsttrin, and/or derivatives thereof for prevention, treatment or alleviation of rheumatoid arthritis and osteoarthritis. The invention includes use and applications of GEP, GEP peptides, atsttrin, and/or derivatives thereof for prevention, treatment or alleviation of TNF-related diseases, including inflammatory conditions, immune conditions including auto-immune diseases, bone diseases and cancer. TNF-related diseases include rheumatoid arthritis, osteoarthritis, ankylosing spondylitis, psoriasis, inflammatory bowel diseases, Chrohn's disease, ulcerative colitis, uveitis, inflammatory lung diseases, chronic obstructive pulmonary disease, multiple sclerosis, osteoporosis, osteosarcoma. The invention includes use and applications of GEP, GEP peptides, atsttrin, and/or derivatives thereof for prevention, treatment or alleviation of and/or for specific therapeutic intervention of inflammatory disorders by delivering precisely the required anti-TNF/TNFR effect. The invention includes use and applications of GEP, GEP peptides, atstrrin, and/or derivatives thereof for facilitating or mediating tissue repair. The invention includes use and applications of GEP, GEP peptides, atsttrin, and/or derivatives thereof for prevention, treatment or alleviation of immunological injury and conditions, including allergies and auto-immune diseases, such as lupus and multiple sclerosis. The invention includes use and applications of GEP, GEP peptides, atsttrin, and/or derivatives thereof for prevention, treatment or alleviation of cancer and tumor or cancer cell growth, including in GEP and/or TNF/TNFR mediated cancers or other such hyperproliferative disorders.

The possibilities both diagnostic and therapeutic that are raised by the existence of TNF antagonist peptides, including GEP, GEP peptides and/or atsttrin as described herein, derive from the fact that the peptides participate in direct and causal protein-protein interaction with TNF and serve to block, inhibit, antagonize, interfere with TNF/TNFR activity and/or signaling. Thus, the present invention contemplates pharmaceutical intervention in the cascade of reactions in which TNF/TNFR and/or TNF family/TNF family R is implicated, to modulate the activity, signal(s), and/or conditions initiated, facilitated or mediated thereby, including but not limited to inflammatory diseases and conditions.

The GEP, GEP peptides and/or atsttrin as described herein or other ligands or agents exhibiting either mimicry therewith or cognate TNF antagonism, may be prepared in pharmaceutical compositions, with a suitable carrier and at a strength effective for administration by various means to a patient experiencing an adverse medical condition associated with TNF/TNFR signaling, such as an inflammatory condition or disease. A variety of administrative techniques may be utilized, among them parenteral techniques such as subcutaneous, intravenous and intraperitoneal injections, catheterizations and the like. Average quantities of the GEP, GEP peptides and/or atsttrin as described herein or their subunits may vary and in particular should be based upon the recommendations and prescription of a qualified physician or veterinarian.

Also, antibodies including both polyclonal and monoclonal antibodies, and drugs that modulate the production or activity of the GEP, GEP peptides and/or atsttrin as described herein and/or their subunits may possess certain diagnostic applications and may for example, be utilized for the purpose of detecting and/or measuring conditions such as TNF-mediated diseases, inflammatory conditions, infections, cancer, or the like. For example, the GEP peptides and/or atsttrin may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the GEP, GEP peptides and/or atsttrin as described herein of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Preferably, the anti-GEP, GEP peptides and/or atsttrin antibody used in the diagnostic methods of this invention is an affinity purified polyclonal antibody. More preferably, the antibody is a monoclonal antibody (mAb). In addition, it is preferable for the anti-GEP, GEP peptides and/or atsttrin antibody molecules used herein be in the form of Fab, Fab', F(ab)$_2$ or F(v) portions of whole antibody molecules.

The present invention further contemplates therapeutic compositions useful in practicing the therapeutic methods of this invention. A therapeutic composition includes a biologically compatible composition. A subject therapeutic composition includes, in admixture, a pharmaceutically acceptable excipient (carrier) and one or more of a GEP, GEP peptide(s) and/or atsttrin polypeptide analog thereof or fragment thereof, as described herein as an active ingredient. In a preferred embodiment, the composition comprises the present GEP, GEP peptide(s) and/or atsttrin, and may comprise composition comprising one or more GEP granulin and one or more linker unit, or any one or more of the GEP peptide(s) or atsttrin, including as set out in the figures herein, including FIGS. 23 and 24 and as provided in SEQ ID NOS: 1-8.

Figure 34:
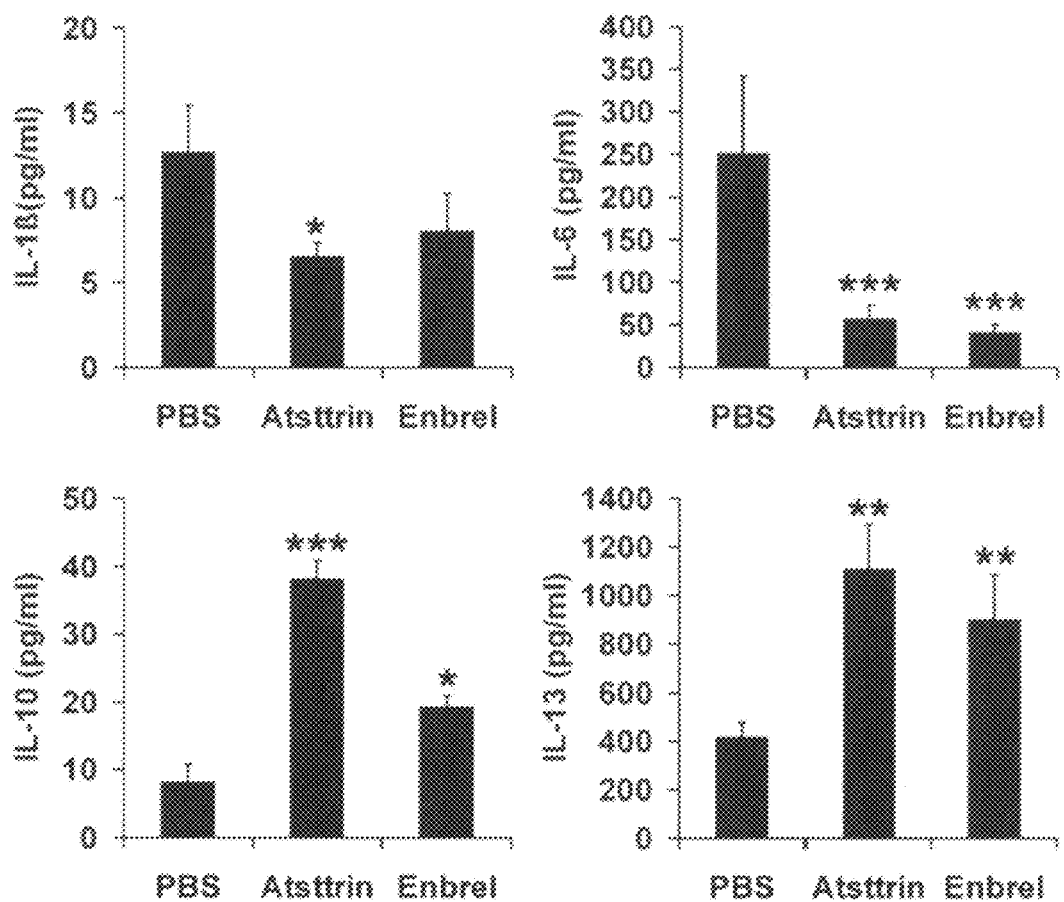
FIG. 34 depicts the effects of Atsttrin compared to controls PBS (negative control) and Enbrel (positive control) on proinflammatory cytokines IL-1β and IL-6 and anti-inflammatory cytokines IL-10 and IL-13. The *, , and * indicate p<0.05, p<0.01 and p<0.001 respectively.
Figure 35:
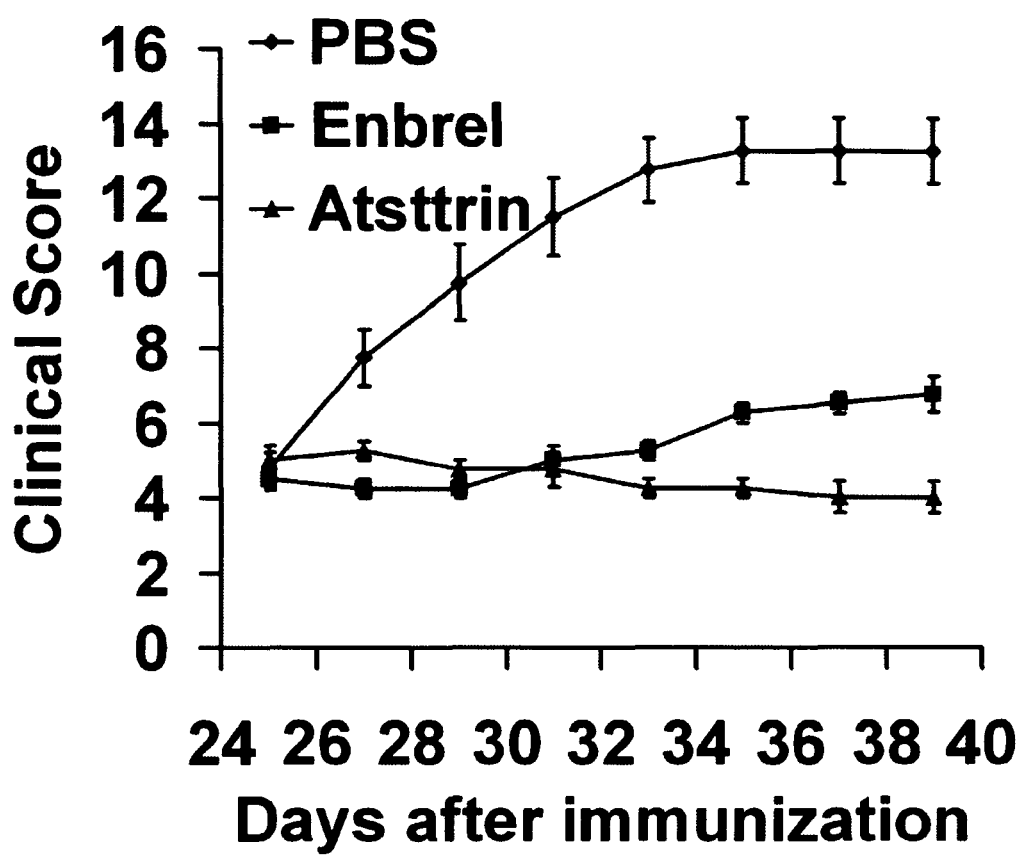
FIG. 35 provides clinical score data in CIA animals treated with either PBS, Enbrel or Atsttrin starting 25 days after collagen immunization to induce arthritis.

The peptides and compositions of the invention include those GEP peptides, including atsttrin, which are based on the human GEP sequence, including as set out in FIGS. 23 and 34, as well as variants thereof having one or more or a few or many substitutions, wherein the binding and activity profiles of the variant(s) are retained when compared to the atsttrin GEP peptide. In as much as GEP peptides from various animals or mammals, including humans, are known, these sequences provide alternative amino acid sequences and variants of potential use in the compositions and methods of the invention, including by substitution of some of the atsttrin human peptide amino acids. Mouse GEP sequence is provided herein in FIG. 25. GEP sequences for various animals are publicly known and disclosed and would be available for evaluation and assessment in the methods and compositions of the invention, and their corresponding and correlating amino acids suitable for evaluation and use as variants of the GEP peptides herein. GEP sequences are available and herein incorporated by reference as follows: rat (Genbank accession AAA16903.1, CAA44198.1), mouse (Genbank accession P28798.2, BAE35389.1, NP_032201.2), Sumatran orangutan (Genbank accession NP_001126689.1), crab-eating macaque (Genbank accession BAE01796.1), horse (Genbank accession XP_001489791.1), cattle (Genbank accession NP_001070482.1), rabbit (Genbank accession XP_002719228.1), pig (Genbank accession NP_001038043.1), chimpanzee (Genbank accession XP_511549.2) and opossum (Genbank accession XP_001374870.1).

A peptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic peptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of TNF/TNFR activity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

A particular biologically compatible composition is an aqueous solution that is buffered using, e.g., Tris, phosphate, or HEPES buffer, containing salt ions. Usually the concentration of salt ions will be similar to physiological levels. Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

A particular embodiment of the present composition invention is a pharmaceutical composition comprising a therapeutically effective amount of GEP, GEP peptide(s) and/or atsttrin as described hereinabove, in admixture with a pharmaceutically acceptable carrier. Another particular embodiment is a pharmaceutical composition for the treatment or prevention of a disease characterized by TNF/TNFR activity including infections, allograft reactions, inflammation, allergic and autoimmune diseases, and cancer, or a susceptibility to said disease, comprising an effective amount of the GEP, GEP peptide(s) and/or atsttrin, its pharmaceutically acceptable salts, hydrates, solvates, or prodrugs thereof in admixture with a pharmaceutically acceptable carrier. A further particular embodiment is a pharmaceutical composition for the treatment or prevention of a disease involving inflammation, or a susceptibility to the condition, comprising an effective amount of the GEP, GEP peptide(s) and/or atsttrin, its pharmaceutically acceptable salts, hydrates, solvates, or prodrugs thereof in admixture with a pharmaceutically acceptable carrier.

The compositions of the invention may include GEP, GEP peptides, atsttrin, and/or derivatives thereof in combination with one or more agents suitable for the alleviation, prevention or treatment of inflammation, immunological conditions, hyperproliferative conditions, and/or cancer. The compositions of the invention may include GEP, GEP peptides, atsttrin, and/or derivatives thereof in combination with one or more of an anti-inflammatory agent, an anti-cancer agent, or an immunodulatory agent. More generally these anti-cancer agents may be tyrosine kinase inhibitors or phosphorylation cascade inhibitors, post-translational modulators, cell growth or division inhibitors (e.g. anti-mitotics), inhibitors or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. In addition, the composition may incorporate or be administered with immune modulators, such as interleukins, tumor necrosis factor (TNF) or other growth factors, colony stimulating factors, cytokines or hormones.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (e.g. monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The agents or compositions of the invention may be combined for administration with or embedded in polymeric carrier(s), biodegradable or biomimetic matrices or in a scaffold.

The carrier, matrix or scaffold may be of any material that will allow composition to be incorporated and expressed and will be compatible with the addition of cells or in the presence of cells. Particularly, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treatment with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluoroethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the particular embodiment, the matrix is biodegradable over a time period of less than a year, more particularly less than six months, most particularly over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J.). In general, these polymers are at least partially soluble in aqueous solutions, such as water, buffered salt solutions, or aqueous alcohol solutions that have charged side groups, or a monovalent ionic salt thereof.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of protein, polynucleotide, peptide, or its antibodies, agonists or antagonists, which ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to target tissues, complexed with cationic lipids, packaged within liposomes, or delivered to target cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery.

Alternatively, or additionally, a polynucleotide encoding the GEP, GEP peptide(s) and/or atsttrin may be particularly included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaiviral vector systems, and all may be used to introduce and express polynucleotide sequence for the expression-inhibiting agents or the polynucleotide expressing the TARGET polypeptide in the target cells.

Particularly, the viral vectors used in the methods of the present invention are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In a preferred embodiment, the viral element is derived from an adenovirus. Preferably, the vehicle includes an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid a preferred vehicle for incorporating in a library of the invention. An adenovirus is capable of infecting a wide variety of cells. However, different adenoviral serotypes have different preferences for cells. To combine and widen the target cell population that an adenoviral capsid of the invention can enter in a preferred embodiment, the vehicle includes adenoviral fiber proteins from at least two adenoviruses. Preferred adenoviral fiber protein sequences are serotype 17, 45 and 51. Techniques or construction and expression of these chimeric vectors are disclosed in US 2003/0180258 and US 2004/0071660, hereby incorporated by reference.

In a preferred embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to target the vehicle to a certain cell or to induce enhanced delivery of the vehicle to the cell. Preferably, the nucleic acid derived from an adenovirus encodes for essentially all adenoviral late proteins, enabling the formation of entire adenoviral capsids or functional parts, analogues, and/or derivatives thereof. Preferably, the nucleic acid derived from an adenovirus includes the nucleic acid encoding adenovirus E2A or a functional part, derivative, and/or analogue thereof. Preferably, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present method of treatment invention.

Certain embodiments of the present invention use retroviral vector systems. Retroviruses are integrating viruses that infect dividing cells, and their construction is known in the art. Retroviral vectors can be constructed from different types of retrovirus, such as, MoMuLV ("murine Moloney leukemia virus") MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda $P_r$, $P_1$, and trp promoters. Among the eukaryotic (including viral) promoters useful for practice of this invention are ubiquitous promoters (e.g. HPRT, vimentin, actin, tubulin), therapeutic gene promoters (e.g. MDR type, CFTR, factor VIII), tissue-specific promoters, including animal transcriptional control regions, which exhibit tissue specificity and have been utilized in transgenic animals, e.g. immunoglobulin gene control region which is active in lymphoid cells (Grosschedl, et al. (1984) Cell 38:647-58; Adames, et al. (1985) Nature 318: 533-8; Alexander, et al. (1987) Mol. Cell. Biol. 7:1436-44), and mouse mammary tumor virus control region which is active in testicular, breast, lymphoid and mast cells (Leder, et al. (1986) Cell 45:485-95).

Other promoters which may be used in the practice of the invention include promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Further promoters which may be of use in the practice of the invention include promoters which are active and/or expressed in dendritic cells.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Feigner, et. al. (1987) Proc. Natl. Acad. Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Feigner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce a DNA vector in vivo as a naked DNA plasmid (see U.S. Pat. Nos. 5,693,622, 5,589,466 and 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson, et al. (1992) J. Biol. Chem. 267:963-7; Wu and Wu, (1988) J. Biol. Chem. 263: 14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

In addition, the present invention envisions preparing GEP peptides and/or atsttrin peptides that have distinct or different structural or sequence properties, and the use of peptidomimetics, and peptidomimetic bonds, such as ester bonds, to prepare additional peptides or agents with the properties of the GEP peptides and/or atsttrin, i.e. capable of inhibiting or antagonizing TNF and TNF/TNFR. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide antagonists with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189-199; Hruby et al., 1990, Biochem J. 268:249-262.

A constrained, cyclic or rigidized peptide may be prepared synthetically, provided that in at least two positions in the sequence of the peptide an amino acid or amino acid analog is inserted that provides a chemical functional group capable of cross-linking to constrain, cyclise or rigidize the peptide after treatment to form the cross-link. Cyclization will be favored when a turn-inducing amino acid is incorporated. Examples of amino acids capable of cross-linking a peptide are cysteine to form disulfide, aspartic acid to form a lactone or a lactase, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson (1980, Biophys. Biochem. Res. Commun. 94:1128-1132). A peptide in which the peptide sequence comprises at least two amino acids capable of cross-linking may be treated, e.g., by oxidation of cysteine residues to form a disulfide or addition of a metal ion to form a chelate, so as to cross-link the peptide and form a constrained, cyclic or rigidized peptide.

The present invention contemplates strategies to systematically prepare cross-links. For example, if four cysteine residues are incorporated in the peptide sequence, different protecting groups may be used (Hiskey, 1981, in The Peptides: Analysis, Synthesis, Biology, Vol. 3, Gross and Meienhofer, eds., Academic Press: New York, pp. 137-167; Ponsanti et al., 1990, Tetrahedron 46:8255-8266). The first pair of cysteine may be deprotected and oxidized, then the second set may be deprotected and oxidized. In this way a defined set of disulfide cross-links may be formed. Alternatively, a pair of cysteine and a pair of collating amino acid analogs may be incorporated so that the cross-links are of a different chemical nature.

The following non-classical amino acids may be incorporated in the peptide in order to introduce particular conformational motifs: 1,2,3,4-tetrahydroisoquinoline-3-carboxylate (Kazmierski et al., 1991, J. Am. Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53-76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2_propenidone-6-carboxylic acid), a β-turn inducing dipeptide analog (Kemp et al., 1985, J. Org. Chem. 50:5834-5838); β-sheet inducing analogs (Kemp et al., 1988, Tetrahedron Lett. 29:5081-5082); β-turn inducing analogs (Kemp et al., 1988, Tetrahedron Lett. 29:5057-5060); ∝_helix inducing analogs (Kemp et al., 1988, Tetrahedron Lett. 29:4935-4938); γ-turn inducing analogs (Kemp et al., 1989, J. Org. Chem. 54:109:115); and analogs provided by the following references: Nagai and Sato, 1985, Tetrahedron Lett. 26:647_650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853-3856); tretrazol (Zabrocki et al., 1988, J. Am. Chem. Soc. 110:5875-5880); DTC (Samanen et al., 1990, Int. J. Protein Pep. Res. 35:501: 509); and analogs taught in Olson et al., 1990, J. Am. Chem. Sci. 112:323-333 and Garvey et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

The present invention further provides for modification or derivatization of the polypeptide or peptide of the invention. These modifications may serve to alter or increase the stability, activity, half-life of the polypeptide or peptide of the invention. Modifications of peptides are well known to one of ordinary skill, and include phosphorylation, carboxymethylation, and acylation. Modifications may be effected by chemical or enzymatic means. In another aspect, glycosylated or fatty acylated peptide derivatives may be prepared. Preparation of glycosylated or fatty acylated peptides is well known in the art. Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure —$(CH_2)_nCH_3$ may be incorporated in the peptide. This and other peptide-fatty acid conjugates suitable for use in the present invention are disclosed in U.K. Patent GB-8809162.4, International Patent Application PCT/AU89/00166, and reference 5, supra. Addition of carbohydrate moieties and the preparation and use of glycosylated analogs of the peptides of the invention is also contemplated, including for improved biological and physical properties such as proteolytic stability and in vivo activity.

Chemical Moieties For Derivatization. Derivatives of the peptides (including variants, analogs and active fragments thereof) of the present invention are further provided. Such derivatives encompass and include derivatives to enhance activity, solubility, effective therapeutic concentration, and transport across the blood brain barrier. Further encompassed derivatives include the attachment of moieties or molecules which are known to interact with TNF/TNFR, to target TNF/TNFR or expressing cells, or to have anti-inflammatory activity. The chemical moieties may be N-terminally or C-terminally attached to the peptides of the present invention. Chemical moieties suitable for derivatization may be, for instance, selected from among water soluble polymers. The polymer selected can be water soluble so that the component to which it is attached does not precipitate in an aqueous environment, such as a physiological environment. Preferably, for therapeutic use of the end-product preparation, the polymer will be pharmaceutically acceptable. The polymer may be branched or unbranched. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols and polyvinyl alcohol. Polyethylene glycol propionaldenhyde may have advantages in manufacturing due to its stability in water.

The polymer may be of any suitable molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached may vary, and one skilled in the art will be able to ascertain the effect on function. One may mono-derivative, or may provide for a di-, tri-, tetra- or some combination of derivatization, with the same or different chemical moieties (e.g., polymers, such as different weights of polyethylene glycols). The proportion of polymer molecules to component or components molecules will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the component or components with consideration of effects on functional or antigenic domains of the protein. There are a number of attachment methods available to those skilled in the art, e.g., EP 0 401 384 herein incorporated by reference (coupling PEG to G-CSF), see also Malik et al., 1992, Exp. Hematol. 20:1028-1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the terminal amino acid residues; those having a free carboxyl group include aspartic acid residues glutamic acid residues and the C-terminal amino acid residue. Sulfhydrl groups may also be used as a reactive group for attaching the polyethylene glycol molecule(s). Preferred for therapeutic purposes is attachment at an amino group, such as attachment at the N-terminus or lysine group.

More particularly the present invention provides derivatives which are fusion proteins comprising the peptides of the present invention or fragments thereof. Thus peptides of the present invention and fragments thereof can be "modified" i.e., placed in a fusion of chimeric peptide or protein, or labeled, e.g., to have an N-terminal FLAG-tag. In a particular embodiment a peptide can be modified by linkage or attachment to a marker protein such as green fluorescent protein as described in U.S. Pat. No. 5,625,048 filed Apr. 29, 1997 and WO 97/26333, published Jul. 24, 1999 (each of which are hereby incorporated by reference herein in their entireties). In one such embodiment, a chimeric peptide can be prepared, e.g., a glutathione-S-transferase (GST) fusion protein, a maltose-binding (MPB) protein fusion protein, or a poly-histidine-tagged fusion protein, for expression in a eukaryotic cell. Expression of the peptide of the present invention as a fusion protein can facilitate stable expression, or allow for purification based on the properties of the fusion partner. For example, GST binds glutathione conjugated to a solid support matrix, MBP binds to a maltose matrix, and poly-histidine chelates to a Ni-chelation support matrix. The fusion protein can be eluted from the specific matrix with appropriate buffers, or by treating with a protease specific for a cleavage site usually engineered between the peptide and the fusion partner (e.g., GST, MBP, or poly-His). Alternatively the chimeric peptide may contain the green fluorescent protein, and be used to determine the intracellular localization of the peptide in the cell.

The invention also includes derivatives wherein at least one of the attached chemical moieties is a molecule having multiple sites for peptide attachment and capable of binding at least two of said peptides simultaneously to generate a multimeric peptide structure. This derivative has the effect of increasing the available local concentration of the carbohydrate epitope mimic peptide(s) of the present invention. Alternatively, or in addition, such moieties can function in providing a stable scaffold to retain the peptide in place for activity, thereby reducing or preventing diffusion or degradation. More particularly, such molecule is selected from the group of BSA, ovalbumin, human serum allbumin, polyacrylamide, beads and synthetic fibers (biodegradable and non-biodegradable).

The carbohydrate epitope mimic peptide of the present invention may be prepared and utilized as monomers, dimers, multimers, heterodimers, heteromultimers, etc. Presentation or administration of the peptide in multimeric form may result in enhanced activity or otherwise increased modulation of the activity mediated by the peptide(s), including TNF antagonistic activity and/or inhibiting TNF/TNFR signaling and activity. The peptide monomer could be produced in a variety of ways. The peptide of the present invention can be synthesized using a protein synthesizer and utilizing methods well known in the art and as described hereinabove, incorporating amino acid modifications, analogs, etc. as hereinabove described. In addition, the DNA sequence of the peptide can be inserted into an expression vector such as pSE (Invitrogen) or pcDNA3 (Invitrogen) for production in bacterial or mammalian cell expression systems. Insect or yeast expression systems could also be used. Purification of the peptide could be facilitated by the addition of a tag sequence such as the 6-Histidine tag which binds to Nickel-NTA resins. These tag sequences are often easily removed by the addition of a protease specific sequence following the tag. Dimers and multimers of the peptide can be produced using a variety of methods in the art. The DNA sequence of a dimer or multimer could also be inserted into an expression system such as bacteria or mammalian cell systems. This could produce molecules such as Met-FLHTRLFV)$_x$ where x=2, 3, 4, ... etc. It may be necessary to include a short flexible spacer (Gly-Gly-Gly-Gly-Ser)$_3$ between the peptide or peptidomimetic to increase its effectiveness. Dimers and multimers can also be generated using crosslinking reagents such as Disuccinimidyl suberate (DSS) or Dithoiobis (succinimidyl propionate) (DSP). These reagents are reactive with amino groups and could crosslink the peptide through free amine groups at the arginine residues and the free amine group at the N-terminus. Dimers and multimers can also be formed using affinity interactions between biotin and avidin, Jun and Fos, and the Fc region of antibodies. The purified peptide can be biotinylated and mixed with factors that are known to form strong protein-protein interactions. The peptide or peptidomimetic could be linked to the regions in Jun and Fos responsible for dimer formation using crosslinkers such as those mentioned above or using molecular techniques to create a peptide-Jun/Fos molecule. When the Jun and Fos peptide hybrids are mixed, dimer formation would result. In addition, production of a peptide-Fc hybrid could also be produced. When expressed in mammalian cells, covalent disulfide bonds form through cysteines in the Fc region and dimer formation would result. Heterodimers and heteromultimers of the peptide could also be produced. This would generate possible multifunctional molecules where parts of the whole molecule are responsible for producing a multitude of effects, such as anti-TNF and/or anti-inflammatory and/or cell growth modulating effects. The same technologies as those listed above could be used to generate these multifunctional molecules. Molecular techniques could be used to insert the carbohydrate epitope mimic peptide into a protein at the DNA level. This insertion could take place at the N- or C-terminus, or in the middle of the protein molecule. Heterodimers could be formed using peptide/Fc or peptide/June or Fos hybrid molecules. When mixed with other Fc or Jun/Fos containing hybrids dimer formation would result producing heterodimers. Crosslinking reagents could also be used to link the peptide to heterodimers. Lastly, biotinylation of the peptide along with biotinylation of other molecules could be used to create multimers. Mixing of these components with avidin could create large multifunctional complexes, where each of the four biotin binding sites of the avidin molecule is occupied by a different biotinylated molecule.

In one aspect the present invention provides a method of preventing and/or treating a disease characterized by, mediated by or facilitated by TNF/TNFR activity and/or signaling and/or a diseases characterized by inflammation, immune injury, and cancer, said method comprising administering to a subject a therapeutically effective amount of a TNF antagonist peptide as disclosed herein. In a particular embodiment, the peptide is selected from GEP, GEP peptide(s) and/or atsttrin. In a particular embodiment, the disease is selected from rheumatoid arthritis, osteoarthritis, ankylosing spondylitis, psoriasis, inflammatory bowel diseases, Chrohn's disease, ulcerative colitis, uveitis, inflammatory lung diseases, and chronic obstructive pulmonary disease. In an embodiment, the disease may be an immunological disorder or condition, including allergies and auto-immune diseases, such as lupus and multiple sclerosis. In an aspect, the disease may be cancer, including a GEP-mediated cancer or TNF/TNFR mediated cancer.

The invention also relates to the use of a peptide as described above and herein for the preparation of a medicament for treating or preventing a disease characterized by, mediated by or facilitated by TNF/TNFR activity and/or signaling and/or diseases characterized by inflammation, and cancer. In a particular embodiment, the disease is characterised by inflammation. In a particular embodiment of the present invention the disease is selected from rheumatoid arthritis, osteoarthritis, ankylosing spondylitis, psoriasis, inflammatory bowel diseases, Chrohn's disease, ulcerative colitis, uveitis, inflammatory lung diseases, and chronic obstructive pulmonary disease.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

GEP Binds to and Antagonizes TNFα Receptors (TNFR)

Modern methods of global analysis of protein-protein interactions followed by biological assessment have led to powerful ways of identifying novel proteins not previously associated with the pathogenesis of a particular disease or organ system. Through a functional genetic screen, we have now discovered that GEP, a novel mediator in chondrogenesis and arthritis, associates with TNFR. This extends our understanding of the action of growth factors and cytokines in cartilage biology and their application to treatment of cartilage disorders and arthritic conditions. In particular, our studies shed light on a naturally occurring antagonist of the central proinflammatory cytokine TNFα, and provide insights into the degradative events that occur in patients with arthritic disorders. The identification and manipulation of growth factors that regulate the chondrogenic potential of mesenchymal stem cells and act as an inhibitors of a central proinflammatory cytokine can be used to optimize the therapeutic application in cartilage disorders and connective tissue disorders. Important long-term goals of this work are (1) define the role of GEP, TNFα, as well as interaction and function interplay among them in regulating skeletal biology and related diseases; and (2) to recruit GEP, specially GEP-derived peptides, to develop new anti-TNF/TNFR therapeutic interventions for various kinds of TNF-related diseases, including arthritis.

Our global screens led to the isolation of several novel GEP-binding partners and among them TNF receptors (TNFR) are of great interest to us. Subsequent studies showed that GEP directly bound to the extracellular domains of TNFR, and GEP-stimulated signaling and target gene expression in chondrocytes strictly depends on TNFR. The fact that both GEP and TNFα bind to TNFR raised the possibility that the binding of GEP to TNFR may block the association of TNFα and its receptors, i.e., GEP may act as a naturally-occurring antagonist of TNFα. Indeed, GEP dramatically inhibits TNFα-induced inflammation response and chondrocyte apoptosis.

TNFR2 Identified as a GEP-Associated Receptor:

Taking into account the biological properties of GEP, it has been hypothesized that GEP could act through "classic" membrane receptor(s), as do other known growth factors. Thus far, a functional receptor has not been identified. In a search for GEP-associated proteins we screened a yeast two-hybrid (Y2H) cDNA library using the construct pDBleu-GEP (a.a.21-588) encoding GEP lacking signal peptide as bait, and isolated 24 positive clones. Sequencing data from these clones showed that two of them were cell surface TNFR2 (TNFRSF1B/CD120b; Accession #NM_130426).

Figure 1:
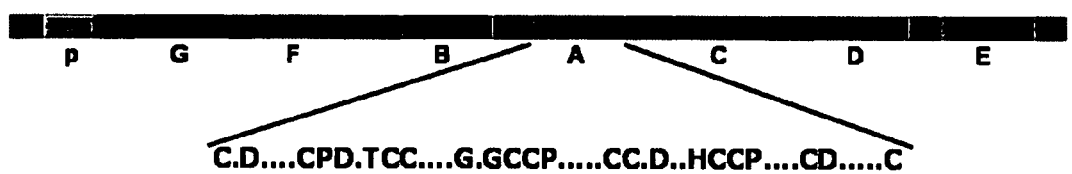
FIG. 1 depicts the structure of GEP growth factor. For the unit consensus sequence C represents cysteine, D aspartic acid, P proline, T threonine, G glycine, H histidine; dots represent any amino acids.
Figure 2:
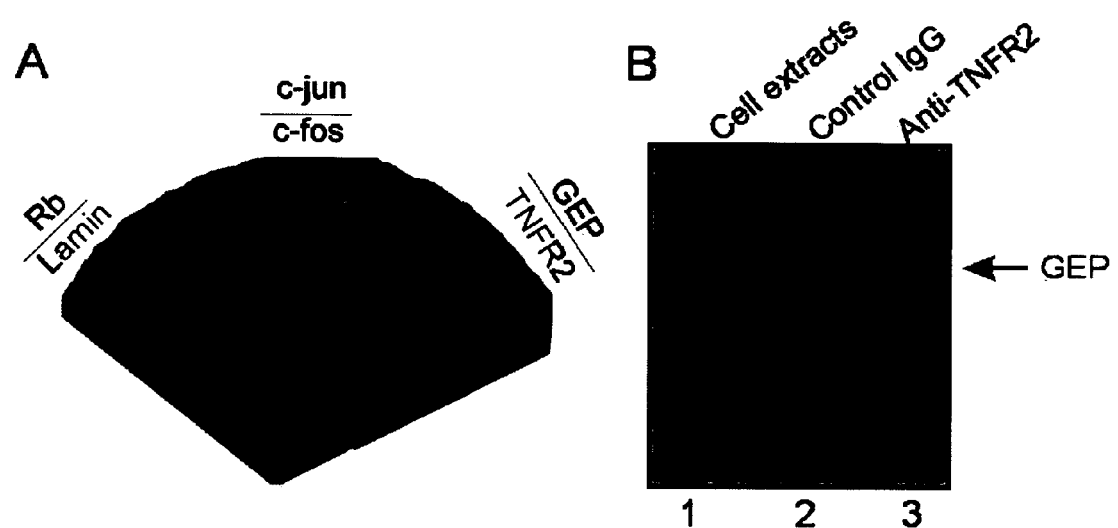
FIG. 2 (A) Binding of GEP to TNFR in Yeast. Each Pair of plasmids, as indicated, was co-transformed into yeast strain MAV203. Yeast transformants were selected on SD-leu⁻/trp⁻/his⁻/ura⁻/3AT⁺ plates and tested for β-galactosidase activity. The known interaction between c-Jun and c-Fos was used as a positive control, whereas the lack of interaction between Rb and lamin was used as a negative control. (B) GEP associates with TNFR2 in chondrocytes. Cell extracts prepared from human chondrocytes were incubated with control IgG, anti-TNFR2 antibodies followed by protein A-agarose. The immunoprecipitated protein complex and cell extracts (lane 1, a positive control) were examined by immunoblotting with anti-GEP antibodies.

GEP Binds to TNFR2 in Yeast and in Chondrocytes:

To verify the interaction between GEP and TNFR2 in yeast the plasmid encoding the GEP linked to Gal4 DBD and the plasmid encoding an N-terminal truncated mutant of TNFR2 (a.a. 26-567) fused to the VP16AD were co-transformed into the yeast cells. Like the c-Jun/c-Fos pair, which is known to interact and used as a positive control, our assays indicated that COMP interacts with GEP in yeast, based on the activity of β-galactosidase (FIG. 2A). To determine whether these two proteins interacted in primary human chondrocytes, a coimmunoprecipitation (Co-IP) assay was performed (FIG. 2B). Briefly, the cell extracts prepared from isolated human chondrocytes were incubated with either anti-TNFR2 antibody or control IgG, and the immunoprecipitated complexes were subjected to a reducing SDS-PAGE and detected with anti-GEP antibodies. A specific GEP band was present in the immunoprecipitated complexes brought down by anti-TNFR2 (lane 3), but not by control IgG (lane 2) antibodies, demonstrating that GEP specifically binds to the TNFR2 in primary human chondrocytes.

Figure 3:
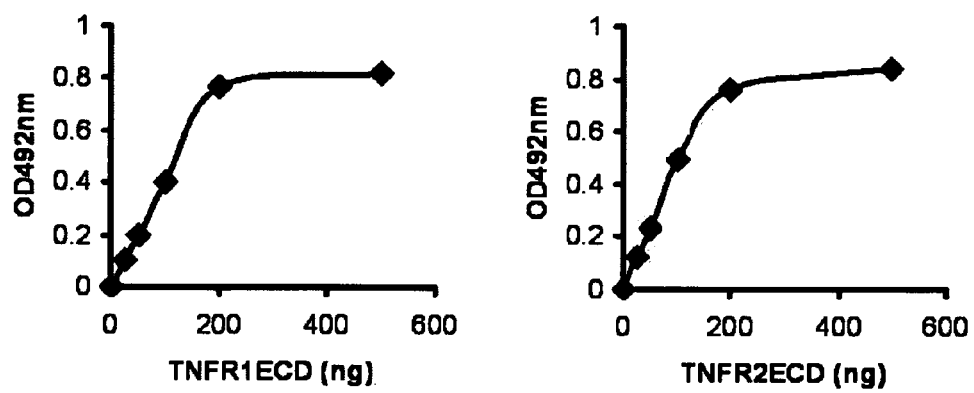
FIG. 3 depicts solid phase binding of TNFR1 extracellular domain (TNFR1ECD) and TNFR2 extracellular domain (TNFR2ECD) to recombinant GEP coated on microtiter plates.

Direct Binding of GEP to the Extracellular Domains of TNFR1 and TNFR2:

Since there is remarkable amino acid similarity between extracellular domains of TNFR1 and TNFR2, we next determined whether GEP directly binds to TNFR1 and TNFR2 using solid-phase binding assay with recombinant GEP and extracellular domains of TNFR1 and TNFR2 (R & D System) (FIG. 3). Briefly, microtiter plates were coated with 500 ng of purified GEP in 100 μl of TBS buffer (50 mM Tris/HCl, 150 mM NaCl, pH7.4). After blocking, various amounts (5-500 ng) of extracellular domain of TNFR1 (TNFR1ECD, left panel) or extracellular domain of TNFR2 (TNFR2ECD, right panel) were added to each well, and bound protein from the liquid phase was detected by antibody against TNFR1 or TNFR2, followed by a secondary antibody conjugated with horseradish peroxidase. As shown in FIG. 3, GEP demonstrated dose-dependent binding and saturation to the liquid-phase TNFR1ECD and TNFR2ECD.

Figure 4:
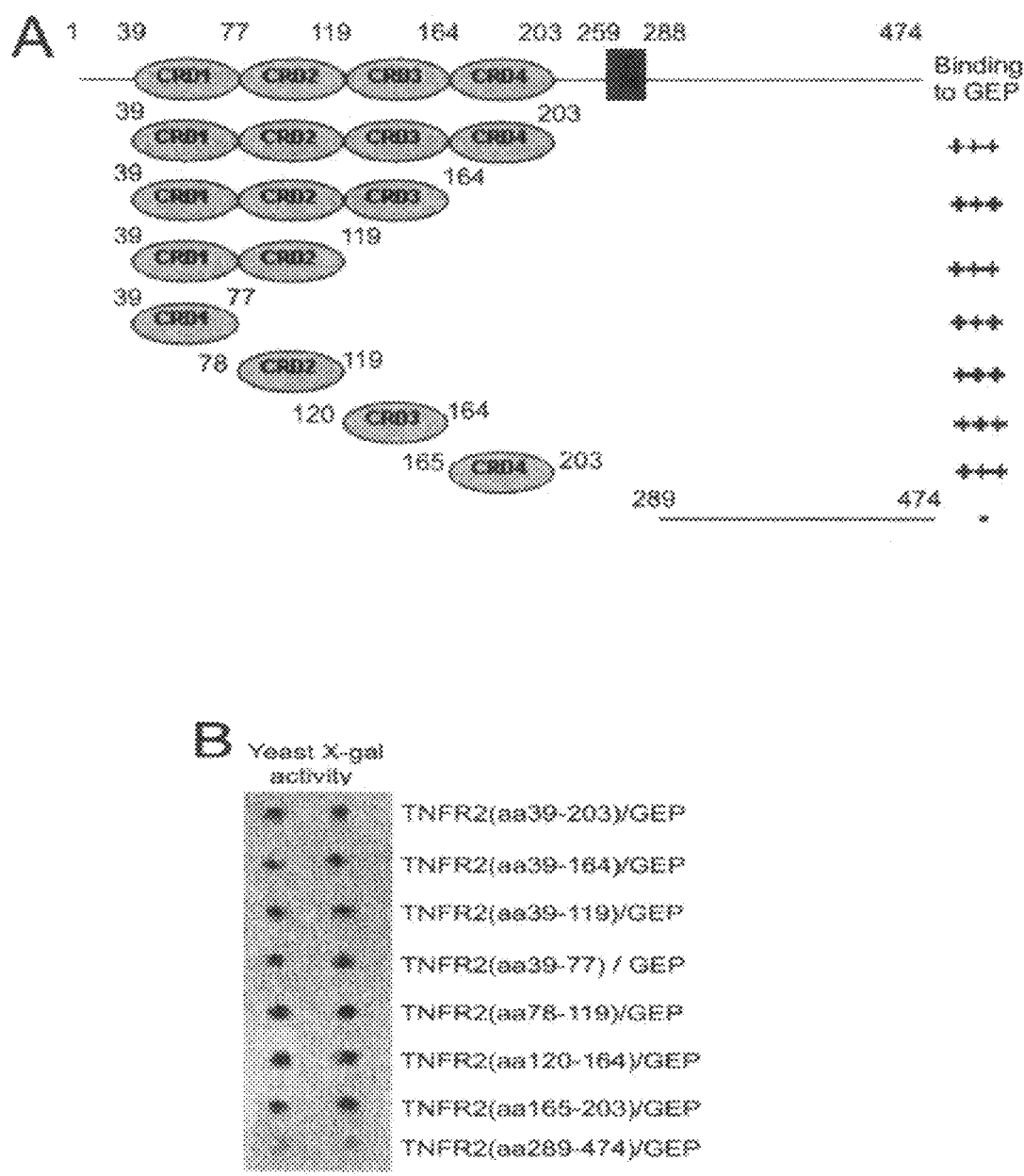
FIG. 4 (A) Schematic diagram of TNFR2 constructs used to map those of its fragments that bind to GEP. (B) β-Galactosidase assays.

Cysteine-Rich Domain (CRD) of TNFR2 is Sufficient for Binding to GEP:

Various deletion mutants of TNFR2 were generated and tested in yeast two-hybrid assay for their ability to interact with GEP. Results from filter-based β-galactosidase assays (FIG. 4) of all these mutants are summarized in FIG. 4A. Our conclusion from this set of experiments is that each CRD (i.e. CRD1, CRD2, CRD3 or CRD4) of TNFR2 is sufficient for its interaction with GEP.

Figure 5:
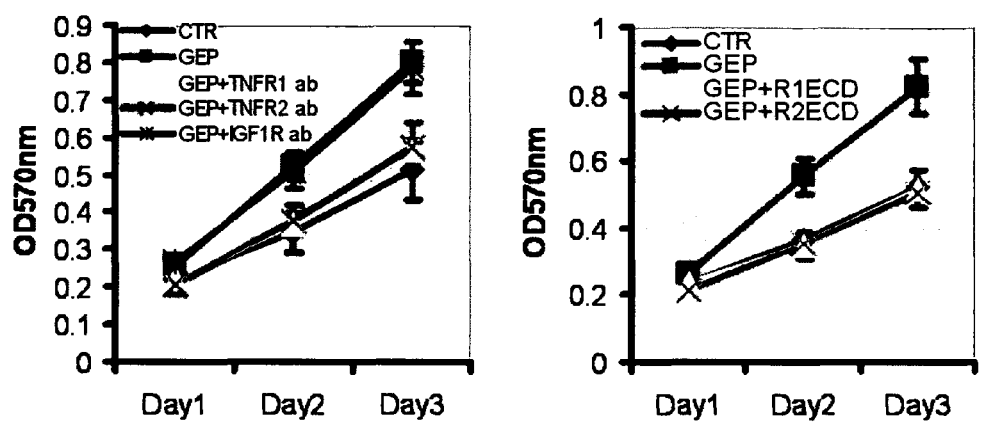
FIG. 5 depicts an MTT assay. Human chondrocytes were cultured in the absence (CTR) or presence of 50 ng/ml GEP (GEP) or GEP plus either 1 ug/ml of anti-TNFR1 (GEP+TNFR1 ab), anti-TNFR2 (GEP+TNFR2 ab) or 1 ug/ml of anti-IGF1R (GEP+TGF1R ab, employed as a control), and cell proliferation was analyzed using an MTT assay.

Anti-TNFR specific blocking antibodies or recombinant extracellular domains of TNFR abolishes GEP-stimulated chondrocyte proliferation: The findings that GEP binds to the TNRF, together with our recent report that GEP has potent mitogenic effects on human chondrocytes [49], led us to determine whether GEP-stimulated chondrocyte proliferation depends on the TNFR. Human chondrocytes were cultured in the absence (CTR) or presence of 50 ng/ml GEP (GEP) or GEP plus either 1 ug/ml of anti-TNFR1 (GEP+TNFR1 ab; SC-7895 is against extracellular domain of TNFR1), anti-TNFR2 (GEP+TNFR2 ab; SC-12751 is against extracellular domain of TNFR2) or 1 ug/ml of anti-IGF1R (GEP+TGF1R ab, employed as a control), and cell proliferation was analyzed using an MTT assay (FIG. 5 left panel). As expected, GEP potently stimulated chondrocyte proliferation, and this GEP-stimulated cell proliferation was largely blocked by either anti-TNFR1 or anti-TNFR2 antibody whereas anti-IGF1R did not demonstrate any blocking effects on GEP action.

Since GEP directly associates with the extracellular domains of TNFR, we next examined whether recombinant extracellular domains of TNFR will affect GEP action in chondrocyte proliferation via competing with endogenous TNFR for interacting with GEP. As shown in the right panel of FIG. 5, chondrocyte proliferation induced by 50 ng/ml GEP was completely abolished by recombinant extracellular domain of either TNFR1 (R1ECD, 25 ng/ml) or TNFR2 (R2ECD, 25 ng/ml). Taken together, these results indicate that GEP-mediated chondrocyte proliferation strictly depends on the TNFR activity.

Figure 6:
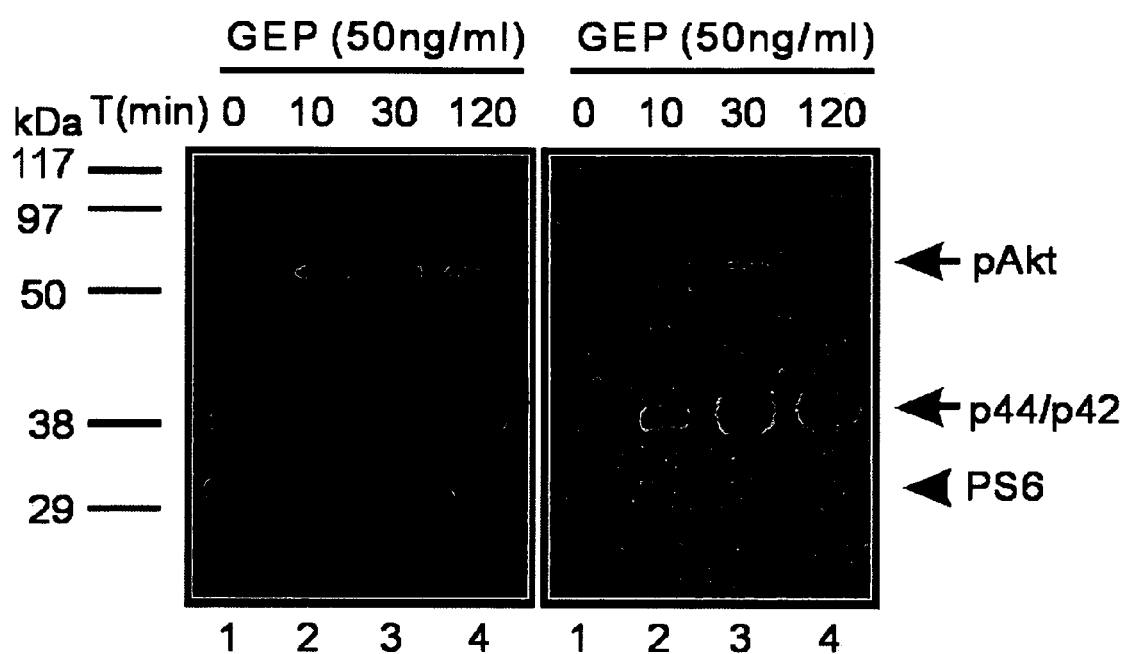
FIG. 6. GEP activates Akt and Erk1/2 pathways in human C28I2 chondrocytes. Note both long-time (5 min, left panel) and short-time (30 sec. right panel) exposures of the film are presented.

GEP Activates Akt and Erk1/2 Pathways in Chondrocytes:

We next sought to analyze GEP-activated signaling in chondrocytes using The PathScan® Multiplex Western Cocktail I (Cell Signaling) that allows us to simultaneously detect levels of phospho-p90RSK, phospho-Akt, phosphop44/42 MAPK (Erk1/2) and phospho-S6 ribosomal protein on a single membrane. Human C28I2 chondrocytes (provided by Dr. Mary B. Goldring) were starved for 24 hours and treated with 50 ng/ml of GEP for various time points and cell lysates were analyzed using The PathScan® Multiplex Western Cocktail I. As shown in FIG. 6, GEP specifically activated Akt and p44/p42 (Erk1/2) pathways in chondrocytes.

Figure 7:
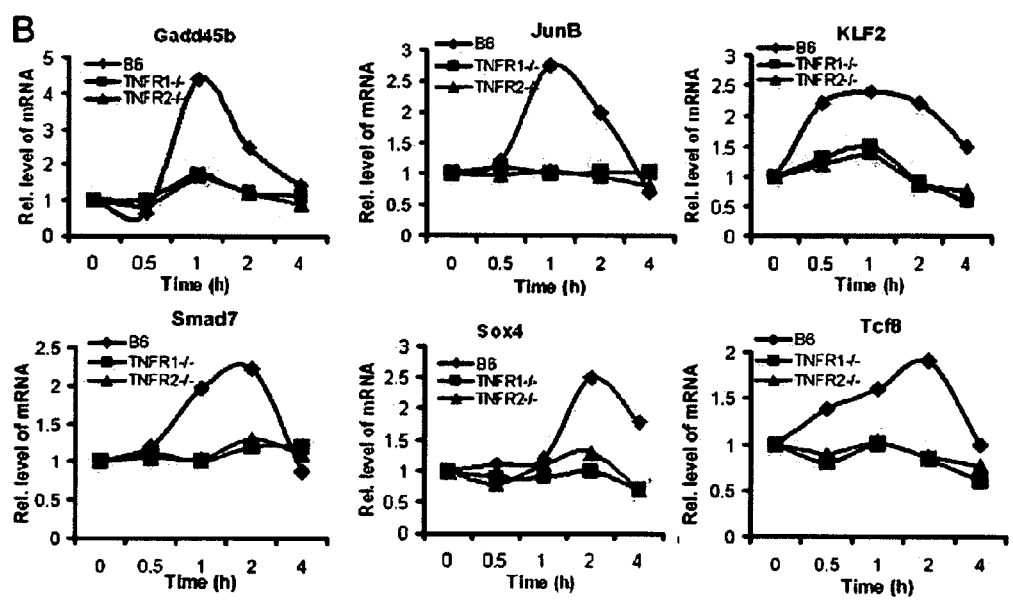
FIG. 7 depicts expression profiling of the genes Gadd45b, JunB, KLF2, Smad7, Sox4 and Tcf8 using real-time PCR with primary wild type (B6), TNFR1−/−, and TNFR2−/− MLE cells cultured in the presence of 50 ng/ml GEP for various time points.

GEP-Mediated Activation of Target Genes Depends on TNFR:

To identify GEP downstream molecules, we performed genome-wide DNA chip analysis. Total RNA was isolated from human C28I2 chondrocytes treated with 50 ng/ml of GEP for various time points and analyzed by microarray analysis (Affymetrix, Santa Clara, Calif.). Approximately 40 genes were determined to be upregulated (over 2-fold) following GEP treatment as determined by hierarchical clustering [53]. Interestingly, the GEP-inducible genes, including Gadd45β, JunB, KLF2, Samd7, Sox4 and Tcf8, are also known to be activated by the TGFβ subfamily [54-56]. We next determined whether activation of these genes by GEP depends on TNFR, expression profiling of these genes were examined using real-time PCR with primary wildtype (B6), TNFR1−/−, and TNFR2−/− MLE cells cultured in presence of 50 ng/ml GEP for various time points (FIG. 7). GEP clearly activated these genes in wildtype MLE cells; however, GEP largely lost these inductions in either TNFR1−/− or TNFR2−/− cells, indicating that GEP induction of its target genes depends on TNFR1 and TNFR2. Interestingly, both TNFR1 and TNFR2 appear to be important for GEP-stimulated gene expression.

Figure 8:
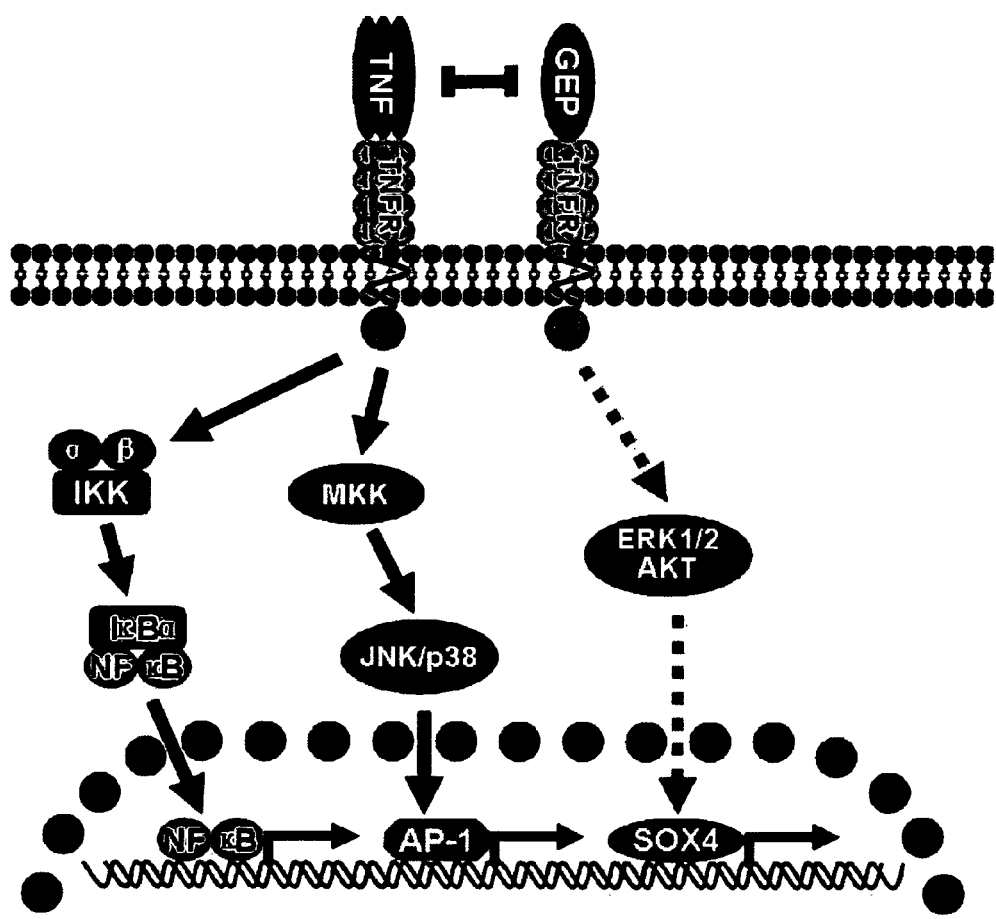
FIG. 8 depicts a model for illustrating intracellular events, including signaling and target gene expression.

A proposed model for illustrating the TNFa- and GEP-induced Intracellular events: GEP binds to the CRD of TNFR (FIG. 4), as does TNFα [57]. Thus there exists a reciprocal inhibition of binding to TNFR between GEP and TNFα. An intriguing question is why GEP and TNFα, that use the same receptor TNFR, induce opposite responses. As illustrated in FIG. 8, TNF α trimmer binds to the extracellular domains of TNF receptors and induces 1) a strong activation of the stress-related JNK and moderate response of the p38, and 2) activation of NF-kB pathway [58], whereas GEP potently activates Erk1/2 and moderately Akt signaling (FIG. 6 and FIG. 8). A number of GEP-activated genes, including Sox4, Smad7, JunB, Gadd45β, Tcf8, are also activated by the TGFβ subfamily, and GEP-mediated gene activation depends on TNFR (FIG. 7).

EXAMPLE 2

Discovery of Atsttrin (Antagonist of TNF/TNFR Signaling via Targeting TNF Receptors)

Figure 9:
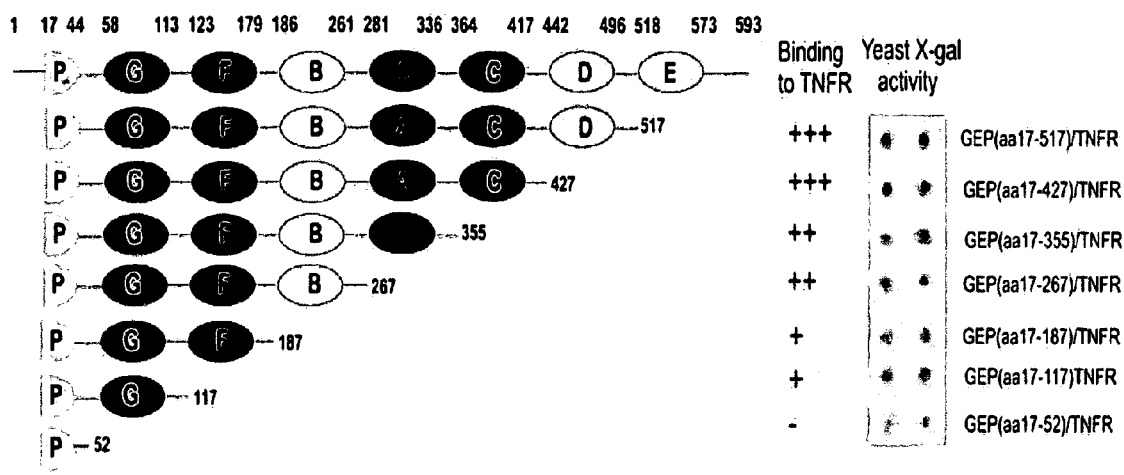
FIG. 9 (Left) Schematic diagram of GEP constructs used to map those of its fragments that bind to TNFR. (Right) β-Galactosidase assays.
Figure 10:
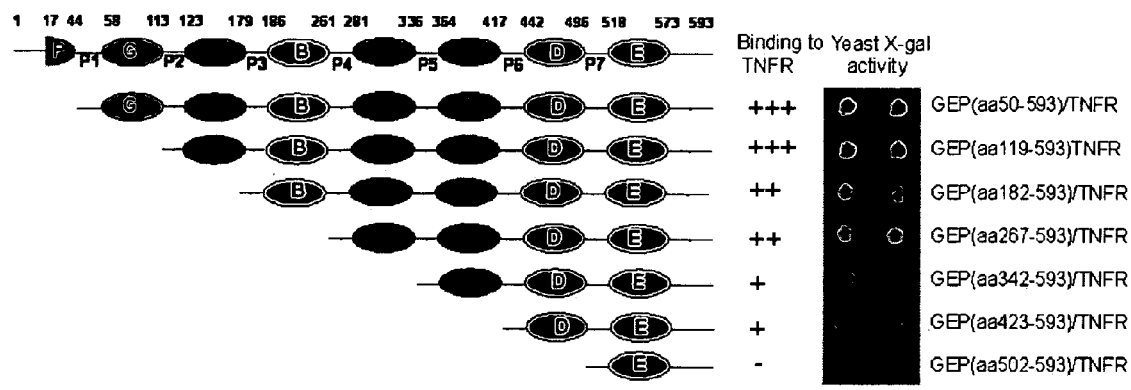
FIG. 10 (Left) Schematic diagram of GEP constructs. (Right) β-Galactosidase assays.

To identify the peptide(s) of GEP required for binding to TNF receptors, a series of GEP mutants (i.e. C-terminal deletions, N-terminal deletions, individual granulin unit, individual linker, as well as various combinations) were expressed in a yeast expression plasmid. Briefly, cDNA segments encoding the series of GEP mutants were amplified by PCR and cloned in-frame into the SalI/NotI sites of pDBleu (Life Technologies) yeast expression vector. The generated plasmids and pPC86-TNFR encoding extracellular domain of TNFR1/R2 was cotransformed into the yeast MaV203 strain containing three reporter genes, His$^+$, Ura$^+$, and LacZ (Life Technologies), and transformants was examined for β-galactosidase. Results from filter-based β-galactosidase assays (right panel in figures FIG. 9 through FIG. 15) of all these mutants are summarized in the left panel of these figures. As revealed in FIG. 9, results from a series of C-terminal deletions indicated that deletions from the C-terminal of GEP reduced the binding affinity to TNFR and finally totally lost binding activity. This is also true for series of N-terminal deletion mutants (FIG. 10).

Figure 11:
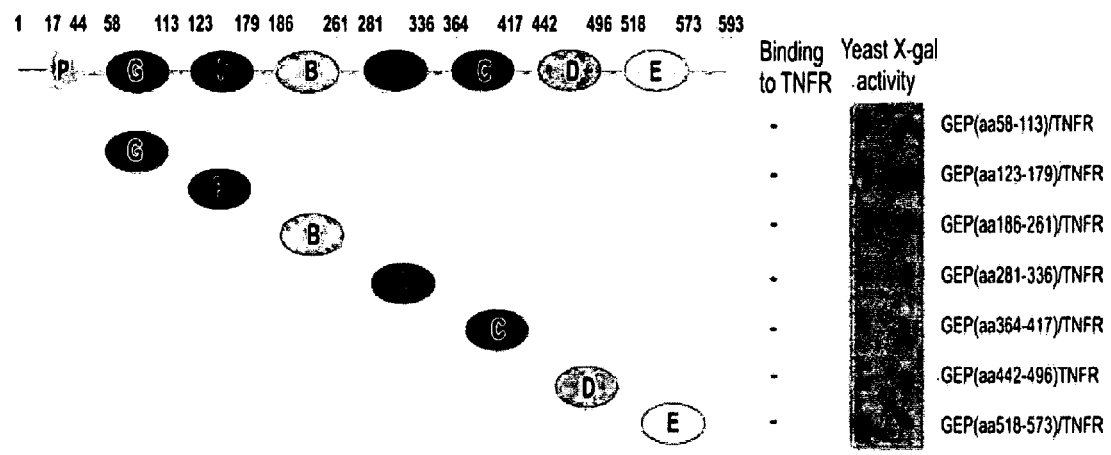
FIG. 11 (Left) Schematic diagram of GEP constructs. (Right) β-Galactosidase assays.
Figure 12:
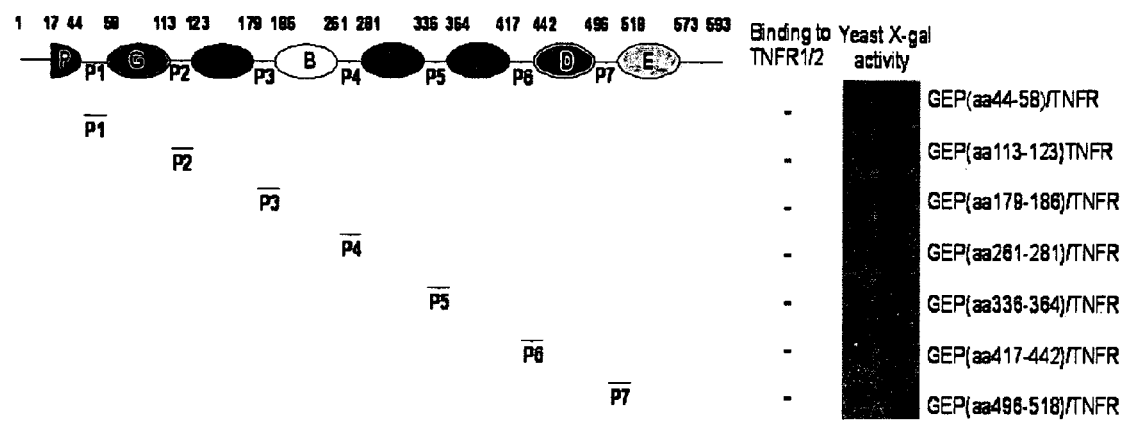
FIG. 12 (Left) Schematic diagram of GEP constructs used to map those of its fragments that bind to TNFR. (Right) β-Galactosidase assays.
Figure 13:
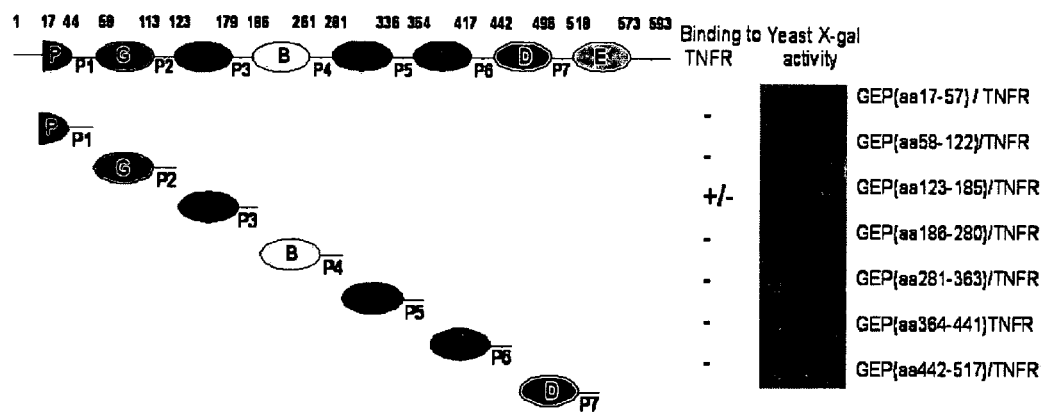
FIG. 13 (Left) Schematic diagram of GEP constructs used to map those of its fragments that bind to TNFR. (Right) β-Galactosidase assays.
Figure 14:
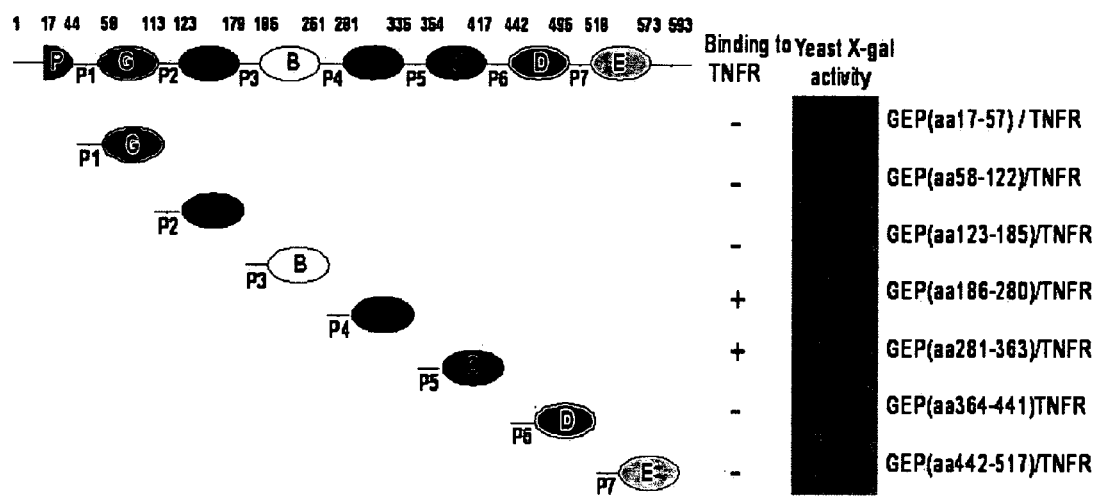
FIG. 14 (Left) Schematic diagram of GEP constructs used to map those of its fragments that bind to TNFR. (Right) β-Galactosidase assays.

Neither a single granulin unit (A, B, C, D, E, F, or G; FIG. 11) nor a single linker unit (P1, P2, P3, P4, P5, P6 or P7; FIG. 12) could bind to TNFR, suggesting that the binding region of GEP may span one or more granulin unit and linker. To examine this hypothesis, we first linked each granulin unit with its 3'-linker and found that granulin unit F plus linker P3 exhibited weak binding to TNFR (FIG. 13). Next, we linked each granulin unit with its 5'-linker and found that P4 plus granulin unit A showed weak binding to TNFR, and also that P5 plus unit C showed weak binding to TNFR (FIG. 14). These findings led us to test the binding of various combinations of half unit of A, C and F plus P3, P4 and P5 to TNFR. As revealed in FIG. 15, ½A+P3+P4+½C+P5+½F demonstrated strong binding to TNFR. This GEP derived peptide is now referred to as Atsttrin.

EXAMPLE 3

GEP Antagonizes TNF α Action

Figure 16:
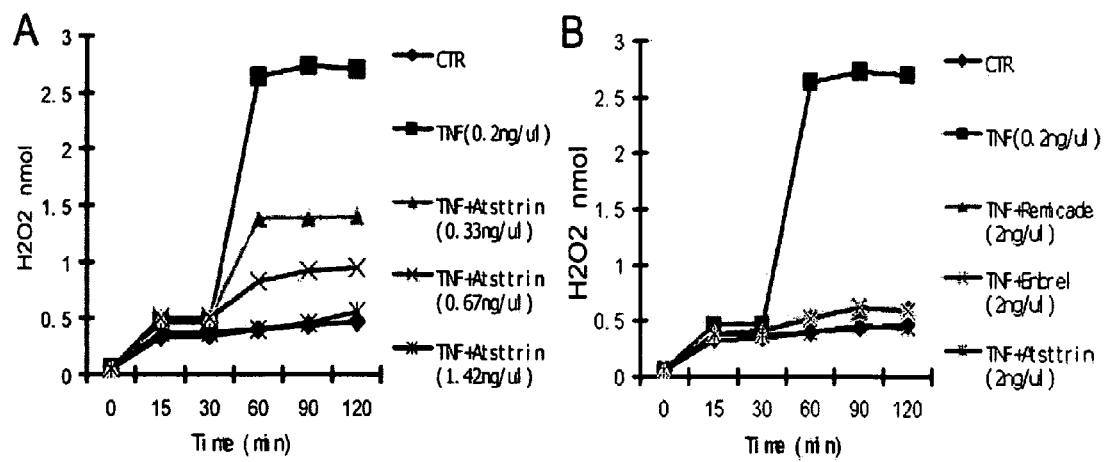
FIG. 16 (A) Atsttrin inhibits the respiratory burst triggered by TNF in a does-dependent manner; (B) Effect of Atsttrin, Remicade and Enbrel on TNF-triggered respiratory burst. Results are means for nmol H2O2 produced by 1.5×104 cells/well in triplicate cultures.

Atsttrin antagonizes TNFα-induced inflammation response: We next determined whether Atsttrin inhibits TNF-mediated inflammation. Neutrophils are triggered by inflammatory stimuli like TNF α to generate large quantities of reactive oxygen species that contribute to neutrophil activation and the development of inflammatory processes [59]. Accordingly, we tested the effect of Atsttrin on TNFα-induced neutrophil activation. As shown in FIG. 16A, Atsttrin dose-dependently inhibits neutrophil activation triggered by TNFα. Importantly and remarkably, Atsttrin exhibits inhibition that rivals (is at least as good as) Enbrel and Remicade (FIG. 16B), which have been used clinically for treating various kinds of inflammatory diseases, including particularly rheumatoid arthritis [60].

Figure 17:
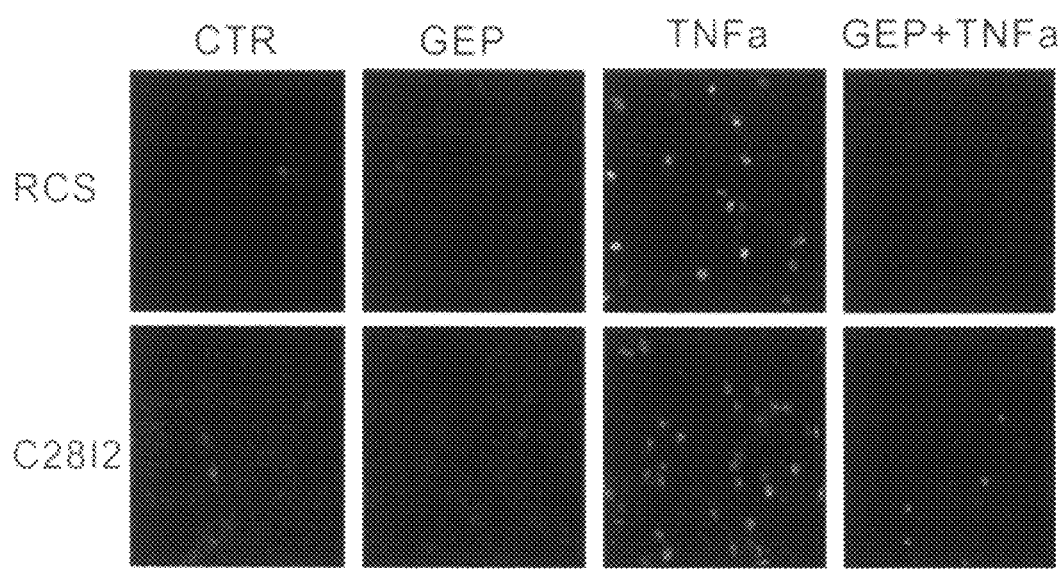
FIG. 17 depicts a TUNEL staining assay. Rat chondrosarcoma (RCS) cells and human C28I2 chondrocytes were serum-starved for 24 h to remove the effect of exogenous growth factors and cytokines. Thereafter, cells were stimulated with 0.02% BSA (CTR), 50 ng/ml of GEP (GEP), 10 ng/ml of TNF-α, or GEP plus TNF-α for 36 h. Apoptosis was measured by using an TUNEL assay kit.

GEP inhibits TNFα-induced cell death: TNF-α has been shown to induce apoptosis in chondrocyte cultures [61-63]. We next determined whether GEP affected TNF-α-induced apoptosis in chondrocytes. Briefly, rat chondrosarcoma (RCS) cells and human C28I2 chondrocytes were serum-starved for 24 h to remove the effect of exogenous growth factors and cytokines. Thereafter, cells were stimulated with 0.02% BSA (CTR, control), 100 ng/ml of GEP (GEP), 100 ng/ml of TNF-α, or GEP plus TNF-α for 36 h. Apoptosis was measured by using an TUNEL assay kit (Promega). As shown in FIG. 17, TNF-α induced prominent cell death in both RCS and C28I2 chondrocytes, whereas GEP dramatically inhibited TNF-α induction of apoptosis in chondrocytes.

Figure 18:
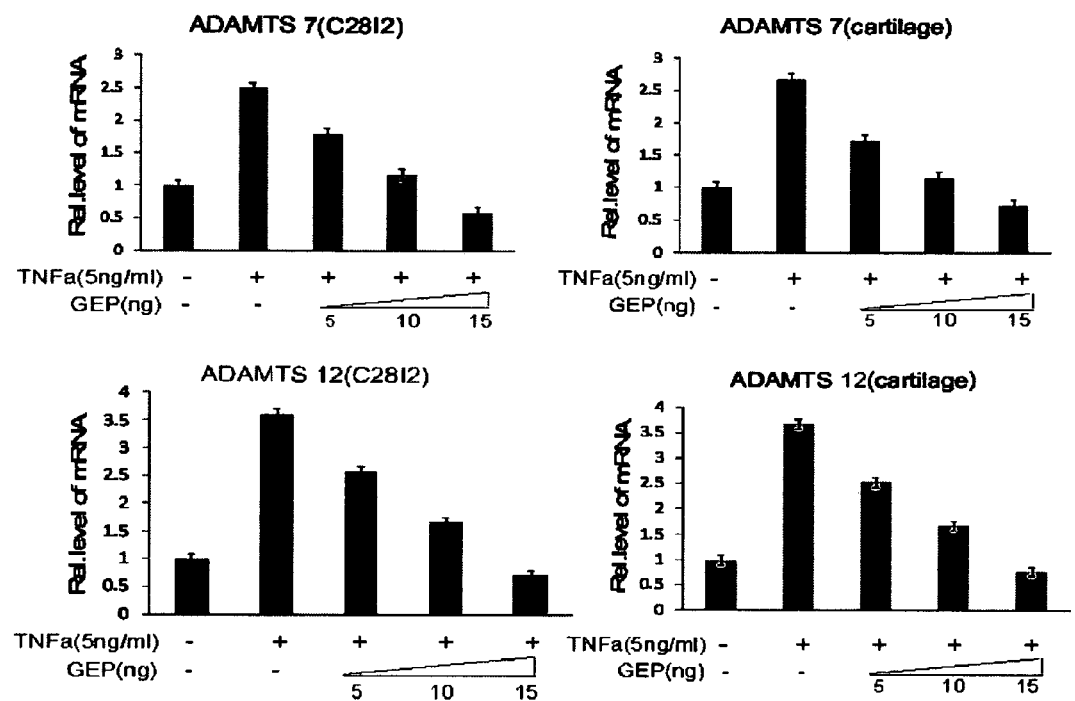
FIG. 18 shows that GEP inhibits TNFα-induced metalloproteinase. Human cartilage explants were cultured in the absence or presence of either 5 ng/ml of TNFα supplemented with various amount of GEP, as indicated, for 1 day in serum-free medium and real-time PCR was performed. The units are arbitrary and the leftmost bar in each group indicates a relative level of 1.

GEP inhibits TNFα-induced metalloproteinase: We have recently reported that TNFα induces expression of ADAMTS-7 and ADAMTS-12, two metalloproteinases in the ADAMTS family [64]. We next determined whether GEP inhibited induction of ADAMTS by TNFα. Briefly, human C28I2 chondrocytes or cartilage explants were treated with TNF α in the absence or presence of various amount of GEP for 48 hours, and the expression of ADAMTS-7 and ADAMTS-12 were determined using real-time PCR with their specific primers. In accordance with our previously report results [64], TNF α clearly induced ADAMTS-7 and ADAMTS-12 expression (FIG. 18). GEP demonstrated a dose-dependent inhibition of TNFα-mediated induction of metalloproteinase in chondrocytes or cartilage explants (FIG. 18).

Figure 19:
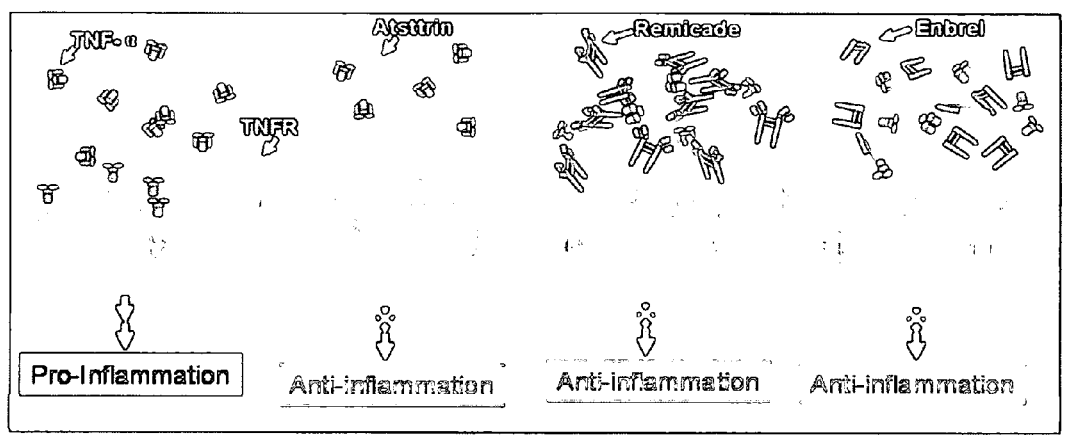
FIG. 19 A proposed model for explaining the anti-inflammation mechanisms of Atsttrin, Enbrel and Remicade. Atsttrin blocks TNF/TNFR signaling via directly binding to TNF receptors, whereas Enbrel and Remicade disturb signaling via targeting to TNF ligand.

Brief Summary of Major Characteristics of GEP and Atsttrin: Compared to the currently available anti-inflammation engineered antibodies or recombinant protein blockers, including etanercept (Enbrel, a soluble TNFR2-IgG1 fusion protein), infliximab (Remicade, a chimeric monoclonal antibody against TNF-α), and adalimumab (a humaneric monoclonal antibody against TNF-α), GEP and its derived Atsttrin have the features as below:

i) Unique anti-TNF/TNFR property: Antibodies and immunoadhesins that directly target cytokines for their systemic removal (ligand ablation) have become an effective therapeutic strategy (e.g. etanercept, adalimumab and infliximab), and in some indications the selective targeting of cytokine receptors (e.g. anakinra) can deliver a more highly effective clinical outcome. Our studies demonstrates that GEP is the first known growth factor that directly targets to TNF receptors (TNFR), thus GEP and its derived peptide(s) represent the first anti-TNF/TNFR signaling blockers through acting on the cytokine receptors, resembling the action of Anakinra that targets to IL-1 receptor. (See FIG. 19 for a comparison of the distinct anti-inflammation mechanisms between GEP/Atsttrin and Enbrel/Remicade). Due to its unique anti-TNF/TNFR signaling activity, Atsttrin may also work well for the patient population who does not respond to current TNFα blockers, such as Remicade.

ii) Low toxicity: Since Atsttrin is derived a naturally-occurring GEP factor that is already present in body fluids, it is expected that GEP and Atsttrin will not cause immunologic issues or responses and will exhibit no or less toxicity when compared to other engineered recombinant proteins.

iii) Multiple Functions: In addition to its anti-inflammatory activity, GEP also has potent tissue-repair function, thus GEP and Atsttrin are expected to block inflammation reaction on one hand, and also repair the injured tissues by inflammation response. In contrast, all current anti-TNF blockers, including Enbrel and Remicade, do not have tissue-repair activity. Furthermore, our pilot studies indicated that Atsttrin has tumor-suppression activity, which represents another application of Atsttrin.

EXAMPLE 4

Atsttrin Inhibits GEP-Stimulated Cancer Cell Proliferation

Figure 20:
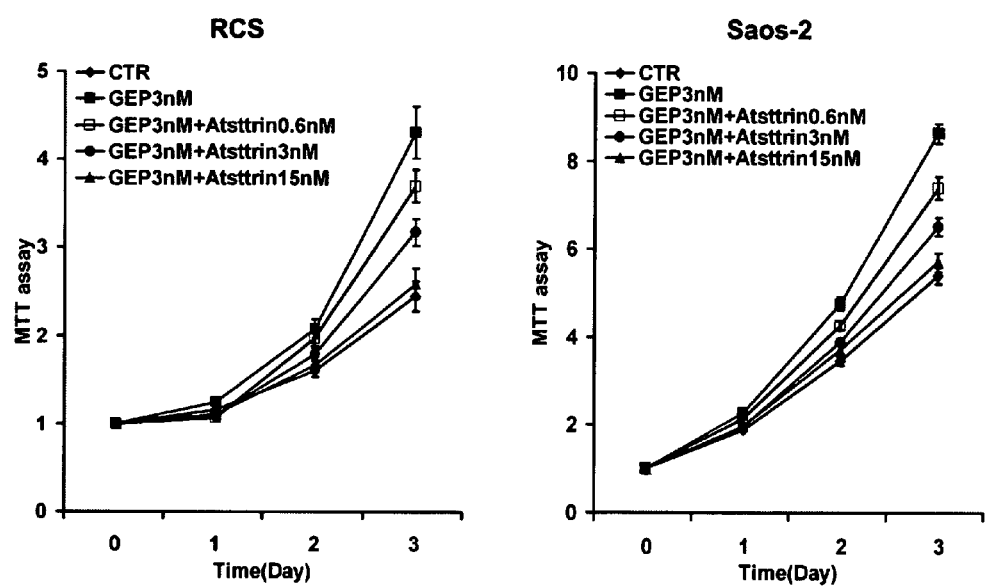
FIG. 20 shows that Atsttrin neutralizes GEP-stimulated cell growth of cancer cells (MTT assay). RCS chondrosarcoma (left panel) and Saos-2 osteosarcoma (right panel) were cultured in the absence (CTR) or presence of GEP (200 ng/1) with or without various amounts of Atsttrin, as indicated, and cell proliferation was analyzed using an MTT assay.

High levels of GEP expression are found in several human cancers and contribute to tumorigenesis in diverse cancers, including breast cancer, clear cell renal carcinoma, invasive ovarian carcinoma, glioblastoma, adipocytic teratoma, and multiple myeloma [16, 18-24]. Atsttrin inhibits TNF-mediated inflammation via blocking the binding of TNF to TNFR, and it is expected that Atsttrin may also inhibit tumor cell growth via blocking the binding of GEP to TNFR. To test this hypothesis we examined the effects of Atsttrin on GEP-stimulated cell proliferation of cancer cells. As revealed in FIG. 20, Atsttrin dose-dependently inhibited GEP-stimulated cell proliferation of cancer cells tested.

References
1. Martel-Pelletier, J., *Pathophysiology of osteoarthritis.* Osteoarthritis Cartilage, 1999. 7(4): p. 371-3.
2. Petersson, I. F., et al., *Changes in cartilage and bone metabolism identified by serum markers in early osteoarthritis of the knee joint.* Br J Rheumatol, 1998. 37(1): p. 46-50.
3. Ayral, X., *Diagnostic and quantitative arthroscopy:* quantitative arthroscopy. Baillieres Clin Rheumatol, 1996. 10(3): p. 477-94.
4. Ayral, X., et al., *Effects of video information on preoperative anxiety level and tolerability of joint lavage in knee osteoarthritis.* Arthritis Rheum, 2002. 47(4): p. 380-2.
5. Aigner, T., et al., *Reexpression of type IIA procollagen by adult articular chondrocytes in osteoarthritic cartilage.* Arthritis Rheum, 1999. 42(7): p. 1443-50.
6. Lippiello, L., D. Hall, and H. J. Mankin, *Collagen synthesis in normal and osteoarthritic human cartilage.* J Clin Invest, 1977. 59(4): p. 593-600.
7. Sandell, L. J. and T. Aigner, *Articular cartilage and changes in arthritis. An introduction: cell biology of osteoarthritis.* Arthritis Res, 2001. 3(2): p. 107-13.
8. Wright, W. E., D. A. Sassoon, and V. K. Lin, *Myogenin, a factor regulating myogenesis, has a domain homologous to MyoD.* Cell, 1989. 56(4): p. 607-17.
9. Zhou, J., et al., *Purification of an autocrine growth factor homologous with mouse epithelin precursor from a highly tumorigenic cell line.* J Biol Chem, 1993. 268(15): p. 10863-9.
10. Anakwe, O. O. and G. L. Gerton, *Acrosome biogenesis begins during meiosis: evidence from the synthesis and distribution of an acrosomal glycoprotein, acrogranin, during guinea pig spermatogenesis.* Biol Reprod, 1990. 42(2): p. 317-28.
11. Baba, T., et al., *Acrogranin, an acrosomal cysteine-rich glycoprotein, is the precursor of the growth modulating peptides, granulins, and epithelins, and is expressed in somatic as well as male germ cells.* Mol Reprod Dev, 1993. 34(3): p. 233-43.
12. Daniel, R., et al., *Cellular localization of gene expression for progranulin.* J Histochem Cytochem, 2000. 48(7): p. 999-1009.
13. Zanocco-Marani, T., et al., *Biological activities and signaling pathways of the granulin/epithelin precursor.* Cancer Res, 1999. 59(20): p. 5331-40.
14. Ong, C. H. and A. Bateman, *Progranulin (granulin-epithelin precursor, PC-cell derived growth factor, acrogranin) in proliferation and tumorigenesis.* Histol Histopathol, 2003. 18(4): p. 1275-88.
15. Hrabal, R., et al., *The hairpin stack fold, a novel protein architecture for a new family of protein growth factors.* Nat Struct Biol, 1996. 3(9): p. 747-52.
16. Davidson, B., et al., *Granulin-epithelin precursor is a novel prognostic marker in epithelial ovarian carcinoma.* Cancer, 2004. 100(10): p. 2139-47.
17. Lu, R. and G. Serrero, *Inhibition of PC cell-derived growth factor (PCDGF, epithelin/granulin precursor) expression by antisense PCDGF cDNA transfection inhibits tumorigenicity of the human breast carcinoma cell line MDA-MB-468.* Proc Natl Acad Sci USA, 2000. 97(8): p. 3993-8.
18. Bateman, A., et al., *Granulins, a novel class of peptide from leukocytes.* Biochem Biophys Res Commun, 1990. 173(3): p. 1161-8.
19. Gonzalez, E. M., et al., *A novel interaction between perlecan protein core and progranulin: potential effects on tumor growth.* J Biol Chem, 2003. 278(40): p. 38113-6.
20. He, Z. and A. Bateman, *Progranulin (granulin-epithelin precursor, PC-cell-derived growth factor, acrogranin) mediates tissue repair and tumorigenesis.* J Mol Med, 2003. 81(10): p. 600-12.
21. He, Z., et al., *Progranulin is a mediator of the wound response.* Nat Med, 2003. 9(2): p. 225-9.
22. Jones, M. B., M. Spooner, and E. C. Kohn, *The granulin-epithelin precursor: a putative new growth factor for ovarian cancer.* Gynecol Oncol, 2003. 88(1 Pt 2): p. S136-9.
23. Wang, W., et al., *PC cell-derived growth factor (granulin precursor) expression and action in human multiple myeloma.* Clin Cancer Res, 2003. 9(6): p. 2221-8.
24. Zhang, H. and G. Serrero, *Inhibition of tumorigenicity of the teratoma PC cell line by transfection with antisense cDNA for PC cell-derived growth factor (PCDGF, epithelin/granulin precursor).* Proc Natl Acad Sci USA, 1998. 95(24): p. 14202-7.
25. Hogue, M., et al., *Granulin and granulin repeats interact with the Tat.P-TEFb complex and inhibit Tat transactivation.* J Biol Chem, 2005. 280(14): p. 13648-57.
26. Hogue, M., et al., *The growth factor granulin interacts with cyclin T1 and modulates P-TEFb-dependent transcription.* Mol Cell Biol, 2003. 23(5): p. 1688-702.
27. Thornburg, N. J., S. Kusano, and N. Raab-Traub, *Identification of Epstein-Barr virus RK-BARF0-interacting proteins and characterization of expression pattern.* J Virol, 2004. 78(23): p. 12848-56.
28. Sell, C., et al., *Effect of a null mutation of the insulin-like growth factor I receptor gene on growth and transformation of mouse embryo fibroblasts.* Mol Cell Biol, 1994. 14(6): p. 3604-12.
29. Xu, S. Q., et al., *The granulin/epithelin precursor abrogates the requirement for the insulin-like growth factor 1 receptor for growth in vitro.* J Biol Chem, 1998.273(32): p. 20078-83.
30. Sun, X., M. Gulyas, and A. Hjerpe, *Mesothelial differentiation as reflected by differential gene expression.* Am J Respir Cell Mol Biol, 2004. 30(4): p. 510-8.
31. Suzuki, M. and M. Nishiahara, *Granulin precursor gene: a sex steroid-inducible gene involved in sexual differentiation of the rat brain.* Mol Genet Metab, 2002. 75(1): p. 31-7.

32. Barreda, D. R., et al., *Differentially expressed genes that encode potential markers of goldfish macrophage development in vitro.* Dev Comp Immunol, 2004. 28(7-8): p. 727-46.
33. Justen, H. P., et al., *Differential gene expression in synovium of rheumatoid arthritis and osteoarthritis.* Mol Cell Biol Res Commun, 2000. 3(3): p. 165-72.
34. Zhu, J., et al., *Conversion of proepithelin to epithelins: roles of SLPI and elastase in host defense and wound repair.* Cell, 2002. 111(6): p. 867-78.
35. Baker, M., et al., *Mutations in progranulin cause tau-negative frontotemporal dementia linked to chromosome 17.* Nature, 2006. 442(7105): p. 916-9.
36. Cruts, M., et al., *Null mutations in progranulin cause ubiquitin positive frontotemporal dementia linked to chromosome 17q21.* Nature, 2006. 442(7105): p. 920-4.
37. Gass, J., et al., *Mutations in progranulin are a major cause of ubiquitin positive frontotemporal lobar degeneration.* Hum Mol Genet, 2006. 15(20): p. 2988-3001.
38. Rowland, L. P., *Frontotemporal dementia, chromosome 17, and progranulin.* Ann Neurol, 2006. 60(3): p. 275-7.
39. Arikawa-Hirasawa, E., et al., *Perlecan is essential for cartilage and cephalic development.* Nat Genet, 1999. 23(3): p. 354-8.
40. Kvist, A. J., et al., *Chondroitin sulfate perlecan enhances collagen fibril formation. Implications for perlecan chondrodysplasias.* J Biol Chem, 2006. 281(44): p. 33127-39.
41. Nicole, S., et al., *Perlecan, the major proteoglycan of basement membranes, is altered in patients with Schwartz-Jampel syndrome (chondrodystrophic myotonia).* Nat Genet, 2000. 26(4): p. 480-3.
42. Wallach, D., et al., *Tumor necrosis factor receptor and Fas signaling mechanisms.* Annu Rev Immunol, 1999. 17: p. 331-67.
43. Guicciardi, M. E. and G. J. Gores, *AIP1: a new player in TNF signaling.* J Clin Invest, 2003. 111(12): p. 1813-5.
44. Gupta, S., *A decision between life and death during TNF-alpha-induced signaling.* J Clin Immunol, 2002. 22(4): p. 185-94.
45. Kollias, G. and D. Kontoyiannis, *Role of TNF/TNFR in autoimmunity: specific TNF receptor blockade may be advantageous to anti-TNF treatments.* Cytokine Growth Factor Rev, 2002. 13(4-5): p. 315-21.
46. MacRae, V. E., et al., *Cytokine actions in growth disorders associated with pediatric chronic inflammatory diseases (review).* Int J Mol Med, 2006. 18(6): p. 1011-8.
47. MacRae, V. E., et al., *Cytokine profiling and in vitro studies of murine bone growth using biological fluids from children with juvenile idiopathic arthritis.* Clin Endocrinol (Oxf), 2007. 67(3): p. 442-8.
48. Martensson, K., D. Chrysis, and L. Savendahl, *Interleukin-1beta and TNF-alpha act in synergy to inhibit longitudinal growth in fetal rat metatarsal bones.* J Bone Miner Res, 2004. 19(11): p. 1805-12.
49. Xu, K., et al., *Cartilage oligomeric matrix protein associates with granulin-epithelin precursor (GEP) and potentiates GEP-stimulated chondrocyte proliferation.* J Biol Chem, 2007. 282(15): p. 11347-55.
50. Johnson, K. A., et al., *Vanin-1 pantetheinase drives increased chondrogenic potential of mesenchymal precursors in ank/ank mice.* Am J Pathol, 2008. 172(2): p. 440-53.
51. Meirelles Lda, S, and N. B. Nardi, *Murine marrow-derived mesenchymal stem cell: isolation, in vitro expansion, and characterization.* Br J Haematol, 2003. 123(4): p. 702-11.
52. Longobardi, L., et al., *Effect of IGF-I in the chondrogenesis of bone marrow mesenchymal stem cells in the presence or absence of TGF-beta signaling.* J Bone Miner Res, 2006. 21(4): p. 626-36.
53. Attur, M. G., et al., *"A system biology" approach to bioinformatics and functional genomics in complex human diseases: arthritis.* Curr Issues Mol Biol, 2002. 4(4): p. 129-46.
54. Yang, Y. C., et al., *Hierarchical model of gene regulation by transforming growth factor beta.* Proc Natl Acad Sci USA, 2003. 100(18): p. 10269-74.
55. Zavadil, J., et al., *Genetic programs of epithelial cell plasticity directed by transforming growth factor beta.* Proc Natl Acad Sci USA, 2001. 98(12): p. 6686-91.
56. Zavadil, J., et al., *Integration of TGF-beta/Smad and Jagged1/Notch signalling in epithelial-tomesenchymal transition.* Embo J, 2004. 23(5): p. 1155-65.
57. Ware, C. F., *The TNF superfamily.* Cytokine Growth Factor Rev, 2003. 14(3-4): p. 181-4.
58. Royuela, M., et al., *TNF-alpha/IL-1/NF-kappaB transduction pathway in human cancer prostate.* Histol Histopathol, 2008. 23(10): p. 1279-90.
59. Nathan, C. F., *Neutrophil activation on biological surfaces. Massive secretion of hydrogen peroxide in response to products of macrophages and lymphocytes.* J Clin Invest, 1987. 80(6): p. 1550-60.
60. Rothe, A., B. E. Power, and P. J. Hudson, *Therapeutic advances in rheumatology with the use of recombinant proteins.* Nat Clin Pract Rheumatol, 2008. 4(11): p. 605-14.
61. Aizawa, T., et al., *Induction of apoptosis in chondrocytes by tumor necrosis factor-alpha.* J Orthop Res, 2001. 19(5): p. 785-96.
62. Horiguchi, M., et al., *Tumour necrosis factor-alpha up-regulates the expression of BMP-4 mRNA but inhibits chondrogenesis in mouse clonal chondrogenic EC cells, ATDC5.* Cytokine, 2000. 12(5): p. 526-530.
63. MacRae, V. E., C. Farquharson, and S. F. Ahmed, *The pathophysiology of the growth plate in juvenile idiopathic arthritis.* Rheumatology (Oxford), 2006. 45(1): p. 11-9.
64. Luan, Y., et al., *Inhibition of ADAMTS-7 and ADAMTS-12 degradation of cartilage oligomeric matrix protein by alpha-2-macroglobulin.* Osteoarthritis Cartilage, 2008. 16(11): p. 1413-20.
65. He, Z. and Bateman, A., *Progranulin gene expression regulates epithelial cell growth and promotes tumor growth in vivo.* Cancer Res, 1999. 59, p. 3222.
66. He, Z. et al., *Progranulin is a mediator of the wound response.* Nat Med, 2003. 9, p. 225.
67. Zhu, J. et al., *Conversion of proepithelin to epithelins: roles of SLPI and elastase in host defense and wound repair.* Cell, 2002. 111, p. 867.

EXAMPLE 5

Acute Inflammation Air Pouch Model Studies

Figure 21:
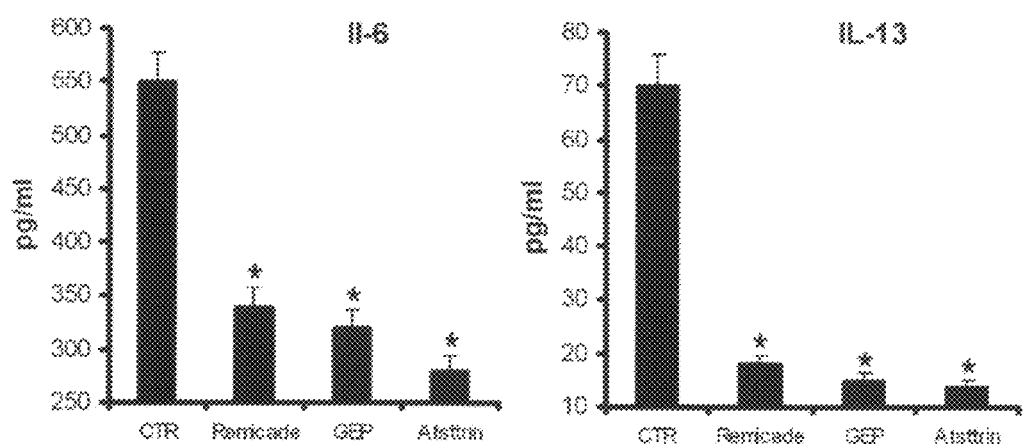
FIG. 21 depicts IL-6 and IL-13 levels in cell-free exudates of mice from an air-pouch acute inflammation model. Levels of IL-6 and IL-13 are depicted in controls (CTR) and animals administered Remicade (10 µg/g), GEP (10 µg/g), and Atsttrin (10 µg/g).

Anti-inflammatory activity of GEP and Atsttrin were tested in an air pouch-induced acute inflammation animal model. To induce air pouches, 10-15-week-old male mice were injected subcutaneously on the back with 3 ml of air. After 2 days, the pouches were reinflated with 1.5 ml of air. On day 6, inflammation was induced by injection of 1 ml of a suspension of carrageenan (2% weight/volume in calcium- and magnesium-free phosphate buffered saline solution [PBS]) into the air pouch. Remicade (10 ug/g), GEP (10 ug/g) and Atsttrin (10 ug/g) was administered 1 hour prior to induction of inflammation in the air pouch. After 4 hours, the mice were killed by CO, narcosis, the pouches were flushed with 2 ml of PBS, and exudates were harvested. After centrifugation (1,000 g for 10 minutes), the cell-free exudates were collected. The IL-6 and IL-13 concentration was quantitated in the exudates in duplicate by enzyme-linked immunosorbent assay (R&D Systems, Minneapolis, Minn.) following the manufacturer's instructions. As showed in FIG. 21, both GEP and its derived Atsttrin potently reduce the level of IL-6 and IL-13, two major inflammatory mediators. Note that both GEP and Atsttrin exhibit more effective anti-inflammation (approximately 80% reduction in IL-13 concentration) than Remicade in this model.

EXAMPLE 6

Chronic Inflammation Animal Model Studies

GEP activity is determined in a rheumatoid arthritis animal model. In this study, female BALB/cJ mice are used. The animals are housed at a density of three to four per cage and allowed to acclimate for one week. A combination of four different monoclonal antibodies to the well-defined epitopes of Collagen II (mAbs: C11b, J1, D3, and U1) are administered IV (on Day 0). Three days later (Day 3), mice are challenged with lipopolysaccharide administered IP (LPS, 25 μg/mouse). Test compound and vehicle are administered according to study design beginning one hour post-LPS challenge on Day 3. Paw edema is measured on Days −1, 4, 7, 10 and 11. Arthritis Scores in mice are visually examined for signs of joint inflammation on Days −1, 3, 5, 7, and 10. Body weights are determined on all days when arthritis scores are obtained. Blood is drawn at necropsy and processed to serum or plasma. Mice are euthanized after obtaining final caliper measurements on Day 11. Hind legs are taken and fixed for histopathology analysis.

EXAMPLE 7

GEP and Atsttrin Effects on Progression of Arthritis in TNFα Transgenic Mice

Mice transgenic for human TNFα, originally generated by Dr. George Kollias' laboratory, develop a chronic inflammatory and destructive polyarthritis with many characteristics observed in rheumatoid arthritis patients [55]. The phenotype of this mouse model validated the theory that TNFα is at the apex of the pro-inflammatory cascade in rheumatoid arthritis, and foreshadowed the remarkable success of anti-TNFα therapy that has transformed the effective management of this disease. As such, the TNFα transgenic mice are very useful tools for dissecting the molecular mechanisms of the pathogenic process and evaluating the efficacy of novel therapeutic strategies for rheumatoid arthritis [115, 138, 139]. This model is used to further assess GEP, especially its derived peptide(s) atsttrin, direct administration to treat rheumatoid arthritis. Briefly, TNFα transgenic mice (n=60, purchased from Taconic) are divided into 6 groups of 10 mice each and receive GEP, GEP-derived peptide, and anti-TNFa antibody (serves as a control) at doses described in the literature as being effective [140, 141]. All treatments are administered by intraperitoneal injection. Group 1 is treated with phosphate buffered saline and serves as a negative control. Group 2 and 3 (low does of GEP and GEP-derived peptide(s)) receive 1 mg/g of GEP or peptide(s) 3 times weekly from week 4 to week 10. Group 4 and 5 (high does) receive 10 mg/g of GEP or peptide(s) 3 times weekly from week 4 to week 10. Group 6 receive 10 mg/g of anti-TNFα 3 times weekly from week 4 to week 10. At week 10, all animals are sacrificed by cervical dislocation, blood is withdrawn by heart puncture, and the paws and tibial bones are dislocated for further analyses. Clinical evaluation is performed weekly, starting at 4 weeks after birth. Arthritis is evaluated in each group of animals.

EXAMPLE 8

GEP and Atsttrin Effects on RANKL-Induced Osteoclastogenesis

Figure 22:
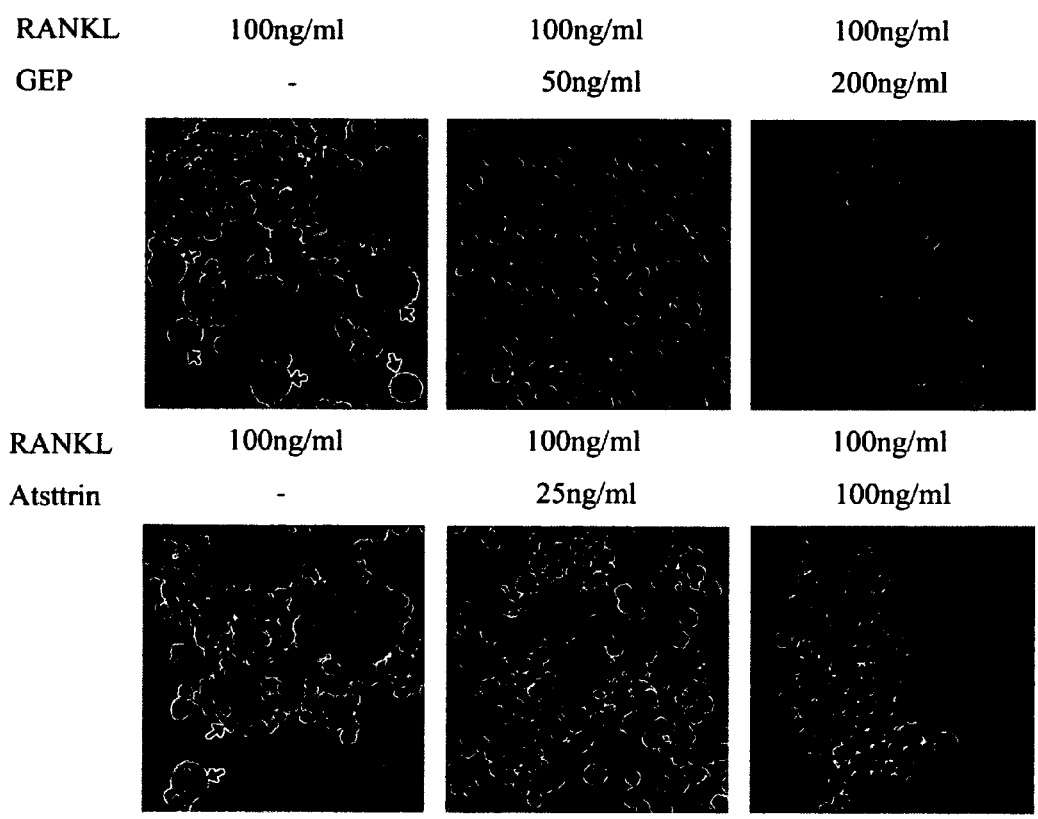
FIG. 22 depicts RANKL-induced osteoclastogenesis, as assessed by TRAP staining. Raw 264.7 macrophages were incubated in the presence of RANKL for 4 days, alone or with varying amounts of GEP or atsttrin.

Osteoclasts are the bone-resorbing cells, and their excess activity causes osteoporosis. RANKL is the key receptor for osteoclastogenesis and binds RANK. RANK and TNFR belong to the same TNFR family and they share significant similarity in sequence and particularly in structure. Given that (1) RANK, the key receptor for osteoclastogenesis, belongs to the TNFR subfamily, and that (2) GEP and its derived peptide Atsttrin binds to TNFR and blocks TNF alpha action, we also examined whether GEP and Atsttrin affect osteoclastogenesis. RANKL-induced osteoclastogenesis was assessed in the presence and absence of GEP or peptide atsttrin. Briefly, we cultured Raw 264.7 macrophages in the presence of RANKL for 4 days and TRAP staining was performed. As expected, RANKL induced robust osteoclastogenesis and TRAP multinucleated positive cells were observed (FIG. 22, indicated with arrows). GEP and atsttrin demonstrated doesdependent inhibition of osteoblast differentiation (FIG. 22). Interesting, atsttrin appears to be more potent than GEP in blocking osteoclastogenesis. The finding that atsttrin inhibits osteoclastogenesis indicates that this peptide also has potential for treating osteoporosis in addition to various kinds of inflammatory diseases, including rheumatoid arthritis.

EXAMPLE 9

GEP and Atsttrin Binding to TNF Family Members RANKL and FAS

Figure 26:
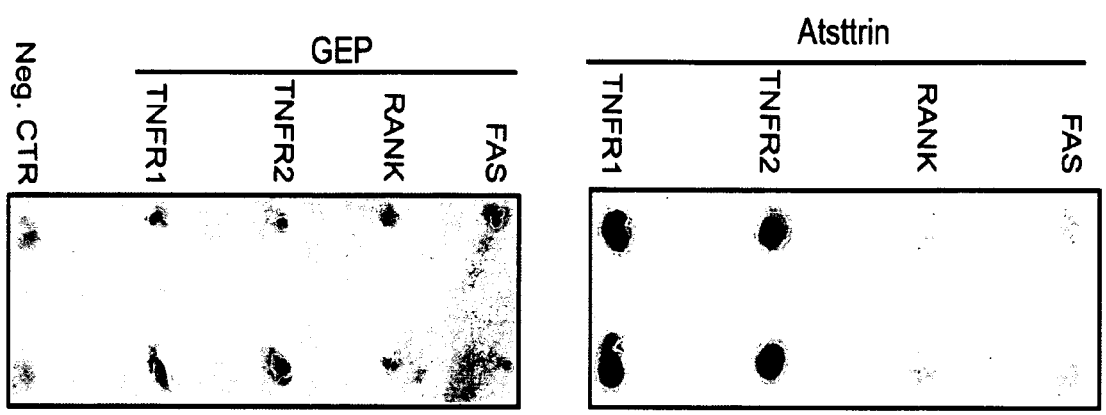
FIG. 26 shows that GEP associates with RANK and FAS in addition to TNFR, whereas Atsttrin specifically binds to TNFR (yeast two hybrid assay). Each pair of plasmids, as indicated, was co-transformed into yeast strain MAV203. Yeast transformants were selected on SD-leu$^-$/trp$^-$/his$^-$/ura$^-$/3AT$^+$ plates and tested for β-galactosidase activity. The lack of interaction between Rb and lamin was used as a negative control (Neg. CTR).

The interactions between GEP/Atsttrin and other members in TNF receptors (TNFR) subfamily, including RANK and FAS, were examined. To assess binding, various pairs of plasmids, were co-transformed into yeast strain MAV203 and a yeast two-hybrid assay was performed (FIG. 26). GEP plasmids were co-transformed with each of TNFR1, TNFR2, RANK and FAS plasmids. Atsttrin plasmids were co-transformed with each of TNFR1, TNFR2, RANK and FAS plasmids. Yeast transformants were selected on SD-leu$^-$/trp$^-$/his$^-$/ura$^-$/3AT$^+$ plates and tested for β-galactosidase activity. The lack of interaction between Rb and lamin was used as a negative control. By this two-hybrid assay, GEP associates with RANK and FAS in addition to TNFR, whereas Atsttrin specifically binds to TNFR.

These studies demonstrate that GEP also binds to RANK and Fas, although the interaction may be weaker than that with TNFR1 and TNFR2. In contrast, Atsttrin, which shows higher binding affinity to TNF (TNFR1 and TNFR2) receptors than does GEP, does not interact directly with RANK and FAS as assessed by two-hybrid binding assay. Thus, due to its specificity for TNFR, Atsttrin may have less or distinct sideeffects and toxicity than does GEP because GEP associates with the other member of the TNFR family RANK and thus may affect multiple pathophysiological processes.

We have previously showed that Atsttrin potently inhibits RANKL-induced osteoclastogenesis (Example 8). The present example results now demonstrate that Atsttrin does not bind to RANK. Collectively, these data suggest that Atsttrin-mediated inhibition of osteoclastgenesis must be through blocking the TNF/TNFR pathway. Indeed, growing evidence demonstrates that TNF/TNFR signaling is also crucial for osteoclastogenesis.

EXAMPLE 10

GEP Exhibits Higher Binding Affinity for TNFR Than Does TNFα

Figure 27:
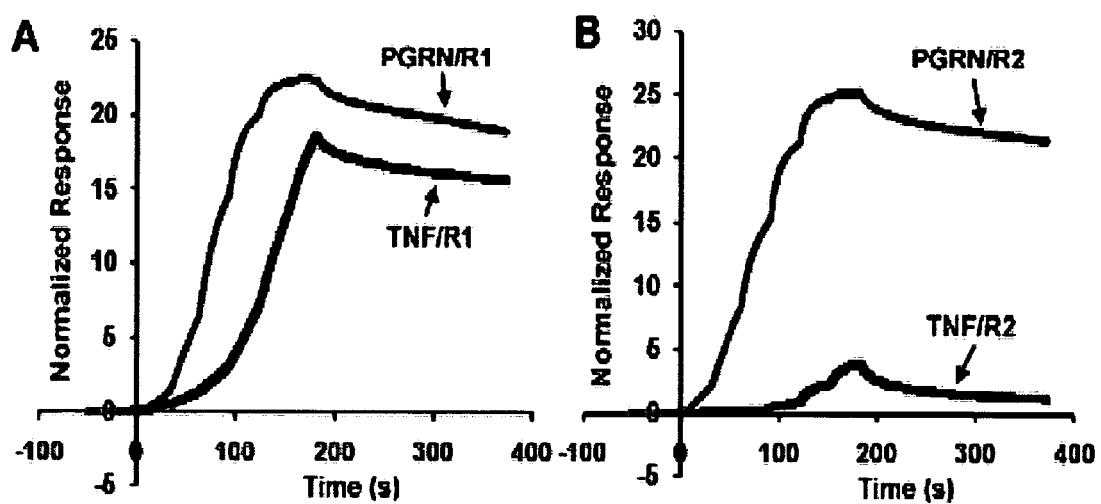
FIG. 27 provides FastStep™ Kinetic Assay for binding of GEP (PGRN) and TNFα to TNFR1 (R1) and TNFR2 (R2).

Kinetic binding studies of GEP and TNFα to TNFR were observed and analyzed using Analytical Surface Plasmon Resonance with SensiQ Pioneer (ICx Nomadics, Oklahoma City, Okla. 73104). The kinetic binding is shown in FIG. 27, and the kinetic constants are summarized in TABLE 1. Remarkably, GEP exhibits higher affinity for TNF receptors, especially TNFR2 when compared to TNFα ($K_D$ of GEP vs. TNFα: $1.28 \times 10^{-9}$M vs. $7.64 \times 10^{-7}$M). In contrast to TNFα, which shows much higher affinity for TNFR1 (KD $8.8 \times 10^{-9}$ M) than TNFR2 (KD $7.64 \times 10^{-7}$M), GEP exhibits slightly higher affinity for TNFR2 (KD $1.28 \times 10^{-9}$ M) than TNFR1 (KD $1.58 \times 10^{-9}$M).

TABLE 1

Kinetic Constants

| Analyte | $K_a$ ($\times 10^4$ M$^{-1}$S$^{-1}$) | $K_d$ ($\times 10^{-4}$ S$^{-1}$) | $K_D$ (M) |
|---|---|---|---|
| TNFα/TNFR1 | 8.25 | 7.27 | $8.80 \times 10^{-9}$ |
| GEP/TNFR1 | 51.6 | 8.14 | $1.58 \times 10^{-9}$ |
| TNFα/TNFR2 | 7.79 | 59.5 | $7.64 \times 10^{-7}$ |
| GEP/TNFR2 | 540 | 6.92 | $1.28 \times 10^{-9}$ |

EXAMPLE 11

Binding Studies of Atsttrin and TNFR

Figure 28:
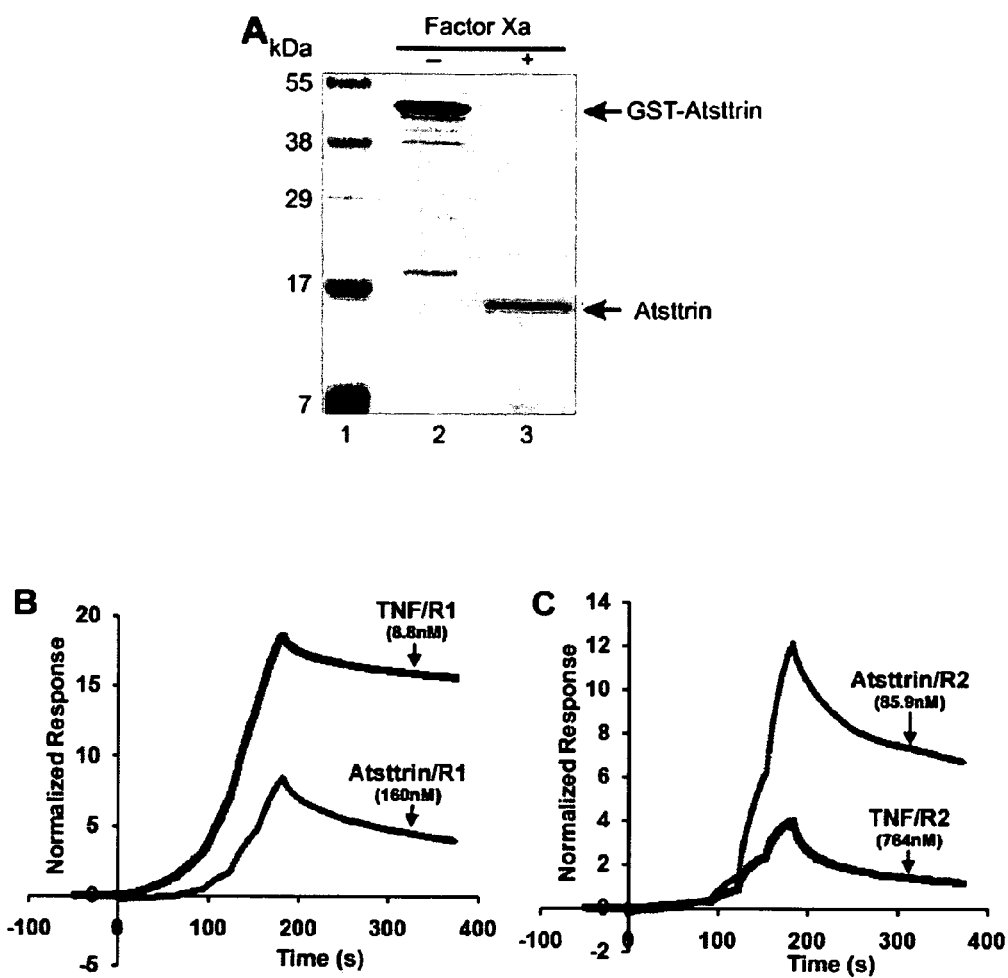
FIGS. 28A, 28B and 28C provides (A) characterization of recombinant Atsttrin. GST-Atsttrin conjugated to glutathione agarose resin and Atsttrin released by factor Xa were resolved by SDS-PAGE and the proteins were stained with Coomassie Brillian Blue R-250. (B) and (C) provide the FastStep™ Kinetic Assay for binding of Atsttrin and TNFα to TNFR1 (R1) and TNFR2 (R2).

Atsttrin was expressed in bacteria as a GST fusion protein, purified on glutathione agarose resin, and eluted using Xa factor (there is a Xa factor cleavage site between GST and Atsttrin) (FIG. 28A). Xa factor was then removed from the elution using Xa Removal Resin (Qiagen). Purified Atsttrin was analyzed for endotoxin using the Limulus amebocyte lysate assay, which indicated endotoxin levels similar to control medium, many fold below the manufacturer's specification of <1 unit/μg. Using Analytical Surface Plasmon Resonance Assay (FIG. 28 B & C), we were excited to find that Atsttrin exhibited ~9-fold higher binding affinity for TNFR2 (KD of Atsttrin/TNFR2 vs. TNFα/TNFR2: $8.59 \times 10^{-8}$M vs. $7.64 \times 10^{-7}$M), but ~18-fold lower affinity for TNFR1 than TNFα (KD of Atsttrin/TNFR1 vs. TNFα/TNFR1: $1.60 \times 10^{-7}$M vs. $8.80 \times 10^{-9}$M), suggesting that Atsttrin can block the TNFα/TNFR2 pathway effectively, but may not significantly affect TNFα/TNFR1 signaling.

EXAMPLE 12

Figure 29:
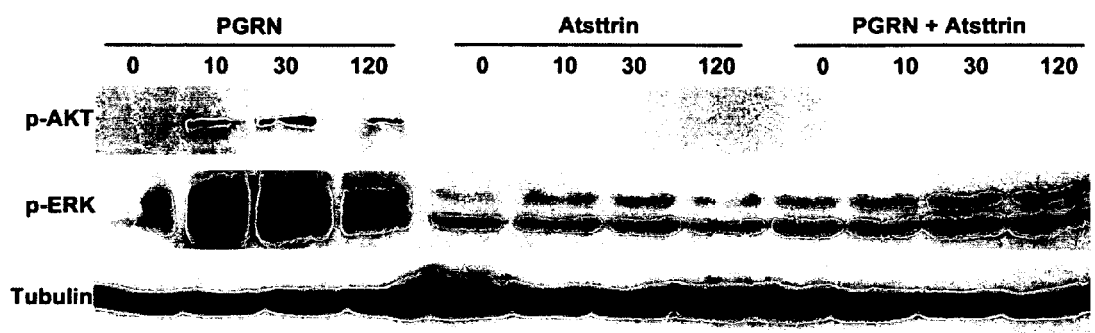
FIG. 29 depicts PathScan® Multiplex Western Blot results against p-AKT, p-ERK and tubulin control with GEP, Atsttrin and GEP+Atsttrin. GEP activates both the Akt and Erk1/2 pathways, but Atsttrin does not. In the combination study, Atsttrin blocked GEP-mediated activation of the oncogenic p-AKT and p-ERK pathways.

Atsttrin Fails to Activate Erk1/2 and Alit Signaling and Inhibits Cancer Cell Proliferation Using the PathScan® Multiplex Western Cocktail I (Cell Signaling) that allows one to simultaneously detect levels of phospho-p90RSK, phospho-Akt, phospho-p44/42 MAPK (Erk1/2), and phospho-S6 ribosomal protein on a single membrane, we next sought to compare GEP- and Atsttrin-activated signaling in chondrocytes. Human C28I2 chondrocytes (provided by Dr. Mary B. Goldring) were starved for 24 hr and treated with 50 ng/ml of GEP or Atsttrin for various time points, and cell lysates were analyzed using the PathScan® Multiplex Western Cocktail I. As shown in FIG. 29, GEP strongly activated Erk1/2 and moderately activated Akt pathways (Feng, J., Guo, F., Jiang, B., Frenkel, S., Zhang, Y., Wang, D., Liu, C. J., GEP: A BMP2-Inducible Growth Factor that Activates Erk1/2 Signaling and JunB Transcription Factor in Chondrogenesis, *FASEB J.*, 2010 Feb. 2 [Epub ahead of print]). However, Atsttrin, while retaining the TNFR-binding activity of GEP (FIG. 28), loses GEP's oncogenic signaling. When GEP and Atsttrin are tested in combination, Atsttrin blocks or suppresses GEP-mediated activation of p-AKT and p-ERK (FIG. 29).

EXAMPLE 13

Figure 31:
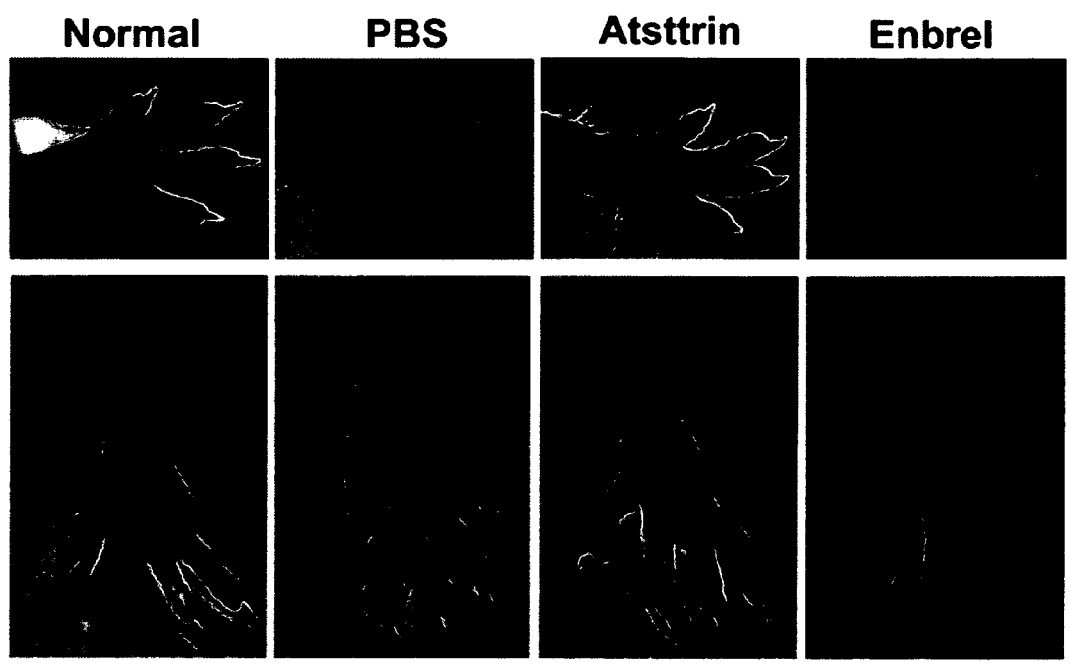
FIG. 31 provides photographs of the front (top) and hind (bottom) paws of normal and CIA mice treated with PBS, Atsttrin, or Enbrel.

Atsttrin Prevents the Onset of Arthritis in a Collagen-Induced arthritis (CIA) Model We next examined Atsttrin in a collagen-induced arthritis (CIA) mouse model that exhibits many of the clinical and pathological features of RA. Briefly, DBA/1 mice were challenged on day 0 with chick collagen II emulsified in modified complete Freund's adjuvant given s.c. at the base of the tail (Chondrex Single Immunization). On day 19, mice were divided into three groups (each n=10) and treated every other day until day 35, as follows: Group 1 received Atsttrin at a dose of 10 pg/g body weight i.p., Group 2 received Enbrel (soluble extracellular domain of TNFR2) at a dose of 10 pg/g body weight i.p. (serving as positive control), and Group 3 received an equal volume of phosphate-buffered saline (PBS, serving as negative control). Mice were monitored daily for incidence of arthritis, arthritis severity score, and paw thickness measured by a constant pressure caliper. As shown in FIGS. 30A and 30B, both Atsttrin and Enbrel effectively prevented the development of arthritis. Atsttrin was more potent than Enbrel in this model, since Atsttrin completely prevented the onset of arthritis. As seen in the representative panels in FIG. 31, symptoms of CIA (swelling, erythema, deformity) were apparent in mice treated with PBS. In contrast, mice treated with Atsttrin and Enbrel demonstrated markedly reduced pathology, and Atsttrin-treated mice were similar to normal mice. Ankles from CIA mice treated with PBS exhibited robust leukocyte infiltration and tissue destruction (H&E staining) and loss of matrix staining (Sarfranin-O staining) (FIG. 32A). Arthritic symptoms were absent in Atsttrin-treated mice. MicroCT images (FIG. 32B) revealed clear bone erosion in CIA mice treated with PBS, but not with Atsttrin. In addition, bone-resorbing osteoclasts were clearly seen with TRAP+ around the erosive area in CIA mice treated with PBS; in contrast, TRAP+ osteoclasts were hardly detectable in Atsttrin-treated CIA mice (FIG. 33).

We evaluated Atsttrin effects of the levels of proinflammatory and anti-inflammatory cytokines in the sera of the CIA mice. Atsttrin was compared to PBS and Enbrel in these studies. Proinflammatory cytokines IL-1β and IL-6 were evaluated and anti-inflammatory cytokines IL-10 and IL-13 were assessed. As shown in FIG. 34, both Atsttrin and Enbrel significantly reduced the levels of the pro-inflammatory cytokine IL-6. IL-1β was less significantly reduced by Enbrel and Atsttrin, although Atsttrin reduced IL-1β more than Enbrel did. With regard to anti-inflammatory cytokines, while both Enbrel and Atsttrin increased IL-10, Atsttrin showed a more significant effect on IL-10 levels. Both Enbrel and Atsttrin increased the amount of the anti-inflammatory cytokine IL-13.

EXAMPLE 14

Effects of Atsttrin on TNF-Induced Activities in Cells

Figure 36:
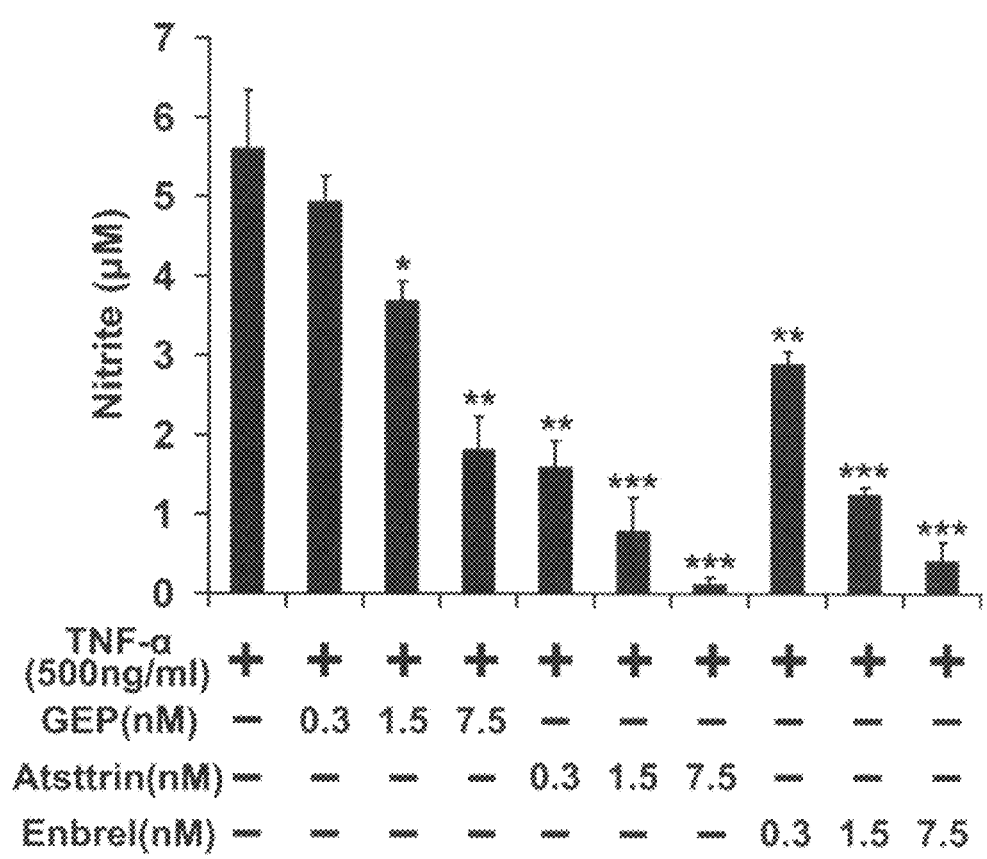
FIG. 36 depicts GEP and Atsttrin effects on TNF-induced nitrite production. TNFα was added to RAW264.7 cells with concomitant addition of 0.3 nM, 1.5 nM or 7.5 nM GEP, Atsttrin or Enbrel as indicated and µM nitrite was measured.
Figure 37:
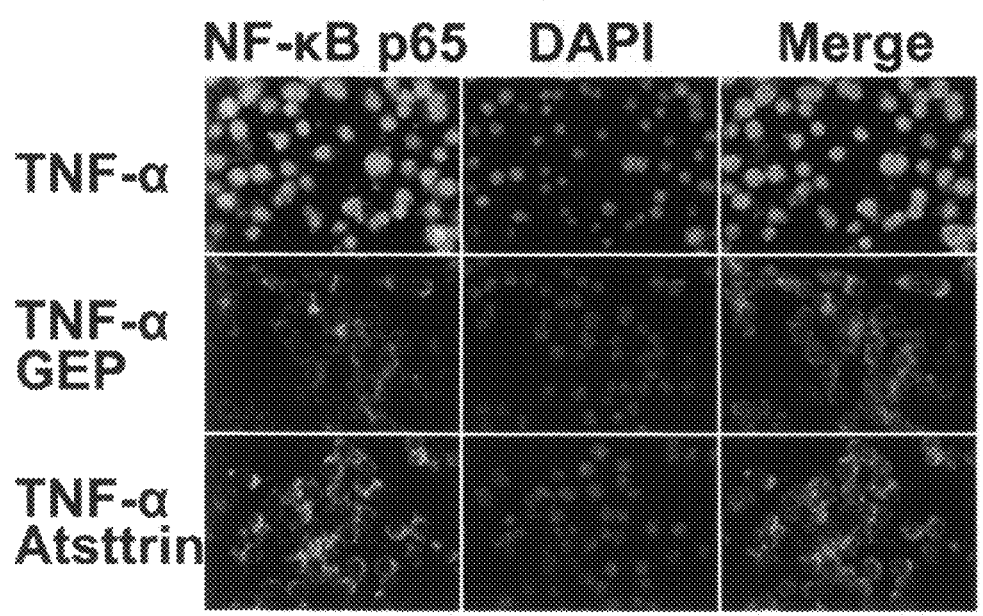
FIG. 37 evaluates TNF-induced nuclear accumulation of NF-κB by immunofluorescence of RAW264.7 cells in the presence of TNF-α, TNF-α and GEP, or TNF-α and Atsttrin. Cells were stained for NF-κB p65, versus nuclear DAPI stain, and merged for both stains. NF-κB staining remains cytoplasmic in the presence of GEP or Atsttrin.
Figure 38:
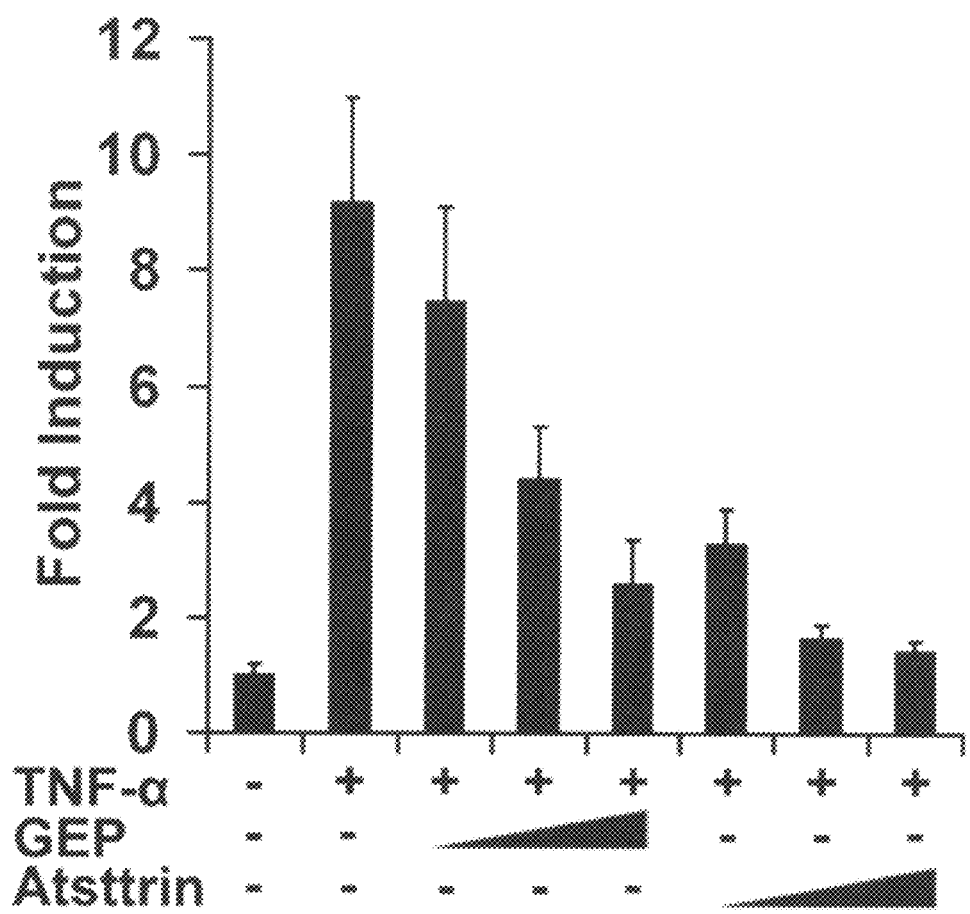
FIG. 38 shows fold induction of a TNF-activated NFκB reported gene in the presence of TNF-α alone, or combined with either GEP or Atsttrin at increasing concentrations. GEP and Atsttrin inhibit TNF-α mediated activation of the NFκB reported gene.

In vitro cell-based studies in RAW 264.7 cells were utilized to further assess and evaluate Atsttrin effects of TNF responses in cells. GEP and Atsttrin were evaluated for their effects on TNF-induced nitrite production. Nitrite production was determined in cells in the presence of added TNF (500 ng/ml) and with increasing amounts of either GEP, Atsttrin or Enbrel (0.3, 1.5 and 7.5 nM). While GEP reduced nitrite production somewhat, each of Atsttrin and Enrel reduced TNF-induced nitrite production more significantly (FIG. 36). Next, TNF-induced nuclear accumulation of NFκB was evaluate in cells. Both GEP and Atsttrin blocked TNF-induced nuclear accumulation of NFκB as assessed by NFκB p65 staining (FIG. 37). Induction of a TNF-activated NFκB reporter gene (PAK-1 with an NFκB binding site) was determined in the presence of TNFα and either GEP or Atattrin at increasing concentrations (FIG. 38). Atsttrin inhibited the reporter gene's induction more significantly that GEP at lower concentrations.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. An isolated peptide comprising
Granulin/epithelin precursor (GEP) granulin units F (amino acids 126-178 of SEQ ID NO: 1), A (amino acids 284-335 of SEQ ID NO: 1), and C (amino acids 366-416 of SEQ ID NO: 1); and
GEP linker units P3 (amino acids 179-205 of SEQ ID NO:1), P4 (amino acids 262-283 of SEQ ID NO:1), and P5 (amino acids 336-365 of SEQ ID NO:1), wherein the peptide antagonizes TNFR1 or TNFR2 signaling, and wherein the peptide is a mixed portion of the full-length GEP sequence.

2. An isolated peptide comprising:
at least ½F (amino acids 153-178 of SEQ ID NO: 1);
P3 (amino acids 179-205 of SEQ ID NO:1)
P4 (amino acids 262-283 of SEQ ID NO:1)
at least ½A (amino acids 284-304 of SEQ ID NO: 1);
P5 (amino acids 336-365 of SEQ ID NO:1); and
at least ½C (amino acids 366-392 of SEQ ID NO: 1);
wherein the peptide antagonizes TNFR1 or TNFR2 signaling, and wherein the peptide is a mixed portion of the full-length GEP sequence.

3. The isolated peptide of claim 1, comprising:
(a) amino acids 126-205 of SEQ ID NO: 1;
(b) amino acids 262-335 of SEQ ID NO: 1; and
(c) amino acids 336-416 of SEQ ID NO: 1.

4. An isolated peptide comprising SEQ ID NO: 2 or a variant thereof having at least 90% sequence identity to SEQ ID NO: 2, wherein the peptide antagonizes TNFR1 or TNFR2 signaling.

5. The isolated peptide of claim 4, wherein the peptide comprises SEQ ID NO: 2.

6. A pharmaceutical composition comprising the isolated peptide of claim 1 and a pharmaceutically acceptable carrier, vehicle, or diluent.

7. The composition of claim 6 further comprising one or more of an anti-inflammatory agent or compound, an anti-cancer agent or compound, and an immunomodulatory agent.

8. A pharmaceutical composition comprising the isolated peptide of claim 4 and a pharmaceutically acceptable carrier, vehicle, or diluent.

9. The composition of claim 8 further comprising one or more of an anti-inflammatory agent or compound, an anti-cancer agent or compound, and an immunomodulatory agent.

10. A pharmaceutical composition comprising the isolated peptide of claim 2 and a pharmaceutically acceptable carrier, vehicle, or diluent.

11. The composition of claim 10 further comprising one or more of an anti-inflammatory agent or compound, an anti-cancer agent or compound, and an immunomodulatory agent.

* * * * *

UNITED STATES PATENT AND TRADEMARK OFFICE
CERTIFICATE OF CORRECTION

PATENT NO. : 8,362,218 B2
APPLICATION NO. : 12/799024
DATED : January 29, 2013
INVENTOR(S) : Chuanju Liu It is certified that error appears in the above-identified patent and that said Letters Patent is hereby corrected as shown below:

In the Specification

In Column 1, Lines 18-22, replace:
"This invention was made with government support under NIH/NIAMSI K01 AR053210 and NIH/NIA 1 R03 AG029388, awarded by the National Institute of Health, National Institute of Arthritis and Musculoskeletal and Skin Diseases. The government has certain rights in the invention."

With:
-- This invention was made with government support under Grant Nos. NIH AR052022, NIH AR050620, NIH AR053210 and NIH AG029388, awarded by the National Institutes of Health, National Institute of Arthritis and Musculoskeletal and Skin Diseases. The government has certain rights in the invention. --

Signed and Sealed this
Twenty-seventh Day of October, 2020

Andrei Iancu
*Director of the United States Patent and Trademark Office*